US010941185B2

(12) United States Patent
Chen et al.

(10) Patent No.: US 10,941,185 B2
(45) Date of Patent: Mar. 9, 2021

(54) STRAIN OF BACTERIA PRODUCING DHA AND EPA, SIX GENE FRAGMENTS IN THE BACTERIAL GENOME AND THEIR APPLICATIONS

(71) Applicant: XIAMEN HUISON BIOTECH CO., LTD., Xiamen (CN)

(72) Inventors: Liyi Chen, Xiamen (CN); Huichang Zhong, Xiamen (CN); Shuirong Chen, Xiamen (CN)

(73) Assignee: XIAMEN HUISON BIOTECH CO., LTD., Xiamen (CN)

( * ) Notice: Subject to any disclaimer, the term of this patent is extended or adjusted under 35 U.S.C. 154(b) by 0 days.

(21) Appl. No.: 16/696,331

(22) Filed: Nov. 26, 2019

(65) Prior Publication Data

US 2020/0087357 A1 Mar. 19, 2020

Related U.S. Application Data

(63) Continuation of application No. PCT/CN2018/087613, filed on May 21, 2018.

(30) Foreign Application Priority Data

May 31, 2017 (CN) ........................ 201710398286.7
Nov. 10, 2017 (CN) ........................ 201711102734.0

(51) Int. Cl.
*C07K 14/37* (2006.01)
*C12N 1/14* (2006.01)
*C12P 7/64* (2006.01)
*C12R 1/645* (2006.01)

(52) U.S. Cl.
CPC ................ *C07K 14/37* (2013.01); *C12N 1/14* (2013.01); *C12P 7/6427* (2013.01); *C12R 1/645* (2013.01); *C07K 2319/00* (2013.01)

(58) Field of Classification Search
CPC ...................................................... C07K 14/37
See application file for complete search history.

(56) References Cited

U.S. PATENT DOCUMENTS 7,939,305 B2 * 5/2011 Luy ...................... C12P 7/6472
435/183

FOREIGN PATENT DOCUMENTS

| | | | |
|---|---|---|---|
| CN | 101087882 | | 12/2007 |
| CN | 101817738 | | 9/2010 |
| CN | 102864111 | | 1/2013 |
| CN | 103865642 | | 6/2014 |
| CN | 105018539 | | 11/2015 |
| CN | 105132485 | A | 12/2015 |
| CN | 105331572 | A | 2/2016 |
| CN | 105420122 | A | 3/2016 |
| CN | 106987528 | | 7/2017 |
| WO | 2006/135866 | A2 | 12/2006 |

OTHER PUBLICATIONS

International search report dated Aug. 3, 2018 from corresponding application No. PCT/CN2018/087613.
Office Action dated Mar. 22, 2019 and English translation from corresponding application No. CN 201710398286.7.
Office Action dated Sep. 10, 2019 and English translation from corresponding application No. CN 201710398286.7.
Office Action issued in corresponding Chinese Application No. 201711102734.0; dated Apr. 22, 2020; 13 pgs.
European Search Opinion and Search Report issued in corresponding European Application No. 18810206.5; dated May 27, 2020; 9 pages.
Huang J. et al: "Expressed sequence tag analysis of marine fungus Schizochytrium producing docosahexaenoic acid", Journal of Biotechnology, Elsevier, Amsterdam, NL, vol. 138, No. 1-2, Nov. 6, 2008, pp. 9-16.
Zhang, Ke et al: "Regulation of the Docosapentaenoic AcidlDocosahexaenoic Acid Ratio (DPA/DHA Ratio) in Schizochytrium limacinum B4D1", Applied Biochemistry and Biotechnology, Humana Press NC, New York, vol. 182, No. 1, Nov. 10, 2016, pp. 67-81.

(Continued)

*Primary Examiner* — Karen Cochrane Carlson
(74) *Attorney, Agent, or Firm* — Hauptman Ham, LLP

(57) ABSTRACT

The present invention discloses a strain of bacteria producing DHA and/or EPA, six gene fragments in the bacterial genome, and uses thereof. The strain is *Schizoochytrium limacinum* HS01, which has the accession number of CGMCC No. 13746 at China General Microbiological Culture Collection Center. The six gene fragments are composed of gene fragment 1 to gene fragment 6, and the nucleotide sequences are sequentially as shown in SEQ ID NO: 3 to SEQ ID NO: 8 in the Sequence Listing. The experiments prove that fermentation broth containing DHA and EPA can be obtained by fermenting *Schizoochytrium limacinum* HS01; the recombinant strain is obtained by introducing gene fragment 1 to gene fragment 6 into *Schizoochytrium limacinum* MYA-1381; the ability the recombinant strain for producing DHA and EPA is greatly improved. The bacteria provided by the invention, the six gene fragments, the protein encoded by these six gene fragments, the vector, the cell or the organism containing these six gene fragments all have important application values.

10 Claims, 1 Drawing Sheet

Specification includes a Sequence Listing.

(56) References Cited

OTHER PUBLICATIONS

Metz, James et al: "Biochemical characterization of polyunsaturated fatty acid synthesis in Schizochytrium: Release of the products as free fatty acids", Plant Physiology and Biochemistry, Gauthier-Villars, Paris, FR, vol. 47, No. 6, Jun. 1, 2009, pp. 472-478.

Ye, Chao et al: "Reconstruction and analysis of the genome-scale metabolic model of schizochytrium limacinum SR21 for docosahexaenoic acid production", BMC Genomics, Biomed Central, vol. 16, No. 1, Oct. 16, 2015, p. 799 (11 pgs).

* cited by examiner

SEQUENCE LISTING

```
<160> NUMBER OF SEQ ID NOS: 15

<210> SEQ ID NO 1
<211> LENGTH: 207
<212> TYPE: DNA
<213> ORGANISM: Schizoochytrium limacinum

<400> SEQUENCE: 1

agccatgcat gtgtaagtat aagcgattgt actgtgagac tgcgaacggc tcattatatc     60

agtaataatt tcttcggtag tttcttttat atggatacct gcagtaattc tggaaataat    120

acatgctgta agagccctgt atggggctgc acttattaga ttgaagccga ttttattggt    180

gaatcatgat aattgagcag attgact                                        207


<210> SEQ ID NO 2
<211> LENGTH: 239
<212> TYPE: DNA
<213> ORGANISM: Schizoochytrium limacinum

<400> SEQUENCE: 2

gagttctgcc tctgtccaaa aattaatcca aacagaaaca tcccatggtt tcatcggacc     60

gttcaatcgg taggtgcgac gggcggtgtg tacaaagggc agggacgtat tcaatgcaag    120

ctgatgactt gcgtttacta ggaattcctc gttggagatt aataattgca aaaatctagc    180

cccagcacga tgagcgttcc aaggattagc caggccttcc gaccaagcac tcaattcca     239


<210> SEQ ID NO 3
<211> LENGTH: 4100
<212> TYPE: DNA
<213> ORGANISM: Schizoochytrium limacinum

<400> SEQUENCE: 3

cacattcgct acaaaacgcc gcagtttcta tggtttgatt cctttgaccc ctaaagaatt     60

gttcgaaagg gtgtgttctc ctggagagga catcaccgat tcttcgttag atgccgactc    120

cgtagagacg gcagaaagcg agccttctgc agagcccaag aacaagcaag atggggttca    180

tcgtgccgag gttgctactt tggatggatt cgggtaagtt catgcggtta atctttgttt    240

gggatcgtgt gatcaatcat tccacgaatt gtgttattga gatagaggga atcctaactt    300
```

-continued

```
tttgcttcta atttattac tccttcaccc tgctcgtttg cttacgtctt cttattcgcc    360
tcagagaacg gccggatgga gcgagcgtga gtttcgctga tgtggtgcag cttgccaaaa    420
acgtctcgaa cttgcgcgcg gaccgaggcg gggtcagagg aaactccctg cagactggga    480
ttgccttgct tgaggaattt attcgaccgg cgatccaggg ctactttggc caagtgaagt    540
tgcgacaggt ctccgctgac atcaagaact ccaaacagtg tcttgatgca ctacaaggcc    600
agattcgtgc aagctctgca aatgagttgc ccagtctcat cgaaaagcgg aatgctgaac    660
gagaccgcct acgtttacta atgcaagtcg tgtacccatg gactcgcgca aacctctgcg    720
aaagtgatga ggatgtagtc cgcgatttca aatgagaat tgaaagtttg gtacacgatt    780
taaagatcac tcttgcaccg gttactgaaa agaccagcac agatgacttc aaacactgcc    840
aagaactcgt tgctcgggct gtccaatgcg tcgaaggata caagagaaat ggagatggcc    900
gaccaaacaa cattggcgaa cgaagccaac aagctgcaaa atgcgtcgtc tctcgattgt    960
ctgagctaga acttggtgat ggattatggg ttgctcttag gatacctgag caggccatga   1020
atctcggacc cgaattatcc gagcttgagc gtgctcttca agaagagatt gaagtgctac   1080
aaggagatac acttagtgcc cacttatcta agatactttg cgcaataagt tcaacattcg   1140
ctcgtttcga atcatactgt gaaaacactg tgctgaatga agcgagcaag tgcacaccac   1200
aagagctctc tgaactatat gattatacat cactgggttt gaaagaacct tccgtcttag   1260
atgttgataa attgtatcag aaacttggca agtcgaggga agccacaaag agtttgaaaa   1320
gagctagaga agagctcgaa gctgaggacc tggaagagga agaacgagaa tattttagaa   1380
atcgaatcaa gaaacagaag cgcattcttt ctaaaggcaa ccctatcgag ctcagcaaag   1440
tttttcgtca taagcttgct gaaactctgc aacacgcgca ggaacattat cctgagttgt   1500
tgcaagatag agcttggcta gaaaagcttc acgtagctgc agagggtgtt tttgaagtag   1560
catgttctga cctttggttg acaaatgtga cagtttcgga ctttcagcgt gtcggtgagc   1620
ccctatcctt tagaggtggc aagaaagtcc aaaaggttct tgacaacgtt ggaaaaacta   1680
tggttctcaa agagtttcaa cttgggcatc ctagtcaatc gaaaactttc taccagcagg   1740
ttgccaatct gggcaaagtg gtgtcccagc acgtaatacg tatcactggt gcttttgtgg   1800
acatgacaca tggagagtca cgtggttgta tcgtcatgcc tttctacgag caaggtgacc   1860
ttgccaagtg gattgagagt catcctaacg aaggcaaaga agcacgtgac cgacttgctg   1920
tgggtctgct tgtcggtgtg gcggatttac atgcccactg cattgtgcat tgtgacatca   1980
aaccagaaaa cattttcctc acaagcaacg gaacaccatt gatcggtgac tttgacggca   2040
tcaaggttgt aaactacact gcaacataca catcacttca ggcaacgcca cggtacattg   2100
cccctgagtt gcagaatggg cctgtacata ggtttgaaac agcaatggac atgtactctg   2160
tgggcataag cttaaaagag ctgtatccca ctgaacggac tgctgcaatg cagacactta   2220
tcgaagctct taccgcgaga gacccaagtc aacgtccaag cgctcgtcaa gcactccaac   2280
atcaagcttt tggagctcca caaatccctc tcatggaatg tcttgtatgt ttcgagaagc   2340
atcggctttc tgagggcacg agctgcgagg agggggactt cctttgcaga ggctgtatcg   2400
aatctgcagt agaagcagcg gcacaaccac ttgctaacgt cagagtggat gctgatggaa   2460
cgatggcatg catgaaacct gaatgtagtg gaaaaatatc aggtcaagaa atcacccgtc   2520
ttgcaccaac tgccttgaat catcttttgt tgattgcgaa gatgaaggca gaaagtgagg   2580
cagcagtttg ggctgagaaa gagatccaaa ggcgcatagc ggaagttgta cgtgcagaag   2640
```

```
aacaaaatag tgacgcacgg tggcatttac tgcatattca agagaacatc ttgagcacat   2700

gttgcccgaa ctgtaaggct tatgtacacg actttgacgg ttgctgcgct gtaaaatgtg   2760

gtaataatgc ttgtggacac ctcttctgcg cttggtgtct tgggtatagt tctcaggatg   2820

gagatgtttg ccatgctcat gtgagaacct gttcaagaag acttgggcaa gatctatatt   2880

tccctggttc actcgagcag gtttgtgaag cgtggcggtt gctccgcgca gaacgtctgc   2940

gtgagtactg gaatgcacaa attcaggata gaaatcttcg actcgttctg aaagacttat   3000

tgtcaccttt gctaacacca gatattgttg gcgcagattt tagattggaa taattaaaaa   3060

taaacgaatc tctgcaactc taaatctggc gatttgtttc catttcttta cacctccttg   3120

caaccaattt atatttttgg acatctgatc gctgctccaa tctaccatca gagagcctgg   3180

gatacgcaac ttcctcgcac acgctcccat caatctttgg acactacgac acgaaggttg   3240

tggagttttg cgcttttcta attttgcaca aggacttcat taaacgtaga gaccagtgta   3300

gtatcacaga cacaacactt tctccgaaat cgttacgtac tctttaacag gttattgcat   3360

attagcttgt gtagtagagt gtacataggt agtctgacaa gaaaatggcg aactcagatg   3420

aagtaatgaa gtgaagcctg tcgacgaagg tgaaagtaaa aaggatgaga cttggttctt   3480

gatgttctag gatgaatgta ccatgttgag gcaaagagtg tcgggctgta gagttaggtt   3540

agtttaaatt gaggtagggt aaggcaccta gctgaacatt acttcgaaat aggatataat   3600

ctttgtttta gtctatgtaa tattacacaa tagaacaaat atataagtag caagctctga   3660

ccaaaagctt ttgcattcca accactgtag gacgctgtaa tgagtctgcc aggttcttct   3720

gcttatttat accctcacaa agtggtttcc tccttcactt tcttaagcca tatattcaga   3780

tctactacta gcaataaatc gacggactct tatacagaga gccatatatt tgccacaagt   3840

tgacccaacc aatctccaaa aggcaaaagg ctacagctct gcaatttatt attcaaagtg   3900

cttgtagaat caaacagagc aacgacacgc aaagtgatga ggagaattca accatgcata   3960

cgtgcttgct caaaacgtac accaagattt ctgatcctgt attgatccgc aatgcctgtg   4020

caagagaaca tccgccgctc gaagtaattc tattgttatt caagctgcaa tacgataaat   4080

aggttagcaa atagtttgcg                                               4100
```

<210> SEQ ID NO 4
<211> LENGTH: 6200
<212> TYPE: DNA
<213> ORGANISM: Schizoochytrium limacinum

<400> SEQUENCE: 4

```
ctgctgctac ttcaacatca ctttgctcgt ttgtttacgt ctttttgttc acctcagaga     60

tttgacggat agagcgaacg tgcgtttcgc taatgtggtg cggcttgcca aggaagtctc    120

ggacttgcgc gcggaccgag gcggggtcag agaaaactcc ctgcagactg ggattgcctt    180

gcttgaggaa ttcgtagggc cggcgattca ggactacctt gcccaagtga agttgcgaca    240

ggtttccgct gacatcaaga actccaaaga gagtcttgac gcactacaag gccagattcg    300

tgcaagctct gcaaatgact tgcccagcct catcgaaaag cggaacgccg aacggaggca    360

cctgcattca cttttgcagg tcgtgtaccc atgggttcgt gcaaaccttt gcgaaagtga    420

tgaggatgta gtgcgcgaat tcaaagtgag agttgaaagt actattttta aatatcaatc    480

ttgcaccagt cactgaagag acaagcgcag atggtttcca acagtgccga gaactcgttg    540

tgcaggctgc caggtgcgtc gaagaataca agaagaacgg agaaaacaga ccaaacaacg    600

ttggcgagca aagccaacaa gctgaaaaac gcgccctctc tcaattgtct gatctagaac    660
```

```
ttggtgataa attatcgggt cccaagagca tgacacctga gcaggccatg aagctagaac    720
ccgaattatc taaactggag agtgctctcc aggaagagct cgaagttcta caaggagata    780
cacttagtgg cccattgtcc agaatacttt gcgcgataag ttcaacattt gttcgtttgg    840
aaaataactc tgcaagtgct gtgttgaatg gagcgagcaa gtgcacgcca caagagatct    900
ctgaactgca tgactatgta gtactgggtc taggaaagcc aagtacctca gatgttgagg    960
agctatacca gaaacttgac aagtcgagga aagccacaga aagtctaaag aaagccaaag   1020
aacttgaaac agaggacttg gacgaggagg ttcgagcata ttttagggat cgaatcaatg   1080
aacaagagct cattctctct caaggcaatc ctatcgagct tagcaaagcc tttcgtcata   1140
agcttgctga aactctgcaa catgcgcagg aacattatcc tgagctactg caagatagag   1200
cctggctgaa aaggcttcac ataagcgcag agggtgtttt tgaagtagct tgttctgatc   1260
tttggctggc gaacgtcgag atttcagact tcaagcctgt tggagaactc ctagcttcca   1320
gaggaggtaa gactgtccag aaggttcttg atggagatgg cagaactcta gttctcaaac   1380
agtttcagct tgggcataca agtcaatcca aaaccttcta caaacaagtt gccaatctgg   1440
gcaaagttgt ttctcagaac gtgatccgta tcactggtgc ttttgtggac atgactcatg   1500
gagcaccgcg tggctgtatt gtcatgcctt tctacgagca aggtgacctt gccaagtgga   1560
ttgagtctca tcctaacgaa ggcaaagcag cgcgcgaccg acttgctatg ggcctgctca   1620
tcggtatggc ggatttacat acccatggca ttgtgcattg tgacatcaaa ccagaaaaca   1680
ttttcctcac aagcaacggg acaccattaa tcggcgattt tgacggaatt aaggttgcag   1740
actacactgc aacgtacaca tcacttcaag taacgccaaa gtatcttgcc cccgagttgc   1800
agaatgggcc tgtttataag tttgaaacag cgatggacat gtattccgtg ggtgtaagct   1860
taaaggagct gtatcacact gaacggactg ctgcgatgca gacacttatc gatgctctta   1920
ccgcaacaga tcctggtcag cgtccaaccg cgcgccaagc actccaacat gaagcttttg   1980
gagctcctaa gatccctgtc aagatatgtc tagtatgcat ggaggagtat cagctttccg   2040
aaggcacgag ctgcgaggag ggagacttcc tttgtagaga ctgtatcgaa tctgcagtag   2100
aagcggcggc acagccacta gctaacgtaa gagtcgatgc tgatggaacg atggagtgca   2160
tgaaacctga atgtgttgga agaaatatcag gtcaagaaat cactcgtctt gcaccaagtg   2220
ctttaaatca tcttttgttg attgcgaaga cgaaggcaga aattgaagca gcagtttggg   2280
ctgagcaaga gatccaaagg cgcatagcag aagctttgcg tgcagatgga cagaatcgcg   2340
acgcacagcg gcatttactt catattcaag agaagatctt gagcacatgt tgtccgaact   2400
gcaaggcata tgtacacgat tttgacggtt gttgcgctgt agagtgtggt aatgatggtt   2460
gtggtcatag tttctgcgct tggtgtcttg agtttagttc tcaggattca caagcttgtc   2520
atgctcatgt gctagtctgc tcaagaaatc ttagcaataa taagtcatat ttcgctgagt   2580
cattcgagca ggttcgtgag gcgtggcagt tgttacgcgc agaacgccta cacgagtact   2640
ggaatgcgaa tattcaagat gaaaatcttg gacatgctct cgaacagcag cttgtgccgc   2700
tgctaacgcc agacatcgtt ggcccagagt ttaaactgtg aaaactttta aaaaatgatt   2760
ttagtaacta agctttaggt gcattgtgct ttttgtgtag atgcctaggc ttgggtaaga   2820
gcaaggtttg atctttcttg cttaaaatga aatttgctac taccaagcgt tacaatagct   2880
caatattgtc atgcacaaat cctacttact atgatacaag tttagagaca aatatcagaa   2940
atttactgat attgtgaaaa gcttcattct acctgtcacg aattgtttgt gtgtctaaag   3000
```

-continued

```
tatcgtggta aaagtagaag cagactattc tctcgcttct ttaaatgttc ttagaagcac   3060
aacatctctg gctttaggat gcacttctgt ggtatctgct gatcaaattc taagcgaaac   3120
tgtctttgat cacattttaa ttcatgaata ttgaactcaa ggcctcagcc tctagtttta   3180
gtctttccta aggacacttc gtcggcgttg gcctccccgg gatctgcttc gccataggac   3240
ctaaactgtg cagcatcgag gatgttctgc caagtcacta ctgtagtatc tccgccacgg   3300
ttcccaccac taccactact accaccacca ccgctatcgt ccgaggtgta ggcttcgtcg   3360
ctgccacctt cgtactcact attgccgagc aaccgtccac gaccgtcgca ataggctttg   3420
tccttcttca accacttgct tacgttttgc atgcaccagt ccgagttttt caatacctca   3480
acgaatctgg aaagaaaaat tggtttgatg agccaacaca agaaatgatc gagttcctct   3540
taagtgaaaa cgaagcaatc ctcgccgaag gtcgcgccga aggtcgcgcc aaagttctcg   3600
ccgagttcat tgaacccctc ttggcggggc ttagaaagcc cctgtttctc aaagttacgc   3660
ttcgtgttca tgcatcaact gctgcgacac cttcggcatg ggtcttgag ttcatatccc    3720
tcaagctatg gcggggtttt acaagtgaaa ttataaaccc gtttctcagt gcaaatttac   3780
tcaacatgca aatacgcaat acttcgtttc gaacctcgct ctatccacta aacattagcg   3840
gaaacaccaa tgcaatggct agtttgttta ataattggtg ctgcaggcca tttgttggac   3900
ttcacactga ggttgcaaat tttcctaaag tcatcgtacg catagaagac gatatcggcc   3960
tttcagccaa gcctgatctc accttggtca aaattgatga tcaaagaaat gagactgtct   4020
tctctattgt tgaagttaaa catcctaatc attttttgcc cttgtctgag aaccccaatt   4080
ggaccgacag gcgaaacgcc gctgcagctg cgggaattgc tatttttaca tctagaggcc   4140
aaccgagaca agctcttgaa caattacatg gtaatatgct tatccacggg gttaaatacg   4200
caattctgac atcagtagaa ctcacttatt ttgttaagcg ggataacaag ggtaacatgc   4260
ggatcacccg tggtttctac ggtgctgaaa ctgggggcgc aagagtaata agcaccaacg   4320
aggcaatggc tgcttttata tatattgcgt ccagggatcc tgacaatgga aagtttagac   4380
caagatcaaa tagcacgagc acagaaatca gggcttattc tgaacgtatc cagacaaaat   4440
ttggtggtcg ttcgataagt gatagagcca cagagaagtt caaagatagg gtgggcgaaa   4500
cagccttaca attcatgaaa ggtctaaacc aactcgcagt aaatatagag gagctacgca   4560
gcaatcttat tgaagtttta cctttcaagg atgaagctta ccttttcatg ccgctgccat   4620
ggtccaaaga ctaccgactt gtcacaagtt atgtggttcg gattccctgg gtttcaaaca   4680
aagacttcaa ctgggatatc tttgtgaaga ccatggcggt ctctaaagac tgggcgagag   4740
agacatatga gttcgaaaaa tccttctttc tcaacgaagt taagctgtac cttggccccc   4800
tgcgcctgct ccaaggtaaa cacgcgccct ttttggtgta cggcggcaca tttcataaac   4860
gaatcatcat tgccacaacc ttctctgggg agaccgcaac aaaagaactt attcttgcta   4920
acagtagctg ggcaattaca gccattcgag catcactttc cgcgctgcac caggtcggtg   4980
tgctccatgg cgacatcgcg ctgcgtaata tcgccatcga caccactacc aagaccgccc   5040
acttgatcga ttttggccgc tcctcacaag acaaaaccac caagaaaaac agggacacag   5100
aaatgaaaga actgaacaca cttctggggt ttgctattca tcgcaagcga atccgagact   5160
cctaactgaa cacacttctg ggtttgcta ttcatcgcaa gcgaatccga gactccttta    5220
aatagccaag acgacagaat acagaatcaa atgaccttct gaacgagtaa acaaatatat   5280
atattttttt taagactaca aatttcttac accaaaatca gcaaagaagg tcttctactg   5340
aaaaaagtgc ctgacgttgc aggatttaat ccaagaaaga ccggtagcat tttgggatct   5400
```

```
cttagacgag atatgatttt gtctaaccca acataaaata ctacttaagt ttttttataa   5460

tcggttgata gggaagtagc caagcacatg acccaaaaga aagttaaaag caaggtttcg   5520

cctcatcagt ggctggaatt tctttagttg ctcttggggg ttgacacttt tgtcccttgt   5580

ttcatctttt gcagtgatgt ttgcttcaga agttccccaa ttatttccat ctcctagtac   5640

tacataatgt agtgcggcta ctactggtac ctttatggat aggtaggtaa tttttagtca   5700

attcaatgag gtttggcgcg catcaaaatt tatgctgacg cttcttaata tatatgattc   5760

aatgtgaagt ggggaaatgc gggtaaatga tctgctaaaa tccaatagag tggaactttt   5820

ctagataggc ctaatttatt attgagtatt agccactctg aataaacatc cgaggataga   5880

taagagcttg gaagaaaacg taagaaatga agaaaatcaa ttcatgaacc tgaccgaatg   5940

ggactgactt aggaaataat aatcatttcg ctaatcctgc agatgctgaa gaatgaatgg   6000

aaaaagatga cctccaggtc tgtgaaagta atgttgttgt tgatatcaga cactcattta   6060

catcttcagg gcggaacata atttcaacga atgatcatcg cagcaagaga taaacaatca   6120

caaagagttc tttaatgcat ggcctccgtt gtactccaaa gtatgcgatg catcctcgac   6180

caatttaata aacttacagt                                                6200


<210> SEQ ID NO 5
<211> LENGTH: 4500
<212> TYPE: DNA
<213> ORGANISM: Schizoochytrium limacinum

<400> SEQUENCE: 5

accgtgggcc aagctggccg ccccaagacg atcactggct tccagactca ctcgactcct     60

gtgctcatga gctttggcga ccgtgctgag ctcgtctctg atgactacga accattgaca    120

agcgtcttgg agggcgttgt tcttctcaag aagaagaaga agcgttcctc caaggatcgt    180

gatggtgatg tggaaatggc aaaataaata attcagactt gcattatctt aaaaaaaaac    240

aaagtgcagc ggtaacaacg actctgttgt tgcgtctact tctaccccga cttattcttt    300

aagaagttcg ttcatagaaa ggctggggtg tgagagagag agcatgtttt ttaactcaac    360

atggataagt aaaaaaaagg ccaggaacat caaggagaag cttcaaatga ctgttaggta    420

gctgttgtag ctccttagca tattcttctt cttactactt aacatctctg ctttcggccc    480

caaatcgctc gcttgcttgt tcgctcgtcc cgatagacgc ttctcattcc tatagcattc    540

tctaaaaaaa taatctaaac attacacctc tcaaaataga aaatctatct tccacacgtt    600

gatctaaatt ctccggcttt tgtatctttg tatcacagtc ctgccaacat tcagcatgtt    660

cactcagccc cgcggattgg tctctctctc cctaaggctg agcctgagca gatctaaacg    720

gacgtcgtga attcatcata tcattgctaa taatttaccg taagttaagc actagaaccc    780

tcttattgtg cctcatatca ttgtaacggg cttggggact catagaggtt gtccgggtaa    840

tgcggggaat atagcgacct aacgaccgct ttaacaaagg gaaataatta ggcagtacgt    900

aaagagtact actggtacct agttatgtaa caaggtaatg aattgtcaat gattcaatgc    960

ttggtaagtt tgttcaagtt cgttccgaag cgaagcaaac tcgtgcaagc ggggtcgcgg   1020

agacgagctc gtcccgcgga cgtacgcacg caggaggttg ggaaggtggt caagtaaagg   1080

ttttgacagc aagatgctct ggccggcaga acacctgcat gaaacctacg agcacattcg   1140

taacgatgcc cttggtagtg ggtgctcagt tgtgatttat gtggcgcttg actgcgatgc   1200

gctatgcgct gtgaagatct tgacaagttt gttgaaagcg gataatgtag cgtataagct   1260
```

```
gagacccgtt cgaggatata gtgatatttt agaggatttc cgcgagacat caaaggcaga   1320
agcgattaag tccatcatta tgatcaactg cggtggtgat gtcaatgcac aggaaatgtt   1380
taacttggac gacggcatga catgctatat cattgactcg gcgaggccct acaatcatgc   1440
aaacctactc cggtctcata tgcacacgat tgtgtttgca gatgacttca tgaaggagga   1500
agatctcgtt aaggaggcag aactgctcga gcacctggat gaggataacg tagatgaact   1560
cctgggatcg aacgacaacg acgatgacga cgatgacgac gatgacgacg atagcgatga   1620
tggtaaagga gaggtcgagg acgggaatga tgcaaactct gctcgtaacg ggcaagaagg   1680
agagattgat tccgacgaag aacacgaatt cgatggaggt aaccctcagc agaatgcctc   1740
agatagtgat gacgatgaaa atgaagatgc caataagcag actagcaaca acacaaacaa   1800
taagacaagc aaagcaaagt ctgcatctca acttctgaca gagcaagagg aggcagagat   1860
cgagcgtgag cttgctgcag aaaatggcac ccgaaagaag cggaggcgga cttcttcctc   1920
ctcatcctct tcacaaaacg acaaaaacaa cgatagtggc gatgatgatg atgatgatga   1980
tgatgacgat gataaggatg atgatagtct tcctaaacgg aaggtccgtg aaaaggttga   2040
cgctgaggaa cccatggatg acaaagcacg tgtagcaaag tactacgctg ggtcattccg   2100
gggtacatcg gcagcacatg tcctgttttc cctctcacag cgtctcaaca aagatcaaaa   2160
gatttttctt tggcttgcca tcgttgggac tactcaccac ttcatcaatt ctgaactcag   2220
cgaggaggac taccttctcc gtgtactcac ataccaggat ctcgttaaag accgctccat   2280
gtctcgtcga gcaggccaac atacagtcac agaagatggt gctgaggtgc ctcttatgga   2340
aggccaaagc atggaattca ttgaagaact tcgtcttatg ctgcatcgcc actggtcgtt   2400
gcacgaggcg tttctgtact ctgactacat tgctgccaag cttggaatct ggaaaaatga   2460
cggtgaagcc aagcttcgca catttttcgc caagatggga attagtcgga aagaagcaga   2520
gcaaaagtat tctttcatga acatgagtgt taagagggct ctcaaagata aaattggtgc   2580
tcatggagcg gacttttctc ttgacgaaag cttcgtctac gcatcattcc agttccgggc   2640
tggctttggg caccaactat cagctgctga taccgcatac tgtatggctg ctttgctcga   2700
gagtgcagct acacacccta cagtttttgc cgatgattct ggtgctgatg ctacagagga   2760
tgctactgaa atccccgagg ttgaccttga cggggacgac cttgattatg ctggtgaaga   2820
tggagcaaat gggcaaaagg aaaatagcaa ggcaattctg gcagcttcac tttggaaaca   2880
aagcttcaat gcagcttatg atgctctctc tttctcacaa acaactcgca accagcatct   2940
cctggaacaa ggccttaacc tcgccaaagc tctgcaaaag gctattattc aggagggtgg   3000
aaatataatt tcaggaacaa agattgccag tgcaggttct tttcgctact gtattctgga   3060
aggtttgcca cccaagctgg tgagtatttt ttcccagcct gatacacttc tccgccttgc   3120
caaattcatc atgctcgcgt acacaagtgc cggcaagtgg tcgggcctgg gcgccaaacc   3180
ccttgttctt ggtgtcaaaa acctcaagac aaacaaagct cattttgttg gcctccccca   3240
cccaactttt ggagatgacg cgattgcaaa gaaccccttt ggcagatatt ttcgtgtggc   3300
cgcccaaaaa gtgggcacgg cccacatcca tgttggcttt agctcggcat gtatcgagat   3360
ccccctcgag cttgtgcaga aattcttagt ggcattgcat gaaataacag cttgaataaa   3420
tggttgatta tatgctttaa ggttcctttt cctctttgtt cccattgctt ttacctctgt   3480
tgatacaagt ggcctcacac tacaattgaa gagccattgg ataagttcga ttattaatta   3540
gagaatgagt ttccactctc aattctttct attaggcagt gttgattatt acatgagcat   3600
acgtgcatca tcgtcattat atcggcaaat acgaatatct agatgtgcta accgaaagag   3660
```

```
ttccaagatt acagtgatat tgttggaagc atatatatga attaatatgc tgcagaatct   3720

ttgaacccgc cgggtgtgtt atcgttctat tggaactggc agtggccctg atgttggcta   3780

ttaagtaggg gagaaggttt ctactggaag tgaatgcatc gctctctaag agcgcgcact   3840

tcaaatgtta cttccgattt cagcgttgtt tgctaggttc tcattatgcg tttatactcg   3900

cttttgagct cttgaggatg accataccga gctacgggct gcacttgtgc tgtcaagagg   3960

ctcaaaatcg ggtctggttt cacggtaatc gaggtcgtga agaagatagc ggtatagttg   4020

atcgcgcatt gcttgattct tgtagttatt gtctgcaaat tgcatttgca tcgcaaaggt   4080

ccgctctaga ttctgaacag catgttgcgt cattccaggg atgaaaacaa tttcaccttc   4140

tttctgtacg cagtgaagaa caacagaatc atcttcaagc tcttcggtta ctttctttgc   4200

cttaattttg cttgcaaacg cgcctgcgcc aaacttactt tgaagttcgg cgtttttctc   4260

aagcttgggg agtttctctc caggcttcgc tttcgattta aacttcttga tcaagtacgt   4320

ctgctcttca tgagccttac agacagggtc gtgatccaga aatctcgagc agtatgtctc   4380

ctctagactt ggtgcgggct caagaagctc tacctcatct tgggcttcca actcagaata   4440

tccagcaacc acgcggttag ataccttcat ataccagacc ttcttaccct caaagataag   4500
```

<210> SEQ ID NO 6
<211> LENGTH: 11100
<212> TYPE: DNA
<213> ORGANISM: Schizoochytrium limacinum

<400> SEQUENCE: 6

```
cattgattga ttgcagatga tcttgggcaa cgcgcgtcag cttgagcgag gaatgctttg     60

gacttcaggt tcttcgcttc tgtgtttcat tctttctcga agaaagaaag aatgaaagaa    120

agagagaaag aaagaaagaa agaaagaaag aaagaaagaa agaaagaatg aatgaatgaa    180

agaaagagag aaagaaagaa cgaatgaaag aaagagagaa agaatcaaag agaaagcgca    240

ttcgcagttc ttcttcgtga aagaaaagga aaagagaggc gatggtaggc tctgatctca    300

tcatttctgg tttctctgtt gtacctgtac tctgtgcttg tggccttgcg aaggctgaag    360

acgccatgca gacaaccacg cctccgcaga gactttgcgg gaaagcagag ggcttctcgc    420

cactctcgaa gaaacgagct cgccagtttt cggggttgtt ctcagaattg cgagtgttgg    480

ctttatatgg gatgatggta tggcacttcg tcatcgttac tctcgctcgc ttgcttacga    540

agattttcaa aagggcgaaa gaagtgctca gcttttaaaa taaagtcaca ccaaagacta    600

ggccgcatag cagaaagcta aagtaaaccc aatctgtctg aagagagtgt cgtggttaga    660

tacttacgca agagtttaaa agctgtaaat agtacaggaa caaaaacaaa taaatatata    720

tatattcttt tttattagta aaacatgaaa ccaaaaaact cctttaaaat aaaataaaat    780

aaaataaaat aaaataaaat aaaataaatt tactactata tatacatata tatatacaat    840

aaataaaaac aactttttca gaccagaaaa agactgagaa aaaaggaaac taatgactct    900

cgagcaccga gagcgatata agagtggatt atatttgcta ggcccaccac gagtgagtcc    960

cctaggagga agcgccctct gagacaggag cagaggcgtc gctggtgctc caaaaagcga   1020

cggcgaatgg aaagcaaaac cctttcgagg gaggcttgtg gccgtgacta ttcaaatctc   1080

cagcatctca gctccagcac agcagaagct acctcgcttc tcagctctag ctatcacatc   1140

gatcgcagca tctagctcgt agacagctag cgccgcacct tcccccaaat caacttgggc   1200

aacttaactc ttttttcacc agaactcctc ttttccttta atcttcgaaa agaagacgaa   1260
```

-continued

```
taaaagagat aatcctctgc cgcagcacat tctaaaagaa aagcggcata ctggcgtagg   1320
caagactttc aagctcttcc tcgcctccac cccgtatttc cctgttcatc tttgtgaaac   1380
gaggaaacaa gaaattttat aggacaagat ggctcaacgt gagaaccgtc tcgaggccaa   1440
catggatacc cgcatcgctg tgatcggcat gtccgccatc ctcccctgcg gtaccaccgt   1500
tcgtgagtct tgggaggcta tccgcgatgg tatcgactgc ctcagtgatc tccccgagga   1560
ccgcgtcgat gtgaccgcct acttcgaccc ggtcaagacc accaaggata agatctactg   1620
caaacgtggt ggattcatcc ctgagtacga cttcgacgcc cgtgagttcg gcctcaacat   1680
gtttcagatg gaggactccg acgcaaacca aaccgtcacc ctcctcaagg tcaaggaggc   1740
cctcgaggac gctggcatcg aagccctcag caaggaaaag aagaacattg gatgtgttct   1800
cggtatcggt ggtggccaga agtccagcca cgagttctac tcccgcttaa actatgttgt   1860
cgttgagaag gtccttcgca agatgggcat gcctgaggag gatgttcaag ctgctgttga   1920
gaagtacaag gccaacttcc ctgagtggcg ccttgactcc ttccccggtt tcctcggcaa   1980
cgttactgcc ggtcgctgta ccaacacctt caacctcgat ggtatgaact gtgtcgtcga   2040
tgctgcctgt gctagttctc tcatcgccgt taaggttgcc attgatgagc ttctccacgg   2100
agactgtgac atgatgatca ctggtgctac ctgcacggat aactccatcg gtatgtacat   2160
ggccttctcc aagaccccgg tgttctctac cgaccctagc gtccgcgcat acgatgagaa   2220
gaccaagggt atgcttattg gcgaaggctc tgccatgctt gtgcttaaac gttacgccga   2280
cgctgttcgt gatggtgacg agattcacgc tgtcattcgc ggctgcgcct cttcctctga   2340
cggtaaggcc tccggtattt acaccccgac catctctggt caagaggagg ctcttcgccg   2400
tgcctacatg cgcgctaacg tcgatcccgc caccgtcact cttgttgagg gccacggtac   2460
cggtaccccc gttggtgacc gtattgagct caccgctctc cgtaacctct tcgacagtgc   2520
ctacggcaac gagaaggaga aggtcgctgt tggcagcatt aagtccaaca tcggtcacct   2580
caaggctgtc gccggtcttg ccggtatgat caaggtcatc atggccctca agcataagac   2640
tcttccggcc accatcaacg ttgatgagcc ccctaagctt tacgacaaca ctcccatcac   2700
cgactcatcg ctgtacatta acacgatgaa ccgtccgtgg ttccctgctc cgggtgtgcc   2760
ccgtcgcgct ggtatctcca gtttcggttt tggtggtgcc aactaccacg ccgttcttga   2820
ggaagccgag cccgagcacc agaaggctta ccgtctcaac aaacgccccc agccggtgct   2880
tctgatggca tcttcaaccc aggctcttgc ttccctctgt gaagcccagc ttaaggaatt   2940
cgagaaggct atcgaggaga acaagaccgt caagaacact gcttacatca agtgcgtcga   3000
cttctgtgag aagttcaagt tccctggatc tatcccgagc tctaacgctc gcctcggttt   3060
tcttgtcaag gaggccgatg atgccaccga gaccctccgt gccatcgttg cccagttcca   3120
aaagtcagct ggcaaggatt cttggcacct tccccgccag ggtgtgagct ttcgtgctca   3180
gggcatcaac accactggtg gtgtcgctgc cctcttctct ggccagggtg ctcagtacac   3240
ccacatgttc agcgaggtcg ccatgaactg gcctcagttc cgtgagagca tctctgacat   3300
ggatcgtgcc caggctaagg ttgctggcgc tgacaaggac tacgagcgtg tctcccaagt   3360
cctctacccg cgtaagcctt ataactctga gcccgagcag gaccacaaga agatctccct   3420
gacctcatac tctcagccct ctaccctcgc ctgcgctctt ggtgcctacg agatcttcaa   3480
gcaggctggt ttcaagcccg acttcgctgc cggtcactct ctcggtgagt ttgcggccct   3540
ctacgctgct gactgcgtca accgtgacga cctctttgag ctcgtgtgcc gtcgtgcccg   3600
catcatgggt ggcaaggatg cacctgctac ccccaaggga tgcatggctg ctgtcattgg   3660
```

```
acccaatgcc gagaagatcc agattcgcac tgctgatgtc tggctcggca actgcaactc   3720
cccttcgcag actgtcatca ccggctctgt tgagggtatc aagaaggagt ccgagcttct   3780
ccagagtgag ggcttccgtg ttgtcccccct cgcctgcgag agtgccttcc actcaccgca   3840
gatgcaaaac gcctcctctg ccttcaagga tgttctctcc aaggttgcct tccgtcagcc   3900
tagcgcccag accaagctct tcagcaacgt gtctggcgag acctactcca acaatgccca   3960
ggacctcctt aaggagcaca tgaccagcag tgttaagttc atctctcagg ttcgcaacat   4020
gcactctgct ggtgctcgca tctttgtcga gtttggcccc aagcaggtgc tctctaagct   4080
tgtttccgag accctcaagg acgatccttc cattatcact atctctgtca acccttcctc   4140
tggcaaggat gccgatattc agcttcgcga ggctgctgtg cagctcgttg ttgctggagt   4200
caaccttcag ggcttcgaca agtgggacgc acctgacgcc acccgccttc agccgattaa   4260
gaagaagaag actactcttc gtctctcggc tgccacttac gtgtctgaca agaccaagaa   4320
ggctcgcgag gctgccatga acgacggccg catgctcagc tgtgtcagca aggtcatcgc   4380
ccccccctgac gccaagccca ttgtggacac caaggctcag gaggaggttg ctcgtctcca   4440
gaagcagctt caggatgccc aggcccagat ccagaaggcc aaggccgatg ctgctgaggc   4500
tgacaagaag cttgccgctg ctaaggatga ggccaagcgt gccgccgctt ctgcacctgt   4560
gcagaagcag gttgacacca ccattgttga taagcaccgt gctatcctca agtctatgct   4620
tgctgagctt gactgctact ccactcctgg tgctgtgtcc agctctttcc aggcacctgt   4680
tgctgctacc cctgctccgg tcgctgcgcc tgttgcagct gctcctgctc cggctgtcaa   4740
caatgctctc cttgccaagg ctgagtctgt tgtcatggag gttcttgccg ccaagactgg   4800
ttacgagact gacatgatcg agcccgacat ggagctcgag actgagctcg gcattgactc   4860
tatcaagcgt gtcgagattc tctctgaggt ccaggcccag ctcaacgttg aggccaagga   4920
tgttgatgct cttagccgca cccgcaccgt tggtgaggtt gtcaacgcca tgaaggctga   4980
gatcgctggc agctctggtg ctgccgctgc tgccccggcc cctgttgctg ctgctcccgc   5040
tgcccctgcc cctgctgtca acagcgctct tcttgccaag gctgagactg ttgtcatgga   5100
ggttcttgcc gccaagactg gttacgagac tgacatgatt gagcccgaca tggagctcga   5160
gactgagctc ggcattgact ccatcaagcg tgtcgagatt ctctctgagg ttcaggccca   5220
gctcaacgtt gaggccaagg atgttgatgc tcttagccgc acccgcaccg ttggtgaggt   5280
tgtcaacgcc atgaaggctg agatcgctgg cagctctggt gctgccgctg ctgccccggc   5340
ccctgttgct gctgctccgg cgcccgtcgc tgccgctgcc cctgctgtca gcagcgctct   5400
ccttgagaag gctgagtctg ttgtcatgga ggttcttgcc gccaagactg gttacgagac   5460
tgacatgatt gaggccgaca tggagctcga gactgagctc ggcattgact ccatcaagcg   5520
tgtcgagatt ctctctgagg tccaggccca gctcaacgtc gaggccaagg atgtcgatgc   5580
tcttagccgc acccgcaccg ttggtgaggt tgtcaacgcc atgaaggctg agatcgctgg   5640
cagctctggt gctgctgccc cggccccggt cgctgcggcc cctgctccgg tcgctgccgc   5700
tgcccctgct gtcaacagcg ctcttcttga gaaggctgag actgttgtca tggaggttct   5760
tgccgccaag actggttacg agactgacat gatcgagccc gacatggagc tcgagactga   5820
gctcggcatt gactctatca agcgtgtcga gattctctct gaggtccagg cccagctcaa   5880
cgttgaggcc aaggatgttg atgctcttag ccgcacccgc accgttggtg aggttgtcaa   5940
cgccatgaag gctgagatcg ctggcagctc tggtgctgcc gctgctgccc cggccccggt   6000
```

-continued

```
tgctgctgct cccgctcccg tcgctgcccc tgctgtcagc agcgctctcc ttgagaaggc   6060

tgagtctgtc gtcatggagg ttcttgccgc caagactggt tacgagactg acatgattga   6120

ggccgacatg gagctcgaga ctgagctcgg cattgactcc atcaagcgtg tcgagattct   6180

ctctgaggtc caggcccagc tcaacgttga ggccaaggat gtcgatgctc ttagccgcac   6240

ccgcaccgtt ggtgaggttg tcaacgccat gaaggctgag atcgctggca gctctggtgc   6300

tgccgctgct gccccggccc ctgttgctgc ctctcccgct cccgtcgctg ccgctgcccc   6360

tgctgtcagc agcgctctcc ttgagaaggc cgaatctgtt gtcatggagg ttctcgccgc   6420

caagactggt tacgagactg acatgattga ggctgacatg gagctcgaga ctgagctcgg   6480

cattgactct atcaagcgtg tcgagattct ctctgaggtc caggctatgc ttaacgttga   6540

ggccaaggat gttgatgctc ttagccgcac ccgcaccgtt ggtgaggttg tcaacgccat   6600

gaaggctgag atcgctggca gctctggtgc cgccgctgct gccccggccc cggttgctgc   6660

tgctccggcg cccgtcactg ccgctgcccc tgctgtcagc agcgctctcc ttgagaaggc   6720

cgaatctgtt gtcatggagg ttctcgccgc caagactggt tacgagactg acatgattga   6780

ggccgacatg gagctcgaga ctgagcttgg cattgactcc atcaagcgtg tcgagattct   6840

ctctgaggtc caggctatgc ttaacgtcga ggccaaggat gttgatgctc ttagccgcac   6900

ccgcaccgtt ggtgaggttg tcaacgccat gaaggctgag attgctagca gctctggtgc   6960

tgctgcccct gctccggctg ctgccgttgc accggcccct gctgctgccc ctgctgtcag   7020

cagcgctctc cttgagaagg ccgaatctgt tgtcatggag gttctcgccg ccaagactgg   7080

ttacgagact gacatgattg aggccgacat ggagctcgag actgagcttg gcattgactc   7140

catcaagcgt gtcgagattc tctctgaggt ccaggctatg cttaacgtcg aggccaagga   7200

tgttgatgct cttagccgca cccgcaccgt tggtgaggtt gtcaacgcca tgaaggctga   7260

gattgctagc agctctggtg ctgctgcccc tgctcctgct gctgccgctg caccggcccc   7320

tgctgctgcc cctgctgtca gcagcgctct tcttgagaag gctgagtctg ttgtcatgga   7380

ggttctcgcc gccaagactg gttacgagac tgacatgatt gaggccgaca tggagctcga   7440

gactgagctt ggcattgact ccatcaagcg tgtcgagatt ctctctgagg tccaggctat   7500

gcttaacgtt gaggccaagg atgttgatgc tcttagccgc acccgcaccg ttggtgaggt   7560

tgtcaacgcc atgaaggctg agattgctag cagctctggt gctgctgccc ctgctcctgc   7620

tgctgccgct gcaccggccc ctgctgctgc ccctgctgtc agcagcgctc ttcttgagaa   7680

ggctgagtct gttgtcatgg aggttctcgc cgccaagact ggttacgaga ctgacatgat   7740

tgaggccgac atggagctcg agactgagct tggcattgac tccatcaagc gtgtcgagat   7800

tctctctgag gtccaggcta tgcttaacgt tgaggccaag gatgttgatg ctcttagccg   7860

cacccgcacc gttggtgagg ttgtcaacgc catgaaggct gagatcgctg gcagctctgg   7920

tgctgctact gcctctgccc ctgctgctgc agctgccgcc cctgctatca agatctccac   7980

tgttcacggt gctgactgcg atgacctctc tgtgatgtct gctgagcttg tcgacattcg   8040

tcgcgctgat gagctccttc ttgagcgccc tgagaaccgc ccggtcctta ttgtcgatga   8100

tggtaccgag ctcacctctg ctctggttcg tgttcttggt gctggtgctg tagttcttac   8160

ctttgacggt cttcagttgg ctcagcgtgc tggtgctgct gttcgccatg tccaggtgaa   8220

ggacctctcc gctgagagtg ccgagaaggc tatcaaggag gctgagcaac gcttcggcca   8280

gcttggaggc ttcatctctc agcaggctga gcgctttgcc cctgctgaca ttcttggttt   8340

caccctcatg tgcgctaagt ttgccaaggc ttccctctgc acccctgtgc agggtggccg   8400
```

```
tgccttcttc attggtgtgg cccgtcttga cggtcgcctt ggtttcacct cccagggatc   8460
tactgactcc ctcacacgtg cccagcgtgg tgctatcttc ggcctctgca agaccattgg   8520
ccttgagtgg tctgctaacg aagtgttcgc ccgcggtatt gatattgctc gtgaggtcca   8580
ccctgaagat gctgccgtcg ccatcactcg cgaaatgtcc tgcgctgaca accgtatccg   8640
cgaggtcggc attggcctca accagaagcg ctgcaccatc cgtgctgtgg acctcaagcc   8700
gggtgccccc aagatccaga tcagccagga tgacgttctc cttgtgtctg gtggtgctcg   8760
tggtattact cctctctgca tccgtgagat cacccgtcag gtccgcggtg gtaagtacat   8820
tctcctcggt cgctccaagg tccctgctgg tgagcctgct tggtgcaacg gtgtttctga   8880
tgacgatctt ggcaaggctg ctatgcagga gctgaagcgt gctttctccg ccggtgaggg   8940
ccccaagccc accccgatga cccacaagaa gctcgttggc actattgctg gtgcccgtga   9000
ggttcgttcc tcaattgcta acattgaggc tctcggtggc aaggcaatct actcctcttg   9060
tgatgtgaac tctgctgctg atgtcgccaa ggctgttcgc gaggctgagg ctcagcttgg   9120
cgcccgtgta actggtgtcg tccacgcttc tggtgtcctt cgtgaccgcc tcattgagca   9180
gaagcgcccc gatgagtttg atgctgtctt cggcaccaag gtgactggtc tcgagaacct   9240
ctttggtgcc attgacatgg ccaaccttaa gcacctcgtc ctcttcagct ctcttgctgg   9300
tttccacggc aacattggtc agtctgacta cgccatggct aacgaggccc tcaacaagat   9360
gggtcttgag ctctctgacc gtgtgtccgt gaagtctatt tgcttcggcc cctgggatgg   9420
tggcatggtt accccccagc tcaagaagca gttccagtct atgggtgttc agatcatccc   9480
ccgtgagggt ggtgccgata ctgtggctcg cattgtcctc ggctcctccc ctgctgagat   9540
ccttgttggc aactggacca ctcccaccaa gaaggttggc agtgagcccg ttgtgatcca   9600
ccgcaagatc agcgctgcat ccaacccttt tcttaaggac cacgtcatcc agggtcgctg   9660
tgtgctcccc atgaccattg ctgtgggctg ccttgctgag acctgcctgg gtcagttccc   9720
tggatactcc ctctgggcta ttgaggatgc tcaactcttc aagggtgtca ccgttgacgg   9780
tgatgtcaac tgtgagatca ctctcaagcc ttcccagggt actgccggcc gcgttatgat   9840
tcaggccacc ctgaagacct tcgctagcgg caagcttgtt ccggcttacc gtgccgtgat   9900
cgttctctcc actcagggaa agccccctgc tgctactact tcccagaccc cctctctcca   9960
ggctgatcct gctgcccgtg gcaaccctta cgacggcaag accctcttcc acggccctgc  10020
cttccagggt cttaaggaga tcatctcttg caacaagtct cagcttgtcg ccgagtgcac  10080
cttcattccg tcttccgaga gcgctggtga gttcgcttct gactacgagt cccacaaccc  10140
tttcgtcaac gacattgctt tccaggccat gctcgtctgg attcgccgca ccctcggcca  10200
ggctgccctc cccaactcta tccagcgcat tgtgcagcac cgtgctcttc cccaggacaa  10260
gcccttctac ttgaccctca agagcaacag cgcgagtggc cactctcagc acaagacctc  10320
cgttcagttt cacaacgagc agggtgacct cttcgtggac atccaggctt ccgtcacctc  10380
ttctgactcc cttgccttct aaagttgtga ggctgtcttg tcttgtcagt cgcgaaagtg  10440
taagcaagaa ctttgtcata caaagaagca accaacttcc gaaccaacac accttgtagg  10500
attacaacca caactttcta taaatagtgc gcaagaataa ccagtaagct atccttcgtg  10560
tacctgttac aacaacgaca tttttacttg atcttcctac ttgtgatggg tagtcccggc  10620
ttgtactgac agtgatgcca cagcagagta gatcactgtg aataagtaaa taagcctact  10680
tattatattc ccaaagtact cgctgggata ttattagtat cacgaaaagt gatatgtttt  10740
```

-continued

```
ataactcgct tgtcttgcca agatctaacc tttttttttt aaatggccaa aaagtcgcca  10800

gaacacatct tacaataaac aaaaatttag attatatcgt atgtataatg tataatatat  10860

tatattatta tatacatacg atataatcta aagccattcc agacttattc ggtgatgaaa  10920

aatgctttcc cagctttata caaactattc aaaaagttgc atgacccatt ttcagatata  10980

tttaatagta taagattatg tccatttgtt ttcaaagtta ttcaagagtt tacatcttga  11040

agtttcatcc ctttactact acactgtttt tcgtttgggt tttttctcta acggcgaaag  11100


<210> SEQ ID NO 7
<211> LENGTH: 7767
<212> TYPE: DNA
<213> ORGANISM: Schizoochytrium limacinum

<400> SEQUENCE: 7

tattgctatt acttgaattt gaatttgaat ttgaattcag gtagacaata aaataagatt     60

agcaaaacat tttgagagga agcagaggat atgcagtgca aaaggaggtc ccgagtttcg    120

atcttctttg cacctgctac gtatctagtg cacgtagagc aagaaaagaat gaaagaaaga    180

acgaaagaaa gaaagagaga gagagagaga gagagagaga gaaagcgaag atgatagcgg    240

agagaactct tcttcgcagt cactctgttt ctcagtcagt cccgcaacca ataacaactc    300

gaactcgcag cagtgttctt cggagtgcca gcgctcgctc gcactgcgtc ggcacagcag    360

cagcagcagc aggccccgcg ctcgctgcac tcagcccggg caggagcaac agctgctgag    420

cagctgaggc cagctggctg gcggctcgcc tcgcctcgcc tcgcgtcgcg tcgcgagaga    480

aagcgatcga ccaactgtca atcgattatt cgagtccttc gagcgcttta tagggcactg    540

attgatcact cattgattca ttgactcatt tattctttgc gtggtcagcc aaacggcgtt    600

agcattgggc aaagcgggtc tttgctttgc tctaaaatag atttgctcgc gagagtacgt    660

acttgcagga gtaggtaggc tctgcctagt acctgggcat ttgaatattt gaacttcgaa    720

cttcgttgag tatctgaata tttgaatatc tgaatatttg aatttcgaaa gtttgaatat    780

ttgaatattt gaattttgga atattggaat agctgggttt ggagataaga cttactaagc    840

taagcgccga cgtaagagcg gcgagtaaat ccacacacaa gagagaggca gagagagagg    900

gagggagaca actcgcgcag gcaagctgag cccactggac gcacggggcg cgtccccccct   960

gacgggcgct ctggtggtgg cgtgtttggg agggttttgc atgcttgtga taggggctct   1020

ggcgcgggct ctgtacggtg cttggagatg cacgggcagg gcgagagagg ggacgggttc   1080

ccgggaggcg ctgcttggag gtgctgagag ggagggagaa ggcgtgcttt gcgatgcgcg   1140

gggcgaccta ggcgctgctg cgcggtgcag cagcagggac ctcggacgtg agtcgaagcc   1200

gtctgcagag gagatggtag aagggccgcg gattggtagc agagaagagg aaatagaaga   1260

agaagaagaa atagaagaag aagaaataga agaagaagaa atagaagaag aagaggagga   1320

cgggcaggcg ggaaagatgg agaaaggact cgcggcggga aaacaagaga atgtgaactt   1380

gggcttgaac tttggtttga atttgaatgt ggagaacgag gggttgaatt tgagtttgaa   1440

tttgaaagaa aacttacgga aagaaagttt agttgaaaaa agaaaaagag aaagaaaaag   1500

agaaagaaaa agagaaagaa aaagagaaag aaaaagagaa agaaaaagag aaagaaaaag   1560

agaaagaaaa agagaaagaa aaagaagaag aaaaagaaga agaaaaagag aaagaaaaag   1620

agaaagaaaa agagaaagaa aaagaagaag gagatttaaa aagttgttta gttgaaaaag   1680

gagaaggagg aagaagcagc gacagcggca gaagaagaag tagttgttgt aagaggggaa   1740

cggaggcagt agcagtggag caggcggagg cgacagcaaa cctcgaactc gaccccgtcg   1800
```

```
agccgcagca agaacaagag cccgaccagg tggacgagga cgaggtccgc ttgttgtcag   1860
gaacaacaga agttgcagga ctagccgaga gtgctaccac tgcaattctt agatccacag   1920
acgcaagagc agaaaactta caactgctcg ccacaacaca agaaccacct tcagatacaa   1980
ccaggttcga gaactccaca agtctagaag cagcaacagc tctagcagat aatcaaacag   2040
gtccagaaaa agctacgact agaagagaaa ttatcgagtc gcaacttgca accatggcca   2100
ctcgcgtgaa gaccaacaag aaaccatgct gggagatgac caaggaggag ctcaccagcg   2160
gcaagaacgt cgttttcgac tatgacgagc tccttgagtt cgccgagggt gacatcagca   2220
aggtcttcgg ccccgaattc agccagatcg accagtacaa gcgtcgcgtt cgtctccccg   2280
cccgcgagta cctcctcgtc acccgcgtca ccctcatgga cgccgaggtc aacaactacc   2340
gcgtcggtgc ccgcatggtc actgagtacg acctccccgt caacggtgag ctctctgagg   2400
gtggtgactg cccctgggcc gtgctcgtcg agagtggtca gtgtgatctc atgctcatct   2460
cctacatggg tattgacttc cagaacaaga gcgaccgcgt ctaccgtctg ctcaacacca   2520
ccctcacctt ctacggtgtt gcccaggagg gcgagaccct ggagtacgac atccgcgtga   2580
ccggcttcgc caagcgtctc gacggtgaca tctccatgtt cttcttcgag tacgactgct   2640
acgtcaacgg ccgtctcctc atcgagatgc gcgacggctg tgccggtttc ttcaccaacg   2700
aggagctcgc cgccggcaag ggtgtcgtct ttacccgcgc tgatctcctc gcccgcgaga   2760
agaccaagaa gcaggacatc accccgtacg ccattgcccc gcgtcttaac aagaccgttc   2820
tcaacgagac tgagatgcag tccctcgtgg acaagaactg gaccaaggtt ttcggccccg   2880
agaacggcat ggaccagatc aactacaaac tctgcgcccg taagatgctc atgattgacc   2940
gcgtcaccaa gattgactac accggtggcc cctacggcct tggtcttctc gttggtgaga   3000
agatcctcga gcgcgaccac tggtactttc cgtgccactt cgtcggagac caggtcatgg   3060
ctggatccct cgtgtctgac ggctgcagcc agctcctcaa gatgtacatg ctctggctcg   3120
gcctccacct taagaccggt cccttcgact tccgccccgt caacggccac cccaacaagg   3180
tccgctgccg tggccagatc tccccgcaca agggtaagct cgtatacgtc atggagatca   3240
aggagatggg ctacgacgag gctggtgacc cgtacgccat cgccgatgtc aacattctcg   3300
acattgactt cgagaagggc cagactttcg accttgccaa cctccacgag tacggcaagg   3360
gcgacctcaa caagaagatc gtcgtcgact tcaagggtat tgccctcaag ctccagaagc   3420
gctctggccc tgccgttgtc gctcccgaga agcccctcgc tctcaacaag gacctttgcg   3480
ccccggctgt tgaggccatc cctgagcaca tcctcaaggg cgatgctctt gcccctaacc   3540
agatgacctg gcacccgatg tccaagatcg ctggcaaccc cacgccctcg ttctctccct   3600
cggcctaccc tccccgtccc atcaccttca ccccgttccc cggcaacaag aacgacaaca   3660
accacgtgcc cggcgagatg ccgctctcgt ggtacaacat ggctgagttc atggccggca   3720
aggtcagcct ctgcctcggc cctgagttcg ccaagttcga tgactccaac accagccgca   3780
gccctgcatg ggaccttgct cttgtgactc gtgtggtctc cgtttctgac atggagtggg   3840
tccagtggaa gaacgtggac tgcaacccgt ccaagggaac catggttggc gagttcgact   3900
gccccatcga cgcctggttc ttccagggat cttgtaacga cggccacatg ccgtactcca   3960
tcctcatgga gatcgccctc cagacctctg gtgtcctcac ctctgtgctc aaggccccgc   4020
tcaccatgga gaagaaggac attctcttcc gcaaccttga cgccaacgcc gagatggttc   4080
gctctgatat tgacctccgc ggcaagacca tccacaacct caccaagtgt accggctaca   4140
```

```
gcatgctcgg agacatgggt gtccaccgct tcagcttcga gctctctgtt gatggtgtag   4200
tcttctacaa gggtaccacc tccttcggct ggttcgtccc tgaggtcttc atctcccaga   4260
ctggtctcga caacggtcgc cgcacccagc cctggcacat tgagtccaag gtgccttccg   4320
cccaggtcct cacctacgac gttacccccca acggtgccgg tcgcacccag ctctacgcca   4380
acgcccccaa gggcgctcag ctcactcgcc gctggaacca gtgccagtac cttgacacca   4440
tcgaccttgt ggtcgccggt ggctccgccg gtcttggcta cggtcatggc cgcaagcagg   4500
tgaaccccaa ggactggttc ttctcgtgcc acttctggtt cgactccgtc atgcccggct   4560
cgctcggtgt ggagtctatg ttccagctcg tcgagtccat cgctgtcaag caggacctcg   4620
ccggcaagta cggcatcacc aacccgacct tcgctcatgc tccgggcaag atctcctgga   4680
agtaccgtgg tcagctcacc cccacctcca agttcatgga ctccgaggcc cacattgtct   4740
ccatcgaggc ccacgacggc gtcgtcgaca tcgttgccaa tggtaacctc tgggctgatg   4800
gcctccgcgt ctacaacgtc agcaacatcc gtgtgcgcat tgttgctggc gccgcccctg   4860
ctgctgctgc tgctgctgct gctgttgctg ctccggctgc cgcccctgct ccggttgctg   4920
catctggccc tgcccagacc atcaccctca agcagctcaa ggctgagctt cttgacgttg   4980
agaagcctct ctacatctcc tccagcaacg gccaggtcaa gaagcacgcc gatgtggctg   5040
gtggccaggc caccattgtg caggcttgca gcctcagtga cctcggtgat gaaggcttca   5100
tgaagaccta cggtgttgtg gctcctctct acaccggtgc catggccaag ggtattgcct   5160
ctgctgacct tgtgattgcc actggtaagc gcaagatcct cggttccttc ggtgctggcg   5220
gtctccccat gcacattgtc cgtgccgctg ttgagaagat ccaggctgag ctcccgaacg   5280
gcccccttcgc cgtcaacctc atccactccc ccttcgatag caaccttgag aagggcaacg   5340
ttgacctctt cctcgagaag ggcgttactg tcgtcgaggc ctccgccttc atgaccttga   5400
ccccgcaagt cgtccgctac cgtgctgctg gtctttcccg taacgctgat ggctccatta   5460
acatcaagaa ccgcatcatc ggtaaggtct cccgtaccga gctcgctgag atgttcatcc   5520
gccctgcccc gcagaacctc ctcgacaagc tcatccagtc tggtgagatt accaaggagc   5580
aggctgagct tgccaagctc gtccccgtcg ccgacgacat cgccgtcgag gccgactctg   5640
gtggccacac cgacaaccgc cccatccacg tcatcctccc ccttatcatc aacctccgca   5700
accgcctcca caaggagtgc ggctaccccg ctcacctccg cgtgcgcgtt ggagctggtg   5760
gtggtgttgg atgcccccag gccgctgccg ctgctctcgc tatgggtgct gccttccttg   5820
ttaccggcac tgtcaaccag gtcgccaagc agtccggcac ctgcgacaat gtccgcaagc   5880
agctctgcat ggccacctac tctgacgtct gcatggctcc cgctgctgac atgttcgagg   5940
agggcgtcaa gctccaggtc ctcaagaagg gaaccatgtt cccgtccagg gctaacaagc   6000
tctacgagct cttctgcaag tacgactcct tcgagtccat gcctgccaca gagctcgagc   6060
gtgttgagaa gcgcatcttc cagtgccctc ttgctgatgt ctgggctgag acctccgact   6120
tctacatcaa ccgcctccac aacccggaga agatcacccg tgccgagcgt gaccccaagc   6180
tcaagatgtc tctctgcttc cgctggtacc ttggtcttgc ctctcgctgg gccaacaccg   6240
gtgaggctgg acgcgtcatg gactaccagg tctggtgtgg ccctgccatt ggagccttca   6300
acgacttcat caagggctcc taccttgacc cggccgtctc tggtgagtac ccggacgtcg   6360
tgcagatcaa cttgcagatc cttcgcggtg cctgctacct ccgccgtctc aatgtcatcc   6420
gcaacgaccc gcgtgtcagc attgaggtcg aggatgctga gttcgtctac gagcccacca   6480
acgccctcta agcgagttat atctgtctag aaaacttggc atggctagca atttatgtct   6540
```

```
agctattcca tacacacggt aatgccagta gcctgttagt tatagctctt ttggttgttg   6600

tctcacaata cactgacatc agcagaacaa aatgaaaggg gccttggcta ccatgaaatc   6660

aatacttcaa aggtctcttt ggtttcttta ctcgcatgtc gctatttact tacattcctc   6720

gagtacataa catatcatac atcaaagaaa ttaaaaagaa aacaaacatt caaatatgca   6780

ttactttccc tactgtacta gtaagtacgt ttctggtatt aagttgtttt ttctcaaaag   6840

aacaatgtgc ttacttgtaa aatccacagc tgcttacttg taagcctcaa ctagttagtg   6900

atgtgattat cataaaatgt tcgacactgt acctcctttc cagctatctt cctacacctc   6960

ctctgacgca ggttgacgga ggaggcgtgg gggttgattg aagtgcaaca caacgttttg   7020

tttaagatat tccttgcctt ggccgactcc aaatggatag cacagaagcc taatgataat   7080

ttgaattaat tttatttcga gcttatttaa tgctcttatc agagtccgta ggtatctctt   7140

ttcctactaa ttgttgaaaa aggatgtttt ggacatagca ggtcatcata ctatttggtt   7200

ccatcaaatt catatccatt tctttcgttc aagtgcttcc cttcctactt attatatata   7260

ttatatatcc ataaatgtaa aagagacgat tacgaatact ttgcatacat gtatagcgaa   7320

acagagatgg tagcaaaagt tcaccttcac taatctaaga atctctccac gtgggtaaaa   7380

acttcagcag taagattgta aatgatgtcc aagaacaaaa cgtcatgcta gtccaggggt   7440

tactgagcta acgattaata atgtttcgta gtcttcctaa ttgcaccatc aaaacttgtc   7500

tgcacaagtt ttaaagtatt ggagccttta ctgaagaatc agaggacata gatggggcac   7560

gttcgccttg aaaaaaatag tcttctttac ctgcatggtg ttacaaacaa aaacgagttg   7620

aaaatagctg tgcaaggagg caaacatgat tggaaaagaa aaacgagggg acccttatac   7680

aggagggcgc cacatagtag aatgagtaga ttgttagagt agggtacgct ttatgtgatt   7740

gattgaatgg gcgagtgaaa gttgctg                                       7767
```

<210> SEQ ID NO 8
<211> LENGTH: 7800
<212> TYPE: DNA
<213> ORGANISM: Schizoochytrium limacinum

<400> SEQUENCE: 8

```
ccacataatt tgaaagaaac attgaccacg cagccagtca tcgtgttgga aatcaccacc     60

gtgtgcccca cgacactact gcgaagcgct cgacacctcg tcgacaccaa gcacgagagt    120

ctgcgtgtaa gaaaaataaa tgaaagagct tttgtgtgat ggtacattcg ctgcgcttct    180

tcgcaacttg aagatggccc agtaataagc tcgggcatgc tgcaccaaac agaagtgggg    240

gtatcatgca gtcaagacct cataacaggg acacaaacgg ctgtctcctc gcgcgcctcg    300

gtacgtatcc aagtcccaaa ccgtgagaaa ttttcatgtt gatactggca tgatacgcct    360

cttgtcggac agatgggcgt tctcaacatt ggttctcatg tctgaatctt agggtttaat    420

ataatagtac tctaggtatg tagctattac agaaggtaag aggactagta gttctagtac    480

atgataggta gtgtcaggta ccagtgtgaa aaaaaaatgg aaggccattt tcgatgtccc    540

aggtcgatcc atataaattg tcgtggataa tgacagcaat ggagtttcgg attggctctt    600

gtcattactg tggaccacca ggtttctcgt gatgtaaact aaccctctag cactttttaa    660

ccttcatcga cctggtttta gatctcagaa ttcaatagga agtggcgttg tcaaagttgt    720

tggttctatc gttttgagta cttaatagca ggtactgcct aagcaagtct cagcttccgg    780

cactgtagct gttctttcgg ggaggggaga ttctgctgtt ctttgaagta gtattcttca    840
```

```
cgagagtttg tttgttacct tttctgattc acaaatgaga aagaagagca caggataagt    900
tgtaaaaata tcctggtatt cattcttcac gggaaaaccc aaacgagtaa taatgtccac    960
catcaggcta agccatcatg caaatgcaaa gtatgatgaa ttatccctca atgctttaat   1020
gagggtcttt agcataacat gaatggtaca aatcaaatat aggtgtttag gaagctctca   1080
aaaatgctaa ctcccatgta cccaaacacg cgaaacttcc ggcatcttga agaattcgcc   1140
gttgactcac caaccaatga tggtcagtgg aaacaacaac tgcacgatct aatctcgtcc   1200
tgggcagaca cgactggctt gacatgcatc ttcaccaaca acgcacaact agaactattg   1260
taattgagac tttaaaataa ctaagcttcc taggcgttta agcaacaaca aatccctttt   1320
attcttgcga cattgaaata gcagcgacta caagtaaaag cgccctgtgc caatactagt   1380
gtttgcggaa agctcatgtt gtggtcttca gaaaatgagc cttggcacac ggcaaacttt   1440
gccaaggtca tacaatcaaa tggtgaagag gaaatagcca aagagactca ccttgatctt   1500
gaagacgtgc gagataatgt tgttcggtac gcatcagaat ctccctctca acgtgttatc   1560
atatggcttg atgataaagg aaacgaaagt tctgttctta ctcgtgaaag tctagtcaag   1620
agcgctcagg gtcttgcaga ggcaatgaga acccagtgga agatgaaaac aggcgagaaa   1680
gttctccttg tgtttttgcc aggtacagat tttatcattg ctatgatggc atgtcttttt   1740
ggaggcttcg tcgcggttcc agtctaccca ccagatccaa acagtccaaa ggcaggactt   1800
ttaaaactag gtaaagcggt tgaagttgca caggtgtcta ctgtgatttc tcacaccaaa   1860
tttctccatc tgcgtcggtt agtgattggc gttaagaagt ttccgcgagg actgaaatgg   1920
cataacatga gcaaagtgaa accagctgct tctattggcg tcacaatgcc tgtagccagc   1980
catgaattag ccttcataca attttcgagt ggaagcacag gcgaccccaa gggtgtttgt   2040
gtaacacatg gaaacctcaa cagcaatctt gcaagtatta agacgtctat gggcatgagt   2100
gaagacacag ttggtgtcac atgggtccca ttttatcatg acatgggcct ggtaggtgca   2160
attcttacta ccctgtattc tggcgcaatc atggtagcca tgtctccgat tagcttttta   2220
caaaatccat ttgtgtggtt aaatgctatc tcaaagtatc gtggcacgac cacttgcgcc   2280
cccaactttg cgtatgtgct tgcagtacgt aaagttccag tagccaaaag gaaggagctc   2340
gacctatcat gctgtaagcg ctattcgaat ggcgctgagc cagttcgtgc agaaacctta   2400
tgggcctttg cagaggcata cgagaagcaa ggtgtgaaag ctgagtactt ggatccattt   2460
tatggtatgg cagagaacgt tgttcttatt tccacgcatc gaggtccaca tatgcctctc   2520
atgttgcggc tcaaggctgg gttttccaat aaacctggct ctaaaatagt tcttgtgcat   2580
cccgaagaag atggacaaga tttagtaggc aacggccctc ctggcgtagg tatcgaggtc   2640
tcggttgtac acccagagac aagggtacta ttagaagatg atactatcgg tgaactctgg   2700
gtaacaggtc catccaaagt cagtgaatac cttggcaagc ctgctctgtc ggaagaagaa   2760
ctcaatgcca agatttcaac ccgctctgac gaacgaacct ttctccgcac aggtgacatg   2820
ggtttcgttc ataaaggcga aatttttgtg tgtggacgca tcaaagacat gatgattgtt   2880
cgtggacgta acattttccc ccaagacgtt gaaagcactg tagatcaagc aagtactaag   2940
attcgccctg gctgttgtgc tgttttcacg cttgaaggaa ctgaaaatgt tgttgttgtt   3000
gctgaagtcc gtgatggaaa acttgctaac gaagctggtg gcttggcaga cctgattcgc   3060
gctcgcatca tgactgaaca cagttttcga ccttttgctg tgattctaat caagccacga   3120
acgattccta agaccacaag cggcaagatc caacgccgag ctgctcgaga agcgtatgtt   3180
caaggagagc tatcagttct tgtcgaggct cgtgatgaaa gctgtttacc agaacgccgt   3240
```

```
tctgcaatgc agaggcgtgc aagtcttgcc gctttggatg acctccttga tgagttagag   3300
gaaatggact tatggacagg gcctgcacag atgcgagcgc ttgtggaaga gatgaattta   3360
gcaggataca cagtctttga tgagcttgct tgtttgcgca tacctgtcag tttgtctcct   3420
cttgttaaac agcttcgtga gttgttagtt catcgcccaa ttcttcgtaa ctttgctgcc   3480
gacttagcca tcggctgcaa tgaggagcta cgaagtagtc gggtcgtggg tccgttgagc   3540
cttgcatatt tccttcatat ttgcattgat gcactgcaag atcgggagtt gtttgttcag   3600
attcttcctc aagtccttga ttcccttgtt gaaaacttta gcgtccctgc caagcgtacc   3660
tggtttggtc atgtacaagc tgggcttgca gcctgggcag caaagctgca acttcagcaa   3720
ggtgggttac gttgtacaga tgagaaccat gctcagttcc aactaggact gggtgtttta   3780
gcgtcggtgg gggctgaaat gcttcatggt gttaaaaagc ccacgttatc tgctctttgt   3840
ggtgctagct tatatgaggt tataagtcac gagactcacc gtggtcacac acgaagtgcc   3900
attgttgaat cttttgttgc atggaatttt gcatttttag aaaaatacaa gcccttcaag   3960
gatatcaccc gggatctgcc atacgaagtt ctactgttgg tgccaagcct cgtaagtgca   4020
cagtcgctag acgagctgta ccataatcgc atgataggac tcttgctgct tatgggcgca   4080
aaacagtcaa aattatttgc caatacagaa agaagtattc agttccgagc aggtaccatc   4140
gatgatgcaa tttgccaggt catgatttca ttaaatgctc agtgtgcaga gcgcctggcc   4200
aatagtatac ctcattattg tggtcctcgc gaaatgagtg ctgcgcccga atcattgttt   4260
tctaggagta agtatgctct tcgaaacttg cagcgagcct ctgttttgcc agacaatctt   4320
ttcgataaca catggagtga gttggtggaa aatatggaga gtcatggtga ggttcgtgct   4380
ggtgagaacc ctgacgaacg tcttcgctgg cttttgcaat gcgtacgtca aagcattgaa   4440
gctccttcct taggtcttga tgacgatctc ttcgaagcgg gtatgagttc catggcaatg   4500
attgaagtga atgctcatgt cgagaatttg attggtttca acgagacagt cgagccagat   4560
ttcattgcca agtatcgtac agtgcggcgt ctggcggagg ctgttgaaca gaaacgtatg   4620
gctcatgttg agctagagga agtcaaatac tcaaatcaac ctgccctgcc atatcatgtg   4680
gcaaccacaa tccaatttct cggtatttgg gtgctttttt tcatgatgtc cgcagcgatt   4740
ttacccgcct atcactatgg actatgggtt cggtacaaat cgggacttcc atctccttgg   4800
tcacactata gagttaccag cacgctcagc atgtttgggc tattagtgcc ttttgtgata   4860
cctttgtgga ttgcttcatt ttcgctgctg gttcttgttg caaagtggat cgtagtgggg   4920
aaatggcgtc catgcgaagt gaaaatcaac tcgtttccgt atttacgctg gtggttcgta   4980
gaccgtgcta cccatttgtg ggagatagct gtgggtcgat ggtttcttaa cacgccatta   5040
ctgaacatat tttatagggc tatggggggg caagtgtctt tcacagccaa ggttaaagtt   5100
aatcttcggg atcttgacct cgtgcatatt ggcgctgggg cagaggtgcg cggaacattg   5160
gtgtgccgag tctttgatgc caaagaaaga actttgcgtt ttcgacgagt caaacttggc   5220
caaggtagcc ggctgcgtac aggttcagtc gtgatgcctg gatgctgggt aggtaaaggt   5280
gcagaagtgg tacctttaca agtgctcaac gagggtgaga aagttgctga aaacattgag   5340
gctatagaga cttctcattc tagcattaat gctaccgtgc gtgagctatt tgcaaaattg   5400
ttcatcatgt gctctttcct gttgttgtat tttaacactt cagtcatcat tggcttgatc   5460
tgggatgcgg cgggttaccc tgaaaacttt cggtatgtgg aattggtcta ttgggcatca   5520
tcttatctcg tgacagcatg tataatgtcg tttgtagctg tcggtatgaa atggatactg   5580
```

```
attggtcgtc tcaaaacagg tgctattaaa ggctctagtt tgcggatttg ggcggctgac   5640
tatttgttca cactagtttg ggtgacttgg attcaatttt tagatgaaac acgttctata   5700
ttgggttatg cacgcggttt aggggcttcc atcgggccag gttcatttgt atctgcaata   5760
aagtggattc agccatcaaa tgcagacatg gtgaagatgg gagcctcgtc catggcaagt   5820
ctaattctca ttgagacaga aagtgaagga attcgagggc gcgtagaaat aggagactac   5880
tgtgaggtga gttacctggc attactaggt cgaggatcca caatgcaatc acgctcgtat   5940
ttgggaagtt tgagtgttct catggaaggc gagaccttgc ctacagggta ccgacaattt   6000
cgcggagcga cctttcctgt ggccactaag gaaggtgagg tagatatgga aatctggagc   6060
acaacagatg agattttagg acttttgatg cgcgtggtgt tgattgttct tgtggtcttc   6120
tcgctcatcc cagcgtatga gtttgcaaat tttgttttgt ttgatgctga tatggataga   6180
aatgctgcca ttcttctttt agctgtaagc ttctggctag cgatggtaag catgatggta   6240
gcacaaaagc taatggcaac tgctgtgttg ggtttggta aagagttgca agagcttcct   6300
tgtcgacttt ctttttactg ctcatatcag ctgtttacat actttttcga aaatcttttg   6360
ctcgtggttc tacatgggac tccattttat aattcatttg cgcgctttat gggtgcatgc   6420
gtgggacgtc gggtgatttt actcacgggt ggtcttcgag agcaccaact tatcacgcta   6480
gagtatggcg cagttgtaga caatgcgcaa ctcactggtc accaggcgtg cgatggagcg   6540
tttgaactag gtccttcact tgttggcgca gagtcagtac ttcagcctgg tgctgtatgt   6600
ctttcgaatg gaattgttca cgctggtact gttattcacg ctcgttcctt tgcaccaaag   6660
cgtacagggg ctgcaatata tggcaagccg tctcctgttt gcattgctcc cgaggttgca   6720
tagtttccta catattgtct actatcattc ccggattgtg gactcatgtt aaacagtgca   6780
tttatttcga ttgaatattt cctgatcatc ctttcgttac ttctcaactc tatgtgaata   6840
catagagata ctttgtttgt gcatccaaca ggctggaaag tatgtacggc ctaagtaaat   6900
tactgattgt aagtaaaaaa tcaatgataa aaatgaaagt cggtctgtgt caattgatca   6960
ccggtgcgct ttcaattttc agatgaatac aaattgcttt caaaattact acgagaacga   7020
aagacacgaa cccctttta cataaaaaca ccgcaacaat ccataataag tgcactttga   7080
gcaaaatatg aaatctagta aataaatgtg aacatatttg ataaagttgt cactgcagga   7140
tcttactctg attgcttgta tcactccttc tatagtttta aacaatggta tgtcctttat   7200
gttaacataa acccttaca tagcacataa atttgcattg cataaagaag ggtaggttta   7260
cttttattat ttgaaatcag caatcaaaga aacgcgtaaa gctctgatca gctaggaagg   7320
atgaaagcaa gatgcttgag aatcttgaag atgttttaag aaggcactat aaacgtgaac   7380
gtttagtgtt aggaatctct tcgcctttta aaaatgaaat ttgcgagcga ctgatttgta   7440
ttgtatttag taaacttgag caagtttgac ttgtattaaa cacaatataa aaggctagga   7500
tttacccttc caaatcatct tgaaaaatgc aattctcgag tccctttgct tcacatatct   7560
gattatgtac tttttatctt acaccaatct aaatagttca gaacctacaa tggtgtgtca   7620
agcaaggact ctcacaatgt cttgttcgca tgacaacttt aattgtaggt cttaacatgt   7680
agcaagggta cactagacaa ctcaggaata ctatgacagg cttaaaaaac tgcaggttct   7740
aattcatagc aatcaagtct aaaaccgtgt gattttaaaa tatgcataag aacggtgcac   7800
```

<210> SEQ ID NO 9
<211> LENGTH: 669
<212> TYPE: PRT
<213> ORGANISM: Schizoochytrium limacinum

<400> SEQUENCE: 9

```
Leu Glu Arg Ala Leu Gln Glu Glu Ile Glu Val Leu Gln Gly Asp Thr
1               5                   10                  15

Leu Ser Ala His Leu Ser Lys Ile Leu Cys Ala Ile Ser Ser Thr Phe
            20                  25                  30

Ala Arg Phe Glu Ser Tyr Cys Glu Asn Thr Val Leu Asn Glu Ala Ser
        35                  40                  45

Lys Cys Thr Pro Gln Glu Leu Ser Glu Leu Tyr Asp Tyr Thr Ser Leu
    50                  55                  60

Gly Leu Lys Glu Pro Ser Val Leu Asp Val Asp Lys Leu Tyr Gln Lys
65                  70                  75                  80

Leu Gly Lys Ser Arg Glu Ala Thr Lys Ser Leu Lys Arg Ala Arg Glu
                85                  90                  95

Glu Leu Glu Ala Glu Asp Leu Glu Glu Glu Arg Glu Tyr Phe Arg
            100                 105                 110

Asn Arg Ile Lys Lys Gln Lys Arg Ile Leu Ser Lys Gly Asn Pro Ile
        115                 120                 125

Glu Leu Ser Lys Val Phe Arg His Lys Leu Ala Glu Thr Leu Gln His
    130                 135                 140

Ala Gln Glu His Tyr Pro Glu Leu Leu Gln Asp Arg Ala Trp Leu Glu
145                 150                 155                 160

Lys Leu His Val Ala Ala Glu Gly Val Phe Glu Val Ala Cys Ser Asp
                165                 170                 175

Leu Trp Leu Thr Asn Val Thr Val Ser Asp Phe Gln Arg Val Gly Glu
            180                 185                 190

Pro Leu Ser Phe Arg Gly Gly Lys Lys Val Gln Lys Val Leu Asp Asn
        195                 200                 205

Val Gly Lys Thr Met Val Leu Lys Glu Phe Gln Leu Gly His Pro Ser
    210                 215                 220

Gln Ser Lys Thr Phe Tyr Gln Gln Val Ala Asn Leu Gly Lys Val Val
225                 230                 235                 240

Ser Gln His Val Ile Arg Ile Thr Gly Ala Phe Val Asp Met Thr His
                245                 250                 255

Gly Glu Ser Arg Gly Cys Ile Val Met Pro Phe Tyr Glu Gln Gly Asp
            260                 265                 270

Leu Ala Lys Trp Ile Glu Ser His Pro Asn Glu Gly Lys Glu Ala Arg
        275                 280                 285

Asp Arg Leu Ala Val Gly Leu Leu Val Gly Val Ala Asp Leu His Ala
    290                 295                 300

His Cys Ile Val His Cys Asp Ile Lys Pro Glu Asn Ile Phe Leu Thr
305                 310                 315                 320

Ser Asn Gly Thr Pro Leu Ile Gly Asp Phe Asp Gly Ile Lys Val Val
                325                 330                 335

Asn Tyr Thr Ala Thr Tyr Thr Ser Leu Gln Ala Thr Pro Arg Tyr Ile
            340                 345                 350

Ala Pro Glu Leu Gln Asn Gly Pro Val His Arg Phe Glu Thr Ala Met
        355                 360                 365

Asp Met Tyr Ser Val Gly Ile Ser Leu Lys Glu Leu Tyr Pro Thr Glu
    370                 375                 380

Arg Thr Ala Ala Met Gln Thr Leu Ile Glu Ala Leu Thr Ala Arg Asp
385                 390                 395                 400

Pro Ser Gln Arg Pro Ser Ala Arg Gln Ala Leu Gln His Gln Ala Phe
```

```
                405                 410                 415

Gly Ala Pro Gln Ile Pro Leu Met Glu Cys Leu Val Cys Phe Glu Lys
            420                 425                 430

His Arg Leu Ser Glu Gly Thr Ser Cys Glu Glu Gly Asp Phe Leu Cys
        435                 440                 445

Arg Gly Cys Ile Glu Ser Ala Val Glu Ala Ala Ala Gln Pro Leu Ala
    450                 455                 460

Asn Val Arg Val Asp Ala Asp Gly Thr Met Ala Cys Met Lys Pro Glu
465                 470                 475                 480

Cys Ser Gly Lys Ile Ser Gly Gln Glu Ile Thr Arg Leu Ala Pro Thr
                485                 490                 495

Ala Leu Asn His Leu Leu Leu Ile Ala Lys Met Lys Ala Glu Ser Glu
            500                 505                 510

Ala Ala Val Trp Ala Glu Lys Glu Ile Gln Arg Arg Ile Ala Glu Val
        515                 520                 525

Val Arg Ala Glu Glu Gln Asn Ser Asp Ala Arg Trp His Leu Leu His
    530                 535                 540

Ile Gln Glu Asn Ile Leu Ser Thr Cys Cys Pro Asn Cys Lys Ala Tyr
545                 550                 555                 560

Val His Asp Phe Asp Gly Cys Cys Ala Val Lys Cys Gly Asn Asn Ala
                565                 570                 575

Cys Gly His Leu Phe Cys Ala Trp Cys Leu Gly Tyr Ser Ser Gln Asp
            580                 585                 590

Gly Asp Val Cys His Ala His Val Arg Thr Cys Ser Arg Arg Leu Gly
        595                 600                 605

Gln Asp Leu Tyr Phe Pro Gly Ser Leu Glu Gln Val Cys Glu Ala Trp
    610                 615                 620

Arg Leu Leu Arg Ala Glu Arg Leu Arg Glu Tyr Trp Asn Ala Gln Ile
625                 630                 635                 640

Gln Asp Arg Asn Leu Arg Leu Val Leu Lys Asp Leu Leu Ser Pro Leu
                645                 650                 655

Leu Thr Pro Asp Ile Val Gly Ala Asp Phe Arg Leu Glu
            660                 665


<210> SEQ ID NO 10
<211> LENGTH: 1193
<212> TYPE: PRT
<213> ORGANISM: Schizoochytrium limacinum

<400> SEQUENCE: 10

Asp Arg Ile Asn Glu Gln Glu Leu Ile Leu Ser Gln Gly Asn Pro Ile
1               5                   10                  15

Glu Leu Ser Lys Ala Phe Arg His Lys Leu Ala Glu Thr Leu Gln His
            20                  25                  30

Ala Gln Glu His Tyr Pro Glu Leu Leu Gln Asp Arg Ala Trp Leu Lys
        35                  40                  45

Arg Leu His Ile Ser Ala Glu Gly Val Phe Glu Val Ala Cys Ser Asp
    50                  55                  60

Leu Trp Leu Ala Asn Val Glu Ile Ser Asp Phe Lys Pro Val Gly Glu
65                  70                  75                  80

Leu Leu Ala Ser Arg Gly Gly Lys Thr Val Gln Lys Val Leu Asp Gly
                85                  90                  95

Asp Gly Arg Thr Leu Val Leu Lys Gln Phe Gln Leu Gly His Thr Ser
            100                 105                 110
```

```
Gln Ser Lys Thr Phe Tyr Lys Gln Val Ala Asn Leu Gly Lys Val Val
        115                 120                 125

Ser Gln Asn Val Ile Arg Ile Thr Gly Ala Phe Val Asp Met Thr His
    130                 135                 140

Gly Ala Pro Arg Gly Cys Ile Val Met Pro Phe Tyr Glu Gln Gly Asp
145                 150                 155                 160

Leu Ala Lys Trp Ile Glu Ser His Pro Asn Glu Gly Lys Ala Ala Arg
                165                 170                 175

Asp Arg Leu Ala Met Gly Leu Leu Ile Gly Met Ala Asp Leu His Thr
            180                 185                 190

His Gly Ile Val His Cys Asp Ile Lys Pro Glu Asn Ile Phe Leu Thr
        195                 200                 205

Ser Asn Gly Thr Pro Leu Ile Gly Asp Phe Asp Gly Ile Lys Val Ala
    210                 215                 220

Asp Tyr Thr Ala Thr Tyr Thr Ser Leu Gln Val Thr Pro Lys Tyr Leu
225                 230                 235                 240

Ala Pro Glu Leu Gln Asn Gly Pro Val Tyr Lys Phe Glu Thr Ala Met
                245                 250                 255

Asp Met Tyr Ser Val Gly Val Ser Leu Lys Glu Leu Tyr His Thr Glu
            260                 265                 270

Arg Thr Ala Ala Met Gln Thr Leu Ile Asp Ala Leu Thr Ala Thr Asp
        275                 280                 285

Pro Gly Gln Arg Pro Thr Ala Arg Gln Ala Leu Gln His Glu Ala Phe
    290                 295                 300

Gly Ala Pro Lys Ile Pro Val Lys Ile Cys Leu Val Cys Met Glu Glu
305                 310                 315                 320

Tyr Gln Leu Ser Glu Gly Thr Ser Cys Glu Glu Gly Asp Phe Leu Cys
                325                 330                 335

Arg Asp Cys Ile Glu Ser Ala Val Glu Ala Ala Ala Gln Pro Leu Ala
            340                 345                 350

Asn Val Arg Val Asp Ala Asp Gly Thr Met Glu Cys Met Lys Pro Glu
        355                 360                 365

Cys Val Gly Arg Ile Ser Gly Gln Glu Ile Thr Arg Leu Ala Pro Ser
    370                 375                 380

Ala Leu Asn His Leu Leu Leu Ile Ala Lys Thr Lys Ala Glu Ile Glu
385                 390                 395                 400

Ala Ala Val Trp Ala Glu Gln Glu Ile Gln Arg Arg Ile Ala Glu Ala
                405                 410                 415

Leu Arg Ala Asp Gly Gln Asn Arg Asp Ala Gln Arg His Leu Leu His
            420                 425                 430

Ile Gln Glu Lys Ile Leu Ser Thr Cys Cys Pro Asn Cys Lys Ala Tyr
        435                 440                 445

Val His Asp Phe Asp Gly Cys Cys Ala Val Glu Cys Gly Asn Asp Gly
    450                 455                 460

Cys Gly His Ser Phe Cys Ala Trp Cys Leu Glu Phe Ser Ser Gln Asp
465                 470                 475                 480

Ser Gln Ala Cys His Ala His Val Leu Val Cys Ser Arg Asn Leu Ser
                485                 490                 495

Asn Asn Lys Ser Tyr Phe Ala Glu Ser Phe Glu Gln Val Arg Glu Ala
            500                 505                 510

Trp Gln Leu Leu Arg Ala Glu Arg Leu His Glu Tyr Trp Asn Ala Asn
        515                 520                 525

Ile Gln Asp Glu Asn Leu Gly His Ala Leu Glu Gln Gln Leu Val Pro
```

530 535 540

Leu Leu Thr Pro Asp Ile Val Gly Pro Glu Phe Lys Leu Ile Glu Asp
545 550 555 560

Val Leu Pro Ser His Tyr Cys Ser Ile Ser Ala Thr Val Pro Thr Thr
565 570 575

Thr Thr Thr Thr Thr Thr Thr Ala Ile Val Arg Gly Val Gly Phe Val
580 585 590

Ala Ala Thr Phe Val Leu Thr Ile Ala Glu Gln Pro Ser Thr Thr Val
595 600 605

Ala Ile Gly Phe Val Leu Leu Gln Pro Leu Ala Tyr Val Leu His Ala
610 615 620

Pro Val Arg Val Phe Gln Tyr Leu Asn Glu Ser Gly Lys Lys Asn Trp
625 630 635 640

Phe Asp Glu Pro Thr Gln Glu Met Ile Glu Phe Leu Leu Ser Glu Asn
645 650 655

Glu Ala Ile Leu Ala Glu Gly Arg Ala Glu Gly Arg Ala Lys Val Leu
660 665 670

Ala Glu Phe Ile Glu Pro Leu Leu Ala Gly Leu Arg Lys Pro Leu Phe
675 680 685

Leu Lys Val Thr Leu Arg Val His Ala Ser Thr Ala Ala Thr Pro Ser
690 695 700

Ala Trp Gly Leu Glu Phe Ile Ser Leu Lys Leu Trp Arg Gly Phe Thr
705 710 715 720

Ser Glu Ile Ile Asn Pro Phe Leu Ser Ala Asn Leu Leu Asn Met Gln
725 730 735

Ile Arg Asn Thr Ser Phe Arg Thr Ser Leu Tyr Pro Leu Asn Ile Ser
740 745 750

Gly Asn Thr Asn Ala Met Ala Ser Leu Phe Asn Asn Trp Cys Cys Arg
755 760 765

Pro Phe Val Gly Leu His Thr Glu Val Ala Asn Phe Pro Lys Val Ile
770 775 780

Val Arg Ile Glu Asp Asp Ile Gly Leu Ser Ala Lys Pro Asp Leu Thr
785 790 795 800

Leu Val Lys Ile Asp Asp Gln Arg Asn Glu Thr Val Phe Ser Ile Val
805 810 815

Glu Val Lys His Pro Asn His Phe Leu Pro Leu Ser Glu Asn Pro Asn
820 825 830

Trp Thr Asp Arg Arg Asn Ala Ala Ala Ala Ala Gly Ile Ala Ile Phe
835 840 845

Thr Ser Arg Gly Gln Pro Arg Gln Ala Leu Glu Gln Leu His Gly Asn
850 855 860

Met Leu Ile His Gly Val Lys Tyr Ala Ile Leu Thr Ser Val Glu Leu
865 870 875 880

Thr Tyr Phe Val Lys Arg Asp Asn Lys Gly Asn Met Arg Ile Thr Arg
885 890 895

Gly Phe Tyr Gly Ala Glu Thr Gly Gly Ala Arg Val Ile Ser Thr Asn
900 905 910

Glu Ala Met Ala Ala Phe Ile Tyr Ile Ala Ser Arg Asp Pro Asp Asn
915 920 925

Gly Lys Phe Arg Pro Arg Ser Asn Ser Thr Ser Thr Glu Ile Arg Ala
930 935 940

Tyr Ser Glu Arg Ile Gln Thr Lys Phe Gly Gly Arg Ser Ile Ser Asp
945 950 955 960

```
Arg Ala Thr Glu Lys Phe Lys Asp Arg Val Gly Glu Thr Ala Leu Gln
                965                 970                 975

Phe Met Lys Gly Leu Asn Gln Leu Ala Val Asn Ile Glu Glu Leu Arg
            980                 985                 990

Ser Asn Leu Ile Glu Val Leu Pro  Phe Lys Asp Glu Ala  Tyr Leu Phe
        995                 1000                1005

Met Pro  Leu Pro Trp Ser Lys  Asp Tyr Arg Leu Val  Thr Ser Tyr
    1010                 1015                 1020

Val Val  Arg Ile Pro Trp Val  Ser Asn Lys Asp Phe  Asn Trp Asp
    1025                 1030                 1035

Ile Phe  Val Lys Thr Met Ala  Val Ser Lys Asp Trp  Ala Arg Glu
    1040                 1045                 1050

Thr Tyr  Glu Phe Glu Lys Ser  Phe Phe Leu Asn Glu  Val Lys Leu
    1055                 1060                 1065

Tyr Leu  Gly Pro Leu Arg Leu  Leu Gln Gly Lys His  Ala Pro Phe
    1070                 1075                 1080

Leu Val  Tyr Gly Gly Thr Phe  His Lys Arg Ile Ile  Ile Ala Thr
    1085                 1090                 1095

Thr Phe  Ser Gly Glu Thr Ala  Thr Lys Glu Leu Ile  Leu Ala Asn
    1100                 1105                 1110

Ser Ser  Trp Ala Ile Thr Ala  Ile Arg Ala Ser Leu  Ser Ala Leu
    1115                 1120                 1125

His Gln  Val Gly Val Leu His  Gly Asp Ile Ala Leu  Arg Asn Ile
    1130                 1135                 1140

Ala Ile  Asp Thr Thr Thr Lys  Thr Ala His Leu Ile  Asp Phe Gly
    1145                 1150                 1155

Arg Ser  Ser Gln Asp Lys Thr  Thr Lys Lys Asn Arg  Asp Thr Glu
    1160                 1165                 1170

Met Lys  Glu Leu Asn Thr Leu  Leu Gly Phe Ala Ile  His Arg Lys
    1175                 1180                 1185

Arg Ile  Arg Asp Ser
    1190


<210> SEQ ID NO 11
<211> LENGTH: 772
<212> TYPE: PRT
<213> ORGANISM: Schizoochytrium limacinum

<400> SEQUENCE: 11

Leu Trp Pro Ala Glu His Leu His Glu Thr Tyr Glu His Ile Arg Asn
1               5                   10                  15

Asp Ala Leu Gly Ser Gly Cys Ser Val Val Ile Tyr Val Ala Leu Asp
            20                  25                  30

Cys Asp Ala Leu Cys Ala Val Lys Ile Leu Thr Ser Leu Leu Lys Ala
        35                  40                  45

Asp Asn Val Ala Tyr Lys Leu Arg Pro Val Arg Gly Tyr Ser Asp Ile
    50                  55                  60

Leu Glu Asp Phe Arg Glu Thr Ser Lys Ala Glu Ala Ile Lys Ser Ile
65                  70                  75                  80

Ile Met Ile Asn Cys Gly Gly Asp Val Asn Ala Gln Glu Met Phe Asn
                85                  90                  95

Leu Asp Asp Gly Met Thr Cys Tyr Ile Ile Asp Ser Ala Arg Pro Tyr
            100                 105                 110

Asn His Ala Asn Leu Leu Arg Ser His Met His Thr Ile Val Phe Ala
```

```
        115                 120                 125

Asp Asp Phe Met Lys Glu Glu Asp Leu Val Lys Glu Ala Glu Leu Leu
    130                 135                 140

Glu His Leu Asp Glu Asp Asn Val Asp Glu Leu Leu Gly Ser Asn Asp
145                 150                 155                 160

Asn Asp Asp Asp Asp Asp Asp Asp Asp Asp Asp Asp Ser Asp Asp Gly
                165                 170                 175

Lys Gly Glu Val Glu Asp Gly Asn Asp Ala Asn Ser Ala Arg Asn Gly
            180                 185                 190

Gln Glu Gly Glu Ile Asp Ser Asp Glu Glu His Glu Phe Asp Gly Gly
        195                 200                 205

Asn Pro Gln Gln Asn Ala Ser Asp Ser Asp Asp Asp Glu Asn Glu Asp
    210                 215                 220

Ala Asn Lys Gln Thr Ser Asn Asn Thr Asn Asn Lys Thr Ser Lys Ala
225                 230                 235                 240

Lys Ser Ala Ser Gln Leu Leu Thr Glu Gln Glu Glu Ala Glu Ile Glu
                245                 250                 255

Arg Glu Leu Ala Ala Glu Asn Gly Thr Arg Lys Lys Arg Arg Arg Thr
            260                 265                 270

Ser Ser Ser Ser Ser Ser Ser Gln Asn Asp Lys Asn Asn Asp Ser Gly
        275                 280                 285

Asp Asp Asp Asp Asp Asp Asp Asp Asp Asp Asp Lys Asp Asp Asp Ser
    290                 295                 300

Leu Pro Lys Arg Lys Val Arg Glu Lys Val Asp Ala Glu Glu Pro Met
305                 310                 315                 320

Asp Asp Lys Ala Arg Val Ala Lys Tyr Tyr Ala Gly Ser Phe Arg Gly
                325                 330                 335

Thr Ser Ala Ala His Val Leu Phe Ser Leu Ser Gln Arg Leu Asn Lys
            340                 345                 350

Asp Gln Lys Ile Phe Leu Trp Leu Ala Ile Val Gly Thr Thr His His
        355                 360                 365

Phe Ile Asn Ser Glu Leu Ser Glu Glu Asp Tyr Leu Leu Arg Val Leu
    370                 375                 380

Thr Tyr Gln Asp Leu Val Lys Asp Arg Ser Met Ser Arg Arg Ala Gly
385                 390                 395                 400

Gln His Thr Val Thr Glu Asp Gly Ala Glu Val Pro Leu Met Glu Gly
                405                 410                 415

Gln Ser Met Glu Phe Ile Glu Glu Leu Arg Leu Met Leu His Arg His
            420                 425                 430

Trp Ser Leu His Glu Ala Phe Leu Tyr Ser Asp Tyr Ile Ala Ala Lys
        435                 440                 445

Leu Gly Ile Trp Lys Asn Asp Gly Glu Ala Lys Leu Arg Thr Phe Phe
    450                 455                 460

Ala Lys Met Gly Ile Ser Arg Lys Glu Ala Glu Gln Lys Tyr Ser Phe
465                 470                 475                 480

Met Asn Met Ser Val Lys Arg Ala Leu Lys Asp Lys Ile Gly Ala His
                485                 490                 495

Gly Ala Asp Phe Ser Leu Asp Glu Ser Phe Val Tyr Ala Ser Phe Gln
            500                 505                 510

Phe Arg Ala Gly Phe Gly His Gln Leu Ser Ala Ala Asp Thr Ala Tyr
        515                 520                 525

Cys Met Ala Ala Leu Leu Glu Ser Ala Ala Thr His Pro Thr Val Phe
    530                 535                 540
```

```
Ala Asp Asp Ser Gly Ala Asp Ala Thr Glu Asp Ala Thr Glu Ile Pro
545                 550                 555                 560

Glu Val Asp Leu Asp Gly Asp Asp Leu Asp Tyr Ala Gly Glu Asp Gly
                565                 570                 575

Ala Asn Gly Gln Lys Glu Asn Ser Lys Ala Ile Leu Ala Ala Ser Leu
            580                 585                 590

Trp Lys Gln Ser Phe Asn Ala Ala Tyr Asp Ala Leu Ser Phe Ser Gln
        595                 600                 605

Thr Thr Arg Asn Gln His Leu Leu Glu Gln Gly Leu Asn Leu Ala Lys
    610                 615                 620

Ala Leu Gln Lys Ala Ile Ile Gln Glu Gly Gly Asn Ile Ile Ser Gly
625                 630                 635                 640

Thr Lys Ile Ala Ser Ala Gly Ser Phe Arg Tyr Cys Ile Leu Glu Gly
                645                 650                 655

Leu Pro Pro Lys Leu Val Ser Ile Phe Ser Gln Pro Asp Thr Leu Leu
            660                 665                 670

Arg Leu Ala Lys Phe Ile Met Leu Ala Tyr Thr Ser Ala Gly Lys Trp
        675                 680                 685

Ser Gly Leu Gly Ala Lys Pro Leu Val Leu Gly Val Lys Asn Leu Lys
    690                 695                 700

Thr Asn Lys Ala His Phe Val Gly Leu Pro His Pro Thr Phe Gly Asp
705                 710                 715                 720

Asp Ala Ile Ala Lys Asn Pro Phe Gly Arg Tyr Phe Arg Val Ala Ala
                725                 730                 735

Gln Lys Val Gly Thr Ala His Ile His Val Gly Phe Ser Ser Ala Cys
            740                 745                 750

Ile Glu Ile Pro Leu Glu Leu Val Gln Lys Phe Leu Val Ala Leu His
        755                 760                 765

Glu Ile Thr Ala
    770


<210> SEQ ID NO 12
<211> LENGTH: 2188
<212> TYPE: PRT
<213> ORGANISM: Schizoochytrium limacinum

<400> SEQUENCE: 12

Ala Gln Arg Glu Asn Arg Leu Glu Ala Asn Met Asp Thr Arg Ile Ala
1               5                   10                  15

Val Ile Gly Met Ser Ala Ile Leu Pro Cys Gly Thr Thr Val Arg Glu
            20                  25                  30

Ser Trp Glu Ala Ile Arg Asp Gly Ile Asp Cys Leu Ser Asp Leu Pro
        35                  40                  45

Glu Asp Arg Val Asp Val Thr Ala Tyr Phe Asp Pro Val Lys Thr Thr
    50                  55                  60

Lys Asp Lys Ile Tyr Cys Lys Arg Gly Gly Phe Ile Pro Glu Tyr Asp
65                  70                  75                  80

Phe Asp Ala Arg Glu Phe Gly Leu Asn Met Phe Gln Met Glu Asp Ser
                85                  90                  95

Asp Ala Asn Gln Thr Val Thr Leu Leu Lys Val Lys Glu Ala Leu Glu
            100                 105                 110

Asp Ala Gly Ile Glu Ala Leu Ser Lys Glu Lys Lys Asn Ile Gly Cys
        115                 120                 125

Val Leu Gly Ile Gly Gly Gly Gln Lys Ser Ser His Glu Phe Tyr Ser
```

```
    130                 135                 140

Arg Leu Asn Tyr Val Val Val Glu Lys Val Leu Arg Lys Met Gly Met
145                 150                 155                 160

Pro Glu Glu Asp Val Gln Ala Ala Val Glu Lys Tyr Lys Ala Asn Phe
                165                 170                 175

Pro Glu Trp Arg Leu Asp Ser Phe Pro Gly Phe Leu Gly Asn Val Thr
            180                 185                 190

Ala Gly Arg Cys Thr Asn Thr Phe Asn Leu Asp Gly Met Asn Cys Val
        195                 200                 205

Val Asp Ala Ala Cys Ala Ser Ser Leu Ile Ala Val Lys Val Ala Ile
    210                 215                 220

Asp Glu Leu Leu His Gly Asp Cys Asp Met Met Ile Thr Gly Ala Thr
225                 230                 235                 240

Cys Thr Asp Asn Ser Ile Gly Met Tyr Met Ala Phe Ser Lys Thr Pro
                245                 250                 255

Val Phe Ser Thr Asp Pro Ser Val Arg Ala Tyr Asp Glu Lys Thr Lys
            260                 265                 270

Gly Met Leu Ile Gly Glu Gly Ser Ala Met Leu Val Leu Lys Arg Tyr
        275                 280                 285

Ala Asp Ala Val Arg Asp Gly Asp Glu Ile His Ala Val Ile Arg Gly
    290                 295                 300

Cys Ala Ser Ser Ser Asp Gly Lys Ala Ser Gly Ile Tyr Thr Pro Thr
305                 310                 315                 320

Ile Ser Gly Gln Glu Glu Ala Leu Arg Arg Ala Tyr Met Arg Ala Asn
                325                 330                 335

Val Asp Pro Ala Thr Val Thr Leu Val Glu Gly His Gly Thr Gly Thr
            340                 345                 350

Pro Val Gly Asp Arg Ile Glu Leu Thr Ala Leu Arg Asn Leu Phe Asp
        355                 360                 365

Ser Ala Tyr Gly Asn Glu Lys Glu Lys Val Ala Val Gly Ser Ile Lys
    370                 375                 380

Ser Asn Ile Gly His Leu Lys Ala Val Ala Gly Leu Ala Gly Met Ile
385                 390                 395                 400

Lys Val Ile Met Ala Leu Lys His Lys Thr Leu Pro Ala Thr Ile Asn
                405                 410                 415

Val Asp Glu Pro Pro Lys Leu Tyr Asp Asn Thr Pro Ile Thr Asp Ser
            420                 425                 430

Ser Leu Tyr Ile Asn Thr Met Asn Arg Pro Trp Phe Pro Ala Pro Gly
        435                 440                 445

Val Pro Arg Arg Ala Gly Ile Ser Ser Phe Gly Phe Gly Gly Ala Asn
    450                 455                 460

Tyr His Ala Val Leu Glu Glu Ala Glu Pro Glu His Gln Lys Ala Tyr
465                 470                 475                 480

Arg Leu Asn Lys Arg Pro Gln Pro Val Leu Leu Met Ala Ser Ser Thr
                485                 490                 495

Gln Ala Leu Ala Ser Leu Cys Glu Ala Gln Leu Lys Glu Phe Glu Lys
            500                 505                 510

Ala Ile Glu Glu Asn Lys Thr Val Lys Asn Thr Ala Tyr Ile Lys Cys
        515                 520                 525

Val Asp Phe Cys Glu Lys Phe Lys Phe Pro Gly Ser Ile Pro Ser Ser
    530                 535                 540

Asn Ala Arg Leu Gly Phe Leu Val Lys Glu Ala Asp Asp Ala Thr Glu
545                 550                 555                 560
```

```
Thr Leu Arg Ala Ile Val Ala Gln Phe Gln Lys Ser Ala Gly Lys Asp
                565                 570                 575

Ser Trp His Leu Pro Arg Gln Gly Val Ser Phe Arg Ala Gln Gly Ile
            580                 585                 590

Asn Thr Thr Gly Gly Val Ala Ala Leu Phe Ser Gly Gln Gly Ala Gln
        595                 600                 605

Tyr Thr His Met Phe Ser Glu Val Ala Met Asn Trp Pro Gln Phe Arg
    610                 615                 620

Glu Ser Ile Ser Asp Met Asp Arg Ala Gln Ala Lys Val Ala Gly Ala
625                 630                 635                 640

Asp Lys Asp Tyr Glu Arg Val Ser Gln Val Leu Tyr Pro Arg Lys Pro
                645                 650                 655

Tyr Asn Ser Glu Pro Glu Gln Asp His Lys Lys Ile Ser Leu Thr Ser
            660                 665                 670

Tyr Ser Gln Pro Ser Thr Leu Ala Cys Ala Leu Gly Ala Tyr Glu Ile
        675                 680                 685

Phe Lys Gln Ala Gly Phe Lys Pro Asp Phe Ala Ala Gly His Ser Leu
    690                 695                 700

Gly Glu Phe Ala Ala Leu Tyr Ala Ala Asp Cys Val Asn Arg Asp Asp
705                 710                 715                 720

Leu Phe Glu Leu Val Cys Arg Arg Ala Arg Ile Met Gly Gly Lys Asp
                725                 730                 735

Ala Pro Ala Thr Pro Lys Gly Cys Met Ala Ala Val Ile Gly Pro Asn
            740                 745                 750

Ala Glu Lys Ile Gln Ile Arg Thr Ala Asp Val Trp Leu Gly Asn Cys
        755                 760                 765

Asn Ser Pro Ser Gln Thr Val Ile Thr Gly Ser Val Glu Gly Ile Lys
    770                 775                 780

Lys Glu Ser Glu Leu Leu Gln Ser Glu Gly Phe Arg Val Val Pro Leu
785                 790                 795                 800

Ala Cys Glu Ser Ala Phe His Ser Pro Gln Met Gln Asn Ala Ser Ser
                805                 810                 815

Ala Phe Lys Asp Val Leu Ser Lys Val Ala Phe Arg Gln Pro Ser Ala
            820                 825                 830

Gln Thr Lys Leu Phe Ser Asn Val Ser Gly Glu Thr Tyr Ser Asn Asn
        835                 840                 845

Ala Gln Asp Leu Leu Lys Glu His Met Thr Ser Ser Val Lys Phe Ile
    850                 855                 860

Ser Gln Val Arg Asn Met His Ser Ala Gly Ala Arg Ile Phe Val Glu
865                 870                 875                 880

Phe Gly Pro Lys Gln Val Leu Ser Lys Leu Val Ser Glu Thr Leu Lys
                885                 890                 895

Asp Asp Pro Ser Ile Ile Thr Ile Ser Val Asn Pro Ser Ser Gly Lys
            900                 905                 910

Asp Ala Asp Ile Gln Leu Arg Glu Ala Ala Val Gln Leu Val Val Ala
        915                 920                 925

Gly Val Asn Leu Gln Gly Phe Asp Lys Trp Asp Ala Pro Asp Ala Thr
    930                 935                 940

Arg Leu Gln Pro Ile Lys Lys Lys Lys Thr Thr Leu Arg Leu Ser Ala
945                 950                 955                 960

Ala Thr Tyr Val Ser Asp Lys Thr Lys Lys Ala Arg Glu Ala Ala Met
                965                 970                 975
```

```
Asn Asp Gly Arg Met Leu Ser Cys Val Ser Lys Val Ile Ala Pro Pro
            980                 985                 990

Asp Ala Lys Pro Ile Val Asp Thr  Lys Ala Gln Glu Glu  Val Ala Arg
        995                 1000                 1005

Leu Gln  Lys Gln Leu Gln Asp  Ala Gln Ala Gln Ile  Gln Lys Ala
    1010                 1015                 1020

Lys Ala  Asp Ala Ala Glu Ala  Asp Lys Lys Leu Ala  Ala Ala Lys
    1025                 1030                 1035

Asp Glu  Ala Lys Arg Ala Ala  Ala Ser Ala Pro Val  Gln Lys Gln
    1040                 1045                 1050

Val Asp  Thr Thr Ile Val Asp  Lys His Arg Ala Ile  Leu Lys Ser
    1055                 1060                 1065

Met Leu  Ala Glu Leu Asp Cys  Tyr Ser Thr Pro Gly  Ala Val Ser
    1070                 1075                 1080

Ser Ser  Phe Gln Ala Pro Val  Ala Ala Thr Pro Ala  Pro Val Ala
    1085                 1090                 1095

Ala Pro  Val Ala Ala Ala Pro  Ala Pro Ala Val Asn  Asn Ala Leu
    1100                 1105                 1110

Leu Ala  Lys Ala Glu Ser Val  Val Met Glu Val Leu  Ala Ala Lys
    1115                 1120                 1125

Thr Gly  Tyr Glu Thr Asp Met  Ile Glu Pro Asp Met  Glu Leu Glu
    1130                 1135                 1140

Thr Glu  Leu Gly Ile Asp Ser  Ile Lys Arg Val Glu  Ile Leu Ser
    1145                 1150                 1155

Glu Val  Gln Ala Gln Leu Asn  Val Glu Ala Lys Asp  Val Asp Ala
    1160                 1165                 1170

Leu Ser  Arg Thr Arg Thr Val  Gly Glu Val Val Asn  Ala Met Lys
    1175                 1180                 1185

Ala Glu  Ile Ala Gly Ser Ser  Gly Ala Ala Ala Ala  Ala Pro Ala
    1190                 1195                 1200

Pro Val  Ala Ala Ala Pro Ala  Ala Ala Ala Pro Ala  Val Ser Ser
    1205                 1210                 1215

Ala Leu  Leu Glu Lys Ala Glu  Ser Val Val Met Glu  Val Leu Ala
    1220                 1225                 1230

Ala Lys  Thr Gly Tyr Glu Thr  Asp Met Ile Glu Ala  Asp Met Glu
    1235                 1240                 1245

Leu Glu  Thr Glu Leu Gly Ile  Asp Ser Ile Lys Arg  Val Glu Ile
    1250                 1255                 1260

Leu Ser  Glu Val Gln Ala Met  Leu Asn Val Glu Ala  Lys Asp Val
    1265                 1270                 1275

Asp Ala  Leu Ser Arg Thr Arg  Thr Val Gly Glu Val  Leu Ala Ala
    1280                 1285                 1290

Lys Thr  Gly Tyr Glu Thr Asp  Met Ile Glu Ala Asp  Met Glu Leu
    1295                 1300                 1305

Glu Thr  Glu Leu Gly Ile Asp  Ser Ile Lys Arg Val  Glu Ile Leu
    1310                 1315                 1320

Ser Glu  Val Gln Ala Met Leu  Asn Val Glu Ala Lys  Asp Val Asp
    1325                 1330                 1335

Ala Leu  Ser Arg Thr Arg Thr  Val Gly Glu Val Val  Asn Ala Met
    1340                 1345                 1350

Lys Ala  Glu Ile Ala Gly Ser  Ser Gly Ala Ala Thr  Ala Ser Ala
    1355                 1360                 1365

Pro Ala  Ala Ala Ala Ala Ala  Pro Ala Ile Lys Ile  Ser Thr Val
```

```
    1370                1375                1380

His Gly  Ala Asp Cys Asp Asp  Leu Ser Val Met Ser  Ala Glu Leu
    1385                1390                1395

Val Asp  Ile Arg Arg Ala Asp  Glu Leu Leu Leu Glu  Arg Pro Glu
    1400                1405                1410

Asn Arg  Pro Val Leu Ile Val  Asp Asp Gly Thr Glu  Leu Thr Ser
    1415                1420                1425

Ala Leu  Val Arg Val Leu Gly  Ala Gly Ala Val Val  Leu Thr Phe
    1430                1435                1440

Asp Gly  Leu Gln Leu Ala Gln  Arg Ala Gly Ala Ala  Val Arg His
    1445                1450                1455

Val Gln  Val Lys Asp Leu Ser  Ala Glu Ser Ala Glu  Lys Ala Ile
    1460                1465                1470

Lys Glu  Ala Glu Gln Arg Phe  Gly Gln Leu Gly Gly  Phe Ile Ser
    1475                1480                1485

Gln Gln  Ala Glu Arg Phe Ala  Pro Ala Asp Ile Leu  Gly Phe Thr
    1490                1495                1500

Leu Met  Cys Ala Lys Phe Ala  Lys Ala Ser Leu Cys  Thr Pro Val
    1505                1510                1515

Gln Gly  Gly Arg Ala Phe Phe  Ile Gly Val Ala Arg  Leu Asp Gly
    1520                1525                1530

Arg Leu  Gly Phe Thr Ser Gln  Gly Ser Thr Asp Ser  Leu Thr Arg
    1535                1540                1545

Ala Gln  Arg Gly Ala Ile Phe  Gly Leu Cys Lys Thr  Ile Gly Leu
    1550                1555                1560

Glu Trp  Ser Ala Asn Glu Val  Phe Ala Arg Gly Ile  Asp Ile Ala
    1565                1570                1575

Arg Glu  Val His Pro Glu Asp  Ala Ala Val Ala Ile  Thr Arg Glu
    1580                1585                1590

Met Ser  Cys Ala Asp Asn Arg  Ile Arg Glu Val Gly  Ile Gly Leu
    1595                1600                1605

Asn Gln  Lys Arg Cys Thr Ile  Arg Ala Val Asp Leu  Lys Pro Gly
    1610                1615                1620

Ala Pro  Lys Ile Gln Ile Ser  Gln Asp Asp Val Leu  Leu Val Ser
    1625                1630                1635

Gly Gly  Ala Arg Gly Ile Thr  Pro Leu Cys Ile Arg  Glu Ile Thr
    1640                1645                1650

Arg Gln  Val Arg Gly Gly Lys  Tyr Ile Leu Leu Gly  Arg Ser Lys
    1655                1660                1665

Val Pro  Ala Gly Glu Pro Ala  Trp Cys Asn Gly Val  Ser Asp Asp
    1670                1675                1680

Asp Leu  Gly Lys Ala Ala Met  Gln Glu Leu Lys Arg  Ala Phe Ser
    1685                1690                1695

Ala Gly  Glu Gly Pro Lys Pro  Thr Pro Met Thr His  Lys Lys Leu
    1700                1705                1710

Val Gly  Thr Ile Ala Gly Ala  Arg Glu Val Arg Ser  Ser Ile Ala
    1715                1720                1725

Asn Ile  Glu Ala Leu Gly Gly  Lys Ala Ile Tyr Ser  Ser Cys Asp
    1730                1735                1740

Val Asn  Ser Ala Ala Asp Val  Ala Lys Ala Val Arg  Glu Ala Glu
    1745                1750                1755

Ala Gln  Leu Gly Ala Arg Val  Thr Gly Val Val His  Ala Ser Gly
    1760                1765                1770
```

```
Val Leu  Arg Asp Arg Leu Ile  Glu Gln Lys Arg Pro  Asp Glu Phe
    1775                 1780                 1785

Asp Ala  Val Phe Gly Thr Lys  Val Thr Gly Leu Glu  Asn Leu Phe
    1790                 1795                 1800

Gly Ala  Ile Asp Met Ala Asn  Leu Lys His Leu Val  Leu Phe Ser
    1805                 1810                 1815

Ser Leu  Ala Gly Phe His Gly  Asn Ile Gly Gln Ser  Asp Tyr Ala
    1820                 1825                 1830

Met Ala  Asn Glu Ala Leu Asn  Lys Met Gly Leu Glu  Leu Ser Asp
    1835                 1840                 1845

Arg Val  Ser Val Lys Ser Ile  Cys Phe Gly Pro Trp  Asp Gly Gly
    1850                 1855                 1860

Met Val  Thr Pro Gln Leu Lys  Lys Gln Phe Gln Ser  Met Gly Val
    1865                 1870                 1875

Gln Ile  Ile Pro Arg Glu Gly  Gly Ala Asp Thr Val  Ala Arg Ile
    1880                 1885                 1890

Val Leu  Gly Ser Ser Pro Ala  Glu Ile Leu Val Gly  Asn Trp Thr
    1895                 1900                 1905

Thr Pro  Thr Lys Lys Val Gly  Ser Glu Pro Val Val  Ile His Arg
    1910                 1915                 1920

Lys Ile  Ser Ala Ala Ser Asn  Pro Phe Leu Lys Asp  His Val Ile
    1925                 1930                 1935

Gln Gly  Arg Cys Val Leu Pro  Met Thr Ile Ala Val  Gly Cys Leu
    1940                 1945                 1950

Ala Glu  Thr Cys Leu Gly Gln  Phe Pro Gly Tyr Ser  Leu Trp Ala
    1955                 1960                 1965

Ile Glu  Asp Ala Gln Leu Phe  Lys Gly Val Thr Val  Asp Gly Asp
    1970                 1975                 1980

Val Asn  Cys Glu Ile Thr Leu  Lys Pro Ser Gln Gly  Thr Ala Gly
    1985                 1990                 1995

Arg Val  Met Ile Gln Ala Thr  Leu Lys Thr Phe Ala  Ser Gly Lys
    2000                 2005                 2010

Leu Val  Pro Ala Tyr Arg Ala  Val Ile Val Leu Ser  Thr Gln Gly
    2015                 2020                 2025

Lys Pro  Pro Ala Ala Thr Thr  Ser Gln Thr Pro Ser  Leu Gln Ala
    2030                 2035                 2040

Asp Pro  Ala Ala Arg Gly Asn  Pro Tyr Asp Gly Lys  Thr Leu Phe
    2045                 2050                 2055

His Gly  Pro Ala Phe Gln Gly  Leu Lys Glu Ile Ile  Ser Cys Asn
    2060                 2065                 2070

Lys Ser  Gln Leu Val Ala Glu  Cys Thr Phe Ile Pro  Ser Ser Glu
    2075                 2080                 2085

Ser Ala  Gly Glu Phe Ala Ser  Asp Tyr Glu Ser His  Asn Pro Phe
    2090                 2095                 2100

Val Asn  Asp Ile Ala Phe Gln  Ala Met Leu Val Trp  Ile Arg Arg
    2105                 2110                 2115

Thr Leu  Gly Gln Ala Ala Leu  Pro Asn Ser Ile Gln  Arg Ile Val
    2120                 2125                 2130

Gln His  Arg Ala Leu Pro Gln  Asp Lys Pro Phe Tyr  Leu Thr Leu
    2135                 2140                 2145

Lys Ser  Asn Ser Ala Ser Gly  His Ser Gln His Lys  Thr Ser Val
    2150                 2155                 2160
```

```
Gln Phe  His Asn Glu Gln Gly  Asp Leu Phe Val Asp  Ile Gln Ala
    2165                2170                2175

Ser Val  Thr Ser Ser Asp Ser  Leu Ala Phe
    2180                2185


<210> SEQ ID NO 13
<211> LENGTH: 1672
<212> TYPE: PRT
<213> ORGANISM: Schizoochytrium limacinum

<400> SEQUENCE: 13

Leu Lys Lys Glu Lys Glu Lys Glu Lys Glu Lys Glu Lys Glu Lys Glu
1               5                   10                  15

Lys Glu Lys Glu Lys Glu Lys Glu Lys Glu Lys Glu Lys Glu Lys Glu
            20                  25                  30

Lys Glu Lys Glu Lys Glu Glu Glu Lys Glu Glu Glu Lys Glu Lys Glu
        35                  40                  45

Lys Glu Lys Glu Lys Glu Lys Glu Lys Glu Glu Gly Asp Leu Lys Ser
    50                  55                  60

Cys Leu Val Glu Lys Gly Glu Gly Gly Arg Ser Ser Asp Ser Gly Arg
65                  70                  75                  80

Arg Arg Ser Ser Cys Cys Lys Arg Gly Thr Glu Ala Val Ala Val Glu
                85                  90                  95

Gln Ala Glu Ala Thr Ala Asn Leu Glu Leu Asp Pro Val Glu Pro Gln
            100                 105                 110

Gln Glu Gln Glu Pro Asp Gln Val Asp Glu Asp Glu Val Arg Leu Leu
        115                 120                 125

Ser Gly Thr Thr Glu Val Ala Gly Leu Ala Glu Ser Ala Thr Thr Ala
    130                 135                 140

Ile Leu Arg Ser Thr Asp Ala Arg Ala Glu Asn Leu Gln Leu Leu Ala
145                 150                 155                 160

Thr Thr Gln Glu Pro Pro Ser Asp Thr Thr Arg Phe Glu Asn Ser Thr
                165                 170                 175

Ser Leu Glu Ala Ala Thr Ala Leu Ala Asp Asn Gln Thr Gly Pro Glu
            180                 185                 190

Lys Ala Thr Thr Arg Arg Glu Ile Ile Glu Ser Gln Leu Ala Thr Met
        195                 200                 205

Ala Thr Arg Val Lys Thr Asn Lys Lys Pro Cys Trp Glu Met Thr Lys
    210                 215                 220

Glu Glu Leu Thr Ser Gly Lys Asn Val Val Phe Asp Tyr Asp Glu Leu
225                 230                 235                 240

Leu Glu Phe Ala Glu Gly Asp Ile Ser Lys Val Phe Gly Pro Glu Phe
                245                 250                 255

Ser Gln Ile Asp Gln Tyr Lys Arg Arg Val Arg Leu Pro Ala Arg Glu
            260                 265                 270

Tyr Leu Leu Val Thr Arg Val Thr Leu Met Asp Ala Glu Val Asn Asn
        275                 280                 285

Tyr Arg Val Gly Ala Arg Met Val Thr Glu Tyr Asp Leu Pro Val Asn
    290                 295                 300

Gly Glu Leu Ser Glu Gly Gly Asp Cys Pro Trp Ala Val Leu Val Glu
305                 310                 315                 320

Ser Gly Gln Cys Asp Leu Met Leu Ile Ser Tyr Met Gly Ile Asp Phe
                325                 330                 335

Gln Asn Lys Ser Asp Arg Val Tyr Arg Leu Leu Asn Thr Thr Leu Thr
            340                 345                 350
```

```
Phe Tyr Gly Val Ala Gln Glu Gly Glu Thr Leu Glu Tyr Asp Ile Arg
        355                 360                 365

Val Thr Gly Phe Ala Lys Arg Leu Asp Gly Asp Ile Ser Met Phe Phe
    370                 375                 380

Phe Glu Tyr Asp Cys Tyr Val Asn Gly Arg Leu Leu Ile Glu Met Arg
385                 390                 395                 400

Asp Gly Cys Ala Gly Phe Phe Thr Asn Glu Glu Leu Ala Ala Gly Lys
                405                 410                 415

Gly Val Val Phe Thr Arg Ala Asp Leu Leu Ala Arg Glu Lys Thr Lys
            420                 425                 430

Lys Gln Asp Ile Thr Pro Tyr Ala Ile Ala Pro Arg Leu Asn Lys Thr
        435                 440                 445

Val Leu Asn Glu Thr Glu Met Gln Ser Leu Val Asp Lys Asn Trp Thr
    450                 455                 460

Lys Val Phe Gly Pro Glu Asn Gly Met Asp Gln Ile Asn Tyr Lys Leu
465                 470                 475                 480

Cys Ala Arg Lys Met Leu Met Ile Asp Arg Val Thr Lys Ile Asp Tyr
                485                 490                 495

Thr Gly Gly Pro Tyr Gly Leu Gly Leu Leu Val Gly Glu Lys Ile Leu
            500                 505                 510

Glu Arg Asp His Trp Tyr Phe Pro Cys His Phe Val Gly Asp Gln Val
        515                 520                 525

Met Ala Gly Ser Leu Val Ser Asp Gly Cys Ser Gln Leu Leu Lys Met
    530                 535                 540

Tyr Met Leu Trp Leu Gly Leu His Leu Lys Thr Gly Pro Phe Asp Phe
545                 550                 555                 560

Arg Pro Val Asn Gly His Pro Asn Lys Val Arg Cys Arg Gly Gln Ile
                565                 570                 575

Ser Pro His Lys Gly Lys Leu Val Tyr Val Met Glu Ile Lys Glu Met
            580                 585                 590

Gly Tyr Asp Glu Ala Gly Asp Pro Tyr Ala Ile Ala Asp Val Asn Ile
        595                 600                 605

Leu Asp Ile Asp Phe Glu Lys Gly Gln Thr Phe Asp Leu Ala Asn Leu
    610                 615                 620

His Glu Tyr Gly Lys Gly Asp Leu Asn Lys Lys Ile Val Val Asp Phe
625                 630                 635                 640

Lys Gly Ile Ala Leu Lys Leu Gln Lys Arg Ser Gly Pro Ala Val Val
                645                 650                 655

Ala Pro Glu Lys Pro Leu Ala Leu Asn Lys Asp Leu Cys Ala Pro Ala
            660                 665                 670

Val Glu Ala Ile Pro Glu His Ile Leu Lys Gly Asp Ala Leu Ala Pro
        675                 680                 685

Asn Gln Met Thr Trp His Pro Met Ser Lys Ile Ala Gly Asn Pro Thr
    690                 695                 700

Pro Ser Phe Ser Pro Ser Ala Tyr Pro Pro Arg Pro Ile Thr Phe Thr
705                 710                 715                 720

Pro Phe Pro Gly Asn Lys Asn Asp Asn Asn His Val Pro Gly Glu Met
                725                 730                 735

Pro Leu Ser Trp Tyr Asn Met Ala Glu Phe Met Ala Gly Lys Val Ser
            740                 745                 750

Leu Cys Leu Gly Pro Glu Phe Ala Lys Phe Asp Asp Ser Asn Thr Ser
        755                 760                 765
```

```
Arg Ser Pro Ala Trp Asp Leu Ala Leu Val Thr Arg Val Val Ser Val
    770                 775                 780

Ser Asp Met Glu Trp Val Gln Trp Lys Asn Val Asp Cys Asn Pro Ser
785                 790                 795                 800

Lys Gly Thr Met Val Gly Glu Phe Asp Cys Pro Ile Asp Ala Trp Phe
                805                 810                 815

Phe Gln Gly Ser Cys Asn Asp Gly His Met Pro Tyr Ser Ile Leu Met
            820                 825                 830

Glu Ile Ala Leu Gln Thr Ser Gly Val Leu Thr Ser Val Leu Lys Ala
        835                 840                 845

Pro Leu Thr Met Glu Lys Lys Asp Ile Leu Phe Arg Asn Leu Asp Ala
    850                 855                 860

Asn Ala Glu Met Val Arg Ser Asp Ile Asp Leu Arg Gly Lys Thr Ile
865                 870                 875                 880

His Asn Leu Thr Lys Cys Thr Gly Tyr Ser Met Leu Gly Asp Met Gly
                885                 890                 895

Val His Arg Phe Ser Phe Glu Leu Ser Val Asp Gly Val Val Phe Tyr
            900                 905                 910

Lys Gly Thr Thr Ser Phe Gly Trp Phe Val Pro Glu Val Phe Ile Ser
        915                 920                 925

Gln Thr Gly Leu Asp Asn Gly Arg Arg Thr Gln Pro Trp His Ile Glu
    930                 935                 940

Ser Lys Val Pro Ser Ala Gln Val Leu Thr Tyr Asp Val Thr Pro Asn
945                 950                 955                 960

Gly Ala Gly Arg Thr Gln Leu Tyr Ala Asn Ala Pro Lys Gly Ala Gln
                965                 970                 975

Leu Thr Arg Arg Trp Asn Gln Cys Gln Tyr Leu Asp Thr Ile Asp Leu
            980                 985                 990

Val Val Ala Gly Gly Ser Ala Gly  Leu Gly Tyr Gly His  Gly Arg Lys
        995                 1000                1005

Gln Val  Asn Pro Lys Asp Trp  Phe Phe Ser Cys His  Phe Trp Phe
    1010                1015                1020

Asp Ser  Val Met Pro Gly Ser  Leu Gly Val Glu Ser  Met Phe Gln
    1025                1030                1035

Leu Val  Glu Ser Ile Ala Val  Lys Gln Asp Leu Ala  Gly Lys Tyr
    1040                1045                1050

Gly Ile  Thr Asn Pro Thr Phe  Ala His Ala Pro Gly  Lys Ile Ser
    1055                1060                1065

Trp Lys  Tyr Arg Gly Gln Leu  Thr Pro Thr Ser Lys  Phe Met Asp
    1070                1075                1080

Ser Glu  Ala His Ile Val Ser  Ile Glu Ala His Asp  Gly Val Val
    1085                1090                1095

Asp Ile  Val Ala Asn Gly Asn  Leu Trp Ala Asp Gly  Leu Arg Val
    1100                1105                1110

Tyr Asn  Val Ser Asn Ile Arg  Val Arg Ile Val Ala  Gly Ala Ala
    1115                1120                1125

Pro Ala  Ala Ala Ala Ala Ala  Ala Ala Val Ala Ala  Pro Ala Ala
    1130                1135                1140

Ala Pro  Ala Pro Val Ala Ala  Ser Gly Pro Ala Gln  Thr Ile Thr
    1145                1150                1155

Leu Lys  Gln Leu Lys Ala Glu  Leu Leu Asp Val Glu  Lys Pro Leu
    1160                1165                1170

Tyr Ile  Ser Ser Ser Asn Gly  Gln Val Lys Lys His  Ala Asp Val
```

```
    1175                1180                1185

Ala Gly  Gly Gln Ala Thr Ile  Val Gln Ala Cys Ser  Leu Ser Asp
    1190                1195                1200

Leu Gly  Asp Glu Gly Phe Met  Lys Thr Tyr Gly Val  Val Ala Pro
    1205                1210                1215

Leu Tyr  Thr Gly Ala Met Ala  Lys Gly Ile Ala Ser  Ala Asp Leu
    1220                1225                1230

Val Ile  Ala Thr Gly Lys Arg  Lys Ile Leu Gly Ser  Phe Gly Ala
    1235                1240                1245

Gly Gly  Leu Pro Met His Ile  Val Arg Ala Ala Val  Glu Lys Ile
    1250                1255                1260

Gln Ala  Glu Leu Pro Asn Gly  Pro Phe Ala Val Asn  Leu Ile His
    1265                1270                1275

Ser Pro  Phe Asp Ser Asn Leu  Glu Lys Gly Asn Val  Asp Leu Phe
    1280                1285                1290

Leu Glu  Lys Gly Val Thr Val  Val Glu Ala Ser Ala  Phe Met Thr
    1295                1300                1305

Leu Thr  Pro Gln Val Val Arg  Tyr Arg Ala Ala Gly  Leu Ser Arg
    1310                1315                1320

Asn Ala  Asp Gly Ser Ile Asn  Ile Lys Asn Arg Ile  Ile Gly Lys
    1325                1330                1335

Val Ser  Arg Thr Glu Leu Ala  Glu Met Phe Ile Arg  Pro Ala Pro
    1340                1345                1350

Gln Asn  Leu Leu Asp Lys Leu  Ile Gln Ser Gly Glu  Ile Thr Lys
    1355                1360                1365

Glu Gln  Ala Glu Leu Ala Lys  Leu Val Pro Val Ala  Asp Asp Ile
    1370                1375                1380

Ala Val  Glu Ala Asp Ser Gly  Gly His Thr Asp Asn  Arg Pro Ile
    1385                1390                1395

His Val  Ile Leu Pro Leu Ile  Ile Asn Leu Arg Asn  Arg Leu His
    1400                1405                1410

Lys Glu  Cys Gly Tyr Pro Ala  His Leu Arg Val Arg  Val Gly Ala
    1415                1420                1425

Gly Gly  Gly Val Gly Cys Pro  Gln Ala Ala Ala Ala  Ala Leu Ala
    1430                1435                1440

Met Gly  Ala Ala Phe Leu Val  Thr Gly Thr Val Asn  Gln Val Ala
    1445                1450                1455

Lys Gln  Ser Gly Thr Cys Asp  Asn Val Arg Lys Gln  Leu Cys Met
    1460                1465                1470

Ala Thr  Tyr Ser Asp Val Cys  Met Ala Pro Ala Ala  Asp Met Phe
    1475                1480                1485

Glu Glu  Gly Val Lys Leu Gln  Val Leu Lys Lys Gly  Thr Met Phe
    1490                1495                1500

Pro Ser  Arg Ala Asn Lys Leu  Tyr Glu Leu Phe Cys  Lys Tyr Asp
    1505                1510                1515

Ser Phe  Glu Ser Met Pro Ala  Thr Glu Leu Glu Arg  Val Glu Lys
    1520                1525                1530

Arg Ile  Phe Gln Cys Pro Leu  Ala Asp Val Trp Ala  Glu Thr Ser
    1535                1540                1545

Asp Phe  Tyr Ile Asn Arg Leu  His Asn Pro Glu Lys  Ile Thr Arg
    1550                1555                1560

Ala Glu  Arg Asp Pro Lys Leu  Lys Met Ser Leu Cys  Phe Arg Trp
    1565                1570                1575
```

```
Tyr Leu  Gly Leu Ala Ser Arg  Trp Ala Asn Thr Gly  Glu Ala Gly
    1580                 1585                 1590

Arg Val  Met Asp Tyr Gln Val  Trp Cys Gly Pro Ala  Ile Gly Ala
    1595                 1600                 1605

Phe Asn  Asp Phe Ile Lys Gly  Ser Tyr Leu Asp Pro  Ala Val Ser
    1610                 1615                 1620

Gly Glu  Tyr Pro Asp Val Val  Gln Ile Asn Leu Gln  Ile Leu Arg
    1625                 1630                 1635

Gly Ala  Cys Tyr Leu Arg Arg  Leu Asn Val Ile Arg  Asn Asp Pro
    1640                 1645                 1650

Arg Val  Ser Ile Glu Val Glu  Asp Ala Glu Phe Val  Tyr Glu Pro
    1655                 1660                 1665

Thr Asn  Ala Leu
    1670


<210> SEQ ID NO 14
<211> LENGTH: 21
<212> TYPE: PRT
<213> ORGANISM: Schizoochytrium limacinum

<400> SEQUENCE: 14

Met Ser Thr Ile Arg Leu Ser His His Ala Asn Ala Lys Cys Leu Gly
1               5                   10                  15

Ser Ser Gln Lys Cys
            20


<210> SEQ ID NO 15
<211> LENGTH: 2352
<212> TYPE: DNA
<213> ORGANISM: Artificial Sequence
<220> FEATURE:
<223> OTHER INFORMATION: Synthesized

<400> SEQUENCE: 15

cccaccccag cttcaaaagc gctctaccgt tcgtataatg tatgctatac gaagttattc     60

tctctccttg tcaactcaca cccgaaatcg ttaagcattt ccttctgagt ataagaatca    120

ttcaaaggcg cgccacagga ctagtcccac acaccatagc ttcaaaatgt ttctactcct    180

tttttactct tccagatttt ctcggactcc gcgcatcgcc gtaccacttc aaaacaccca    240

agcacagcat actaaatttt ccctctttct tcctctaggg tgtcgttaat tacccgtact    300

aaaggtttgg aaaagaaaaa agagaccgcc tcgtttcttt ttcttcgtcg aaaaaggcaa    360

taaaaatttt tatcacgttt ctttttcttg aaattttttt ttttagtttt tttctctttc    420

agtgacctcc attgatattt aagttaataa acggtcttca atttctcaag tttcagtttc    480

atttttcttg ttctattaca actttttttta cttcttgttc attagaaaga aagcatagca    540

atctaatcta aggggcggtg ttgacaatta atcatcggca tagtatatcg gcatagtata    600

atacgacaag gtgaggaact aaaccatggc caagttgacc agtgccgttc cggtgctcac    660

cgcgcgcgac gtcgccggag cggtcgagtt ctggaccgac cggctcgggt tctcccggga    720

cttcgtggag gacgacttcg ccggtgtggt ccgggacgac gtgaccctgt tcatcagcgc    780

ggtccaggac caggtggtgc cggacaacac cctggcctgg gtgtgggtgc gcggcctgga    840

cgagctgtac gccgagtggt cggaggtcgt gtccacgaac ttccgggacg cctccgggcc    900

ggccatgacc gagatcggcg agcagccgtg ggggcgggag ttcgccctgc gcgacccggc    960

cggcaactgc gtgcacttcg tggccgagga gcaggactga caattgaagc acgctagcct   1020
```

-continued

```
catgtaatta gttatgtcac gcttacattc acgccctccc tccacatccg ctctaaccga   1080

aaaggaagga gttagacaac ctgaagtcta ggtccctatt tattttttta tagttatgtt   1140

agtattaaga acgttattta tatttcaaat ttttcttttt tttctgtaca gacgcgtgta   1200

cgcatgtaac attatactga aaaccttgct tgagaaggtt ttgggacgct cgaaggcttt   1260

aatttgcaag cttggcgtaa tcatggtcat agctgtttcc tgtgtgaaat tgttatccgc   1320

tcacaattcc acacaacata cgagccggaa gcataaagtg taaagcctgg ggtgcctaat   1380

gagtgagcta actcacatta attgcgttgc gctcactgcc cgctttccag tcgggaaacc   1440

tgtcgtgcca gctgcattaa tgaatcggcc aacgcgcggg gagaggcggt ttgcgtattg   1500

ggcgctcttc cgcttcctcg ctcactgact cgctgcgctc ggtcgttcgg ctgcggcgag   1560

cggtatcagc tcactcaaag gcggtaatac ggttatccac agaatcaggg gataacgcag   1620

gaaagaacat gtgagcaaaa ggccagcaaa aggccaggaa ccgtaaaaag gccgcgttgc   1680

tggcgttttt ccataggctc cgcccccctg acgagcatca caaaaatcga cgctcaagtc   1740

agaggtggcg aaacccgaca ggactataaa gataccaggc gtttccccct ggaagctccc   1800

tcgtgcgctc tcctgttccg accctgccgc ttaccggata cctgtccgcc tttctccctt   1860

cgggaagcgt ggcgctttct caatgctcac gctgtaggta tctcagttcg gtgtaggtcg   1920

ttcgctccaa gctgggctgt gtgcacgaac cccccgttca gcccgaccgc tgcgccttat   1980

ccggtaacta tcgtcttgag tccaacccgg taagacacga cttatcgcca ctggcagcag   2040

ccactggtaa caggattagc agagcgaggt atgtaggcgg tgctacagag ttcttgaagt   2100

ggtggcctaa ctacggctac actagaagga cagtatttgg tatctgcgct ctgctgaagc   2160

cagttacctt cggaaaaaga gttggtagct cttgatccgg caaacaaacc accgctggta   2220

gcggtggttt ttttgtttgc aagcagcaga ttacgcgcag aaaaaaagga tctcaagaag   2280

atcctttgat ctataacttc gtataatgta tgctatacga acggtaagga ggatattctc   2340

gagactagtc tg                                                       2352
```

STRAIN OF BACTERIA PRODUCING DHA AND EPA, SIX GENE FRAGMENTS IN THE BACTERIAL GENOME AND THEIR APPLICATIONS

PRIORITY CLAIM

The present application is a continuing application of PCT Patent Application No. PCT/CN2018/087613, filed May 21, 2018, and claims the priority of China Application No. 201710398286.7, filed May 31, 2017, and China Application No. 201711102734.0, filed Nov. 10, 2017, each of which is incorporated herein by reference in its entirety.

TECHNICAL FIELD

The present invention relates to the fields of industrial microorganism, food and feed industry, in particular to a strain of bacteria producing DHA and/or EPA, six gene fragments in the bacterial genome and their applications, wherein the six gene fragments are also associated with DHA and/or EPA synthesis.

INCORPORATION BY REFERENCE

The sequence listing provided in the file entitled Sequence_Listing_2019-11-26.txt, which is an ASCII text file that was created on Nov. 26, 2019, and which comprises 115,556 bytes, is hereby incorporated by reference in its entirety.

BACKGROUND ART

Polyunsaturated fatty acids are a class of linear fatty acids containing two or more double bonds, typically having a carbon chain length of 18-22 carbon atoms. According to the position of the double bond, polyunsaturated fatty acids can be divided into ω-3 and ω-6. The polyunsaturated fatty acid molecule, in which the double bond at the farthest end from the carboxyl group is on the third carbon atom from the end, is called ω-3. The polyunsaturated fatty acid molecule, in which the double bond at the farthest end from the carboxyl group is on the sixth carbon atom from the end, is called ω-6. Polyunsaturated fatty acids are a class of indispensable fatty acids in the human body, mainly including docosahexaenoic acid (DHA), docosapentenoic acid (DPA), eicosapentaenoic acid (EPA), etc.

DHA is the most important class of polyunsaturated fatty acids. In molecular structure, DHA is a linear fatty acid containing 22 carbon atoms and 6 double bonds. Because its first double bond appears on the third carbon atom of the methyl end of the fatty acid chain, it belongs to the ω-3 series of fatty acids (OMEGA-3). DHA is mainly found in the brain and retina of the human body and has important physiological functions such as promoting nervous system development, improving retinal function, improving vision, preventing cardiovascular disease, treating cardiovascular disease, resisting inflammation and suppressing allergic reaction and the like. Since the human body itself cannot synthesize enough DHA, DHA is mainly obtained by food intake. Because DHA is often insufficient in daily diets, supplementing DHA or adding DHA to food or milk powder is important for humans, especially infants and the elderly.

At present, there are two main methods for producing DHA: one is the source of traditional DHA, which is extracted from the tissues of marine fish (mainly including trout, mackerel, salmon and sardine), but the quality of fish oil obtained by extraction will be affected by fish species, seasons and changes in fishing grounds, and the quality of fish oil is also affected by the growing shortage of fish resources and environmental pollution; the other is the emerging DHA production method, which uses marine microbes for fermentative production of DHA and the method has the advantages of short period, not being affected by objective conditions, no fishy smell, and the like, and has broad prospects. The marine microorganisms used for fermentative production of DHA are mainly *Schizochytrium*. However, the *Schizochytrium* currently used for fermentative production of DHA is limited in its own total fatty acid content, DHA content, growth rate and other technical indicators and cannot further increase yield and reduce costs.

In DHA-producing strains, the DHA biosynthetic pathway is catalyzed by a series of enzymes in the relevant anabolic pathway. Excavation, transformation and heterologous expression of genes related to the DHA biosynthetic pathway will provide favorable conditions for further increasing the yield of DHA. Therefore, obtaining new key genes in the DHA biosynthetic pathway will facilitate the modification and process optimization of DHA-producing strains. There are two DHA synthesis pathways in nature: (1) elongation-desaturation pathway (E-D pathway), which is based on the fatty acid synthesis pathway and further synthesizes DHA by the action of elongase and desaturase; (2) polyketide synthase pathway (PKS pathway), which uses acetyl CoA and malonyl CoA as precursors to synthesize DHA, mainly under the action of polyketide synthase. Among them, in *Schizochytrium*, the synthesis of DHA mainly adopts the PKS pathway. It is currently believed that the synthesis of DPA and EPA also has an E-D pathway and a PKS pathway.

SUMMARY OF THE INVENTION

The object of the present invention is to prepare DPA and/or EPA.

The present invention first protects a protein combination for the preparation of DPA and/or EPA, which can be the following (X1) or (X2) or (X3) or (X4):

(X1) a protein combination including protein 1, protein 2, protein 3, protein 4, protein 5 and protein 6;

(X2) a protein combination consisting of the protein 1, the protein 2, the protein 3, the protein 4, the protein 5 and the protein 6;

(X3) a protein combination consisting of any two, any three, any four or any five of the protein 1, the protein 2, the protein 3, the protein 4, the protein 5 and the protein 6;

(X4) the protein 1, the protein 2, the protein 3, the protein 4, the protein 5 or the protein 6.

The protein 1 can be a1) or a2) or a3) or a4) or a5):

a1) a protein with the amino acid sequence as shown in SEQ ID NO: 9 in the Sequence Listing;

a2) a fusion protein obtained by ligating tag(s) to the N-terminus or/and C-terminus of the protein with the amino acid sequence as shown in SEQ ID NO: 9 in the Sequence Listing;

a3) a protein obtained by substitution and/or deletion and/or addition of one or more amino acid residues in the amino acid sequence as shown in SEQ ID NO: 9 in the Sequence Listing and having the same function;

a4) a protein having 80% or more identity with the amino acid sequence as shown in SEQ ID NO: 9 in the Sequence Listing, derived from *Schizochytrium* and associated with polyunsaturated fatty acid synthesis;

a5) a protein having the amino acid sequence as shown in SEQ ID NO: 9 in the Sequence Listing.

The protein 2 can be b1) or b2) or b3) or b4) or b5):

b1) a protein with the amino acid sequence as shown in SEQ ID NO: 10 in the Sequence Listing;

b2) a fusion protein obtained by ligating tag(s) to the N-terminus or/and C-terminus of the protein with the amino acid sequence as shown in SEQ ID NO: 10 in the Sequence Listing;

b3) a protein obtained by substitution and/or deletion and/or addition of one or more amino acid residues in the amino acid sequence as shown in SEQ ID NO: 10 in the Sequence Listing and having the same function;

b4) a protein having 80% or more identity with the amino acid sequence as shown in SEQ ID NO: 10 in the Sequence Listing, derived from *Schizochytrium* and associated with polyunsaturated fatty acid synthesis;

b5) a protein having the amino acid sequence as shown in SEQ ID NO: 10 in the Sequence Listing.

The protein 3 can be c1) or c2) or c3) or c4) or c5):

c1) a protein with the amino acid sequence as shown in SEQ ID NO: 11 in the Sequence Listing;

c2) a fusion protein obtained by ligating tag(s) to the N-terminus or/and C-terminus of the protein with the amino acid sequence as shown in SEQ ID NO: 11 in the Sequence Listing;

c3) a protein obtained by substitution and/or deletion and/or addition of one or more amino acid residues in the amino acid sequence as shown in SEQ ID NO: 11 in the Sequence Listing and having the same function;

c4) a protein having 80% or more identity with the amino acid sequence as shown in SEQ ID NO: 11 in the Sequence Listing, derived from *Schizochytrium* and associated with polyunsaturated fatty acid synthesis;

c5) a protein having the amino acid sequence as shown in SEQ ID NO: 11 in the Sequence Listing.

The protein 4 can be d1) or d2) or d3) or d4) or d5):

d1) a protein with the amino acid sequence as shown in SEQ ID NO: 12 in the Sequence Listing;

d2) a fusion protein obtained by ligating tag(s) to the N-terminus or/and C-terminus of the protein with the amino acid sequence as shown in SEQ ID NO: 12 in the Sequence Listing;

d3) a protein obtained by substitution and/or deletion and/or addition of one or more amino acid residues in the amino acid sequence as shown in SEQ ID NO: 12 in the Sequence Listing and having the same function;

d4) a protein having 80% or more identity with the amino acid sequence as shown in SEQ ID NO: 12 in the Sequence Listing, derived from *Schizochytrium* and associated with polyunsaturated fatty acid synthesis;

d5) a protein having the amino acid sequence as shown in SEQ ID NO: 12 in the Sequence Listing.

The protein 5 can be e1) or e2) or e3) or e4) or e5):

e1) a protein with the amino acid sequence as shown in SEQ ID NO: 13 in the Sequence Listing;

e2) a fusion protein obtained by ligating tag(s) to the N-terminus or/and C-terminus of the protein with the amino acid sequence as shown in SEQ ID NO: 13 in the Sequence Listing;

e3) a protein obtained by substitution and/or deletion and/or addition of one or more amino acid residues in the amino acid sequence as shown in SEQ ID NO: 13 in the Sequence Listing and having the same function;

e4) a protein having 80% or more identity with the amino acid sequence as shown in SEQ ID NO: 13 in the Sequence Listing, derived from *Schizochytrium* and associated with polyunsaturated fatty acid synthesis;

e5) a protein having the amino acid sequence as shown in SEQ ID NO: 13 in the Sequence Listing.

The protein 6 can be f1) or f2) or f3) or f4) or f5):

f1) a protein with the amino acid sequence as shown in SEQ ID NO: 14 in the Sequence Listing;

f2) a fusion protein obtained by ligating tag(s) to the N-terminus or/and C-terminus of the protein with the amino acid sequence as shown in SEQ ID NO: 14 in the Sequence Listing;

f3) a protein obtained by substitution and/or deletion and/or addition of one or more amino acid residues in the amino acid sequence as shown in SEQ ID NO: 14 in the Sequence Listing and having the same function;

f4) a protein having 80% or more identity with the amino acid sequence as shown in SEQ ID NO: 14 in the Sequence Listing, derived from *Schizochytrium* and associated with polyunsaturated fatty acid synthesis;

f5) a protein having the amino acid sequence as shown in SEQ ID NO: 14 in the Sequence Listing.

Wherein, SEQ ID NO: 9 in the Sequence Listing consists of 669 amino acid residues, SEQ ID NO: 10 in the Sequence Listing consists of 1193 amino acid residues, SEQ ID NO: 11 in the Sequence Listing consists of 773 amino acid residues, SEQ ID NO: 12 in the Sequence Listing consists of 2189 amino acid residues, SEQ ID NO: 13 in the Sequence Listing consists of 1672 amino acid residues, and SEQ ID NO: 14 in the Sequence Listing consists of 21 amino acid residues.

In order to facilitate the purification of the protein in a1), a tag shown in Table 1 can be ligated to the amino-terminus or carboxyl-terminus of the protein with the amino acid sequence as shown in SEQ ID NO:9 in the Sequence Listing. In order to facilitate the purification of the protein in b1), a tag shown in Table 1 can be ligated to the amino-terminus or carboxyl-terminus of the protein with the amino acid sequence as shown in SEQ ID NO:10 in the Sequence Listing. In order to facilitate the purification of the protein in c1), a tag shown in Table 1 can be ligated to the amino-terminus or carboxyl-terminus of the protein with the amino acid sequence as shown in SEQ ID NO:11 in the Sequence Listing. In order to facilitate the purification of the protein in d1), a tag shown in Table 1 can be ligated to the amino-terminus or carboxyl-terminus of the protein with the amino acid sequence as shown in SEQ ID NO:12 in the Sequence Listing. In order to facilitate the purification of the protein in e1), a tag shown in Table 1 can be ligated to the amino-terminus or carboxyl-terminus of the protein with the amino acid sequence as shown in SEQ ID NO:13 in the Sequence Listing. In order to facilitate the purification of the protein in f1), a tag shown in Table 1 can be ligated to the amino-terminus or carboxyl-terminus of the protein with the amino acid sequence as shown in SEQ ID NO:14 in the Sequence Listing.

TABLE 1

Sequences of the tags

| Tag | Residue | Sequence |
|---|---|---|
| Poly-Arg | 5-6 (usually 5) | RRRRR |
| Poly-His | 2-10 (usually 6) | HHHHHH |
| FLAG | 8 | DYKDDDDK |

TABLE 1-continued

| Sequences of the tags | | |
|---|---|---|
| Tag | Residue | Sequence |
| Strep-tag II | 8 | WSHPQFEK |
| c-myc | 10 | EQKLISEEDL |

With respect to the protein 1 in above a3), the protein 2 in above b3), the protein 3 in above c3), the protein 4 in above d3), the protein 5 in above e3) and the protein 6 in above f3), the substitution and/or deletion and/or addition of one or more amino acid residues is substitution and/or deletion and/or addition of no more than 10 amino acid residues.

The protein 1 in above a3), the protein 2 in above b3), the protein 3 in above c3), the protein 4 in above d3), the protein 5 in above e3) and the protein 6 in above f3) all can be artificially synthesized, or can be obtained by synthesizing their encoding genes and then conducting biological expression.

The encoding gene of the protein 1 in above a3) can be obtained by deleting the codon(s) of one or more amino acid residues in the DNA sequence as shown in SEQ ID NO: 9 in the Sequence Listing, and/or by conducting missense mutation(s) of one or more base pairs, and/or ligating the encoding sequence(s) of the tag(s) shown in Table 1 to the 5' end and/or 3' end thereof.

The encoding gene of the protein 2 in above b3) can be obtained by deleting the codon(s) of one or more amino acid residues in the DNA sequence as shown in SEQ ID NO: 10 in the Sequence Listing, and/or by conducting missense mutation(s) of one or more base pairs, and/or ligating the encoding sequence(s) of the tag(s) shown in Table 1 to the 5' end and/or 3' end thereof.

The encoding gene of the protein 3 in above c3) can be obtained by deleting the codon(s) of one or more amino acid residues in the DNA sequence as shown in SEQ ID NO: 11 in the Sequence Listing, and/or by conducting missense mutation(s) of one or more base pairs, and/or ligating the encoding sequence(s) of the tag(s) shown in Table 1 to the 5' end and/or 3' end thereof.

The encoding gene of the protein 4 in above d3) can be obtained by deleting the codon(s) of one or more amino acid residues in the DNA sequence as shown in SEQ ID NO: 12 in the Sequence Listing, and/or by conducting missense mutation(s) of one or more base pairs, and/or ligating the encoding sequence(s) of the tag(s) shown in Table 1 to the 5' end and/or 3' end thereof.

The encoding gene of the protein 5 in above e3) can be obtained by deleting the codon(s) of one or more amino acid residues in the DNA sequence as shown in SEQ ID NO: 13 in the Sequence Listing, and/or by conducting missense mutation(s) of one or more base pairs, and/or ligating the encoding sequence(s) of the tag(s) shown in Table 1 to the 5' end and/or 3' end thereof.

The encoding gene of the protein 6 in above f3) can be obtained by deleting the codon(s) of one or more amino acid residues in the DNA sequence as shown in SEQ ID NO: 14 in the Sequence Listing, and/or by conducting missense mutation(s) of one or more base pairs, and/or ligating the encoding sequence(s) of the tag(s) shown in Table 1 to the 5' end and/or 3' end thereof.

As used above, the term “identity” refers to sequence similarity to a native amino acid sequence. “Identity” includes amino acid sequences having 80%, or 85% or more, or 90% or more, or 95% or more identity with the amino acid sequence of the protein provided by the present invention.

The nucleic acid molecule encoding the protein combination is also within the scope of the present invention.

The nucleic acid molecule encoding the protein 1 can be a DNA molecule as shown in the following A1) or A2) or A3) or A4):

A1) a DNA molecule whose coding region is as shown in positions 1044-3050 from the 5' end of SEQ ID NO: 3 in the Sequence Listing;

A2) a DNA molecule whose nucleotide sequence is as shown in SEQ ID NO: 3 in the Sequence Listing;

A3) a DNA molecule having 75% or more identity with the nucleotide sequence defined by A1) or A2), derived from *Schizochytrium* and encoding the protein 1;

A4) a DNA molecule hybridizing to the nucleotide sequence defined by A1) or A2) under stringent conditions and encoding the protein 1.

The nucleic acid molecule encoding the protein 2 can be a DNA molecule as shown in the following BD or B2) or B3) or B4):

B1) a DNA molecule whose coding regions are shown in positions 1068-2737 and positions 3254-5162 from the 5' end of SEQ ID NO: 4 in the Sequence Listing;

B2) a DNA molecule whose nucleotide sequence is as shown in SEQ ID NO: 4 in the Sequence Listing;

B3) a DNA molecule having 75% or more identity with the nucleotide sequence defined by B1) or B2), derived from *Schizochytrium* and encoding the protein 2;

B4) a DNA molecule hybridizing to the nucleotide sequence defined by B1) or B2) under stringent conditions and encoding the protein 2.

The nucleic acid molecule encoding the protein 3 can be a DNA molecule as shown in the following C1) or C2) or C3) or C4):

C1) a DNA molecule whose coding region is as shown in positions 1094-3415 from the 5' end of SEQ ID NO: 5 in the Sequence Listing;

C2) a DNA molecule whose nucleotide sequence is as shown in SEQ ID NO: 5 in the Sequence Listing;

C3) a DNA molecule having 75% or more identity with the nucleotide sequence defined by C1) or C2), derived from *Schizochytrium* and encoding the protein 3;

C4) a DNA molecule hybridizing to the nucleotide sequence defined by C1) or C2) under stringent conditions and encoding the protein 3.

The nucleic acid molecule encoding the protein 4 can be a DNA molecule as shown in the following D1) or D2) or D3) or D4):

D1) a DNA molecule whose coding regions are as shown in positions 1409-5044, positions 7004-7234 and positions 7700-10399 from the 5' end of SEQ ID NO: 6 in the Sequence Listing;

D2) a DNA molecule whose nucleotide sequence is as shown in SEQ ID NO: 6 in the Sequence Listing;

D3) a DNA molecule having 75% or more identity with the nucleotide sequence defined by D1) or D2), derived from *Schizochytrium* and encoding the protein 4;

D4) a DNA molecule hybridizing to the nucleotide sequence defined by D1) or D2) under stringent conditions and encoding the protein 4.

The nucleic acid molecule encoding the protein 5 can be a DNA molecule as shown in the following E1) or E2) or E3) or E4):

E1) a DNA molecule whose coding region is as shown in positions 1473-6488 from the 5' end of SEQ ID NO: 7 in the Sequence Listing;

E2) a DNA molecule whose nucleotide sequence is as shown in SEQ ID NO: 7 in the Sequence Listing;

E3) a DNA molecule having 75% or more identity with the nucleotide sequence defined by E1) or E2), derived from *Schizochytrium* and encoding the protein 5;

E4) a DNA molecule hybridizing to the nucleotide sequence defined by E1) or E2) under stringent conditions and encoding the protein 5.

The nucleic acid molecule encoding the protein 6 can be a DNA molecule as shown in the following F1) or F2) or F3) or F4):

F1) a DNA molecule whose coding regions are as shown in positions 953-991 and positions 1063-1090 from the 5' end of SEQ ID NO: 8 in the Sequence Listing;

F2) a DNA molecule whose nucleotide sequence is as shown in SEQ ID NO: 8 in the Sequence Listing;

F3) a DNA molecule having 75% or more identity with the nucleotide sequence defined by F1) or F2), derived from *Schizochytrium* and encoding the protein 6;

F4) a DNA molecule hybridizing to the nucleotide sequence defined by F1) or F2) under stringent conditions and encoding the protein 6.

Wherein, the nucleic acid molecule can be DNA, such as cDNA, genomic DNA or recombinant DNA; the nucleic acid molecule can also be RNA, such as mRNA or hnRNA. The nucleic acid molecule can be a nucleic acid molecule formed by gene encoding the protein combination and its regulatory sequence.

Wherein, SEQ ID NO: 3 in the Sequence Listing consists of 4100 nucleotides, and the nucleotide sequence as shown in SEQ ID NO: 3 in the Sequence Listing encodes the amino acid sequence as shown in SEQ ID NO: 9 in the Sequence Listing. SEQ ID NO: 4 in the Sequence Listing consists of 6200 nucleotides, and the nucleotide sequence as shown in SEQ ID NO: 4 in the Sequence Listing encodes the amino acid sequence as shown in SEQ ID NO: 10 in the Sequence Listing. SEQ ID NO: 5 in the Sequence Listing consists of 4500 nucleotides, and the nucleotide sequence as shown in SEQ ID NO: 5 in the Sequence Listing encodes the amino acid sequence as shown in SEQ ID NO: 11 in the Sequence Listing SEQ ID NO: 6 in the Sequence Listing consists of 11100 nucleotides, and the nucleotide sequence as shown in SEQ ID NO: 6 in the Sequence Listing encodes the amino acid sequence as shown in SEQ ID NO: 12 in the Sequence Listing. SEQ ID NO: 7 in the Sequence Listing consists of 7767 nucleotides, and the nucleotide sequence as shown in SEQ ID NO: 7 in the Sequence Listing encodes the amino acid sequence as shown in SEQ ID NO: 13 in the Sequence Listing. SEQ ID NO: 8 in the Sequence Listing consists of 7800 nucleotides, and the nucleotide sequence as shown in SEQ ID NO: 8 in the Sequence Listing encodes the amino acid sequence as shown in SEQ ID NO: 14 in the Sequence Listing.

One of ordinary skill in the art can readily mutate the nucleotide sequence encoding the protein combination of the present invention using known methods, such as directed evolution and point mutation methods. Those artificially modified nucleotides having 75% or more homology to the nucleotide sequence of the protein combination of the present invention are all derived from the nucleotide sequence of the present invention and identical to the sequence of the present invention, as long as they encode the protein combination and is derived from *Schizochytrium*. The term "identity" as used herein refers to sequence similarity to a native nucleic acid sequence. "Identity" includes nucleotide sequence having 75% or more, 80% or more, or 85% or more, or 90% or more, or 95% or more identity with the nucleotide sequence encoding the protein combination of the present invention.

An expression cassette, recombinant vector, recombinant microorganism or transgenic cell line containing the nucleic acid molecule is also within the protection scope of the present invention.

The recombinant vector can be a recombinant plasmid, which is obtained by inserting the nucleic acid molecule encoding the protein 1 (i.e., the DNA molecule as shown in SEQ ID NO: 3 in the Sequence Listing), the nucleic acid molecule encoding the protein 2 (i.e., the DNA molecule as shown in SEQ ID NO: 4 in the Sequence Listing), the nucleic acid molecule encoding the protein 3 (i.e., the DNA molecule as shown in SEQ ID NO: 5 in the Sequence Listing), the nucleic acid molecule encoding the protein 4 (i.e., the DNA molecule as shown in SEQ ID NO: 6 in the Sequence Listing), the nucleic acid molecule encoding the protein 5 (i.e., the DNA molecule as shown in SEQ ID NO: 7 in the Sequence Listing) and the nucleic acid molecule encoding the protein 6 (i.e., the DNA molecule as shown in SEQ ID NO: 8 in the Sequence Listing) into a starting plasmid.

The recombinant microorganism can be obtained by introducing the recombinant vector into a starting microorganism. The starting microorganism can be a yeast, a bacterium, an alga or a fungus. The fungus can be *Schizochytrium*. The *Schizochytrium* can specifically be the strain *Schizochytrium limacinum* Honda et Yokochi ATCC MYA-1381. The recombinant microorganism can specifically be the GS-C06 strain mentioned in the examples.

Use of the protein combination according to any one of the above, or the nucleic acid molecule according to any one of the above, or the expression cassette, recombinant vector, recombinant microorganism or transgenic cell line containing the nucleic acid molecule according to any one of the above in the production of DHA and/or EPA is also within the protection scope of the present invention.

The present invention also protects recombinant strain B, and the preparation method thereof can be as follows: increasing the expression and/or activity of the protein combination in a starting strain to obtain a recombinant strain, i.e., the recombinant strain B. The step of "increasing the expression and/or activity of the protein combination in a starting strain" is realized by introducing a substance that increases the expression and/or activity of the protein combination into the starting strain. The step of "introducing a substance that increases the expression and/or activity of the protein combination into the starting strain" is realized by introducing the nucleic acid molecule encoding the protein combination into the starting strain. The starting strain can be *Schizochytrium*. The *Schizochytrium* can specifically be the strain *Schizochytrium limacinum* Honda et Yokochi ATCC MYA-1381.

The recombinant strain B can specifically be the GS-C06 strain mentioned in the examples.

The present invention further protects a method of producing DHA and/or EPA, which can comprise the following steps in turn:

(1) increasing the expression and/or activity of the protein combination in a starting strain to obtain recombinant strain A; and the ability of the recombinant strain A to produce DHA and/or EPA is improved as compared with the starting strain;

(2) fermenting the recombinant strain A, to obtain DHA and/or EPA.

In the above method, the recombinant strain A can be the recombinant strain B.

In the above methods, the step of "increasing the expression and/or activity of the protein combination in a starting strain to obtain recombinant strain A" is realized by introducing a substance that increases the expression and/or activity of the protein combination into the starting strain.

In the above methods, the step of "introducing a substance that increases the expression and/or activity of the protein combination into the starting strain" is realized by introducing the nucleic acid molecule encoding the protein combination into the starting strain.

In the above methods, the starting strain can be *Schizochytrium*. The *Schizochytrium* can specifically be the strain *Schizochytrium limacinum* Honda et Yokochi ATCC MYA-1381.

In the above methods, the recombinant strain A can specifically be the GS-C06 strain mentioned in the examples.

In the above, the step of "introducing the nucleic acid molecule encoding the protein combination into the starting strain" can be realized by introducing a recombinant vector into the starting strain; the recombinant vector can be a recombinant plasmid, which is obtained by inserting the nucleic acid molecule encoding the protein 1 (i.e., the DNA molecule as shown in SEQ ID NO: 3 in the Sequence Listing), the nucleic acid molecule encoding the protein 2 (i.e., the DNA molecule as shown in SEQ ID NO: 4 in the Sequence Listing), the nucleic acid molecule encoding the protein 3 (i.e., the DNA molecule as shown in SEQ ID NO: 5 in the Sequence Listing), the nucleic acid molecule encoding the protein 4 (i.e., the DNA molecule as shown in SEQ ID NO: 6 in the Sequence Listing), the nucleic acid molecule encoding the protein 5 (i.e., the DNA molecule as shown in SEQ ID NO: 7 in the Sequence Listing) and the nucleic acid molecule encoding the protein 6 (i.e., the DNA molecule as shown in SEQ ID NO: 8 in the Sequence Listing) into an expression vector.

The present invention further protects a strain of bacteria producing docosahexaenoic acid and/or EPA, the strain is *Schizoochytrium limacinum* HS01 with the accession number of CGMCC No. 13746 at China General Microbiological Culture Collection Center.

The present invention further provides a microbial agent comprising the *Schizoochytrium limacinum* HS01 CGMCC No. 13746, or the recombinant strain B according to any one of the above.

Use of the *Schizoochytrium limacinum* HS01 CGMCC No. 13746, or the recombinant strain B according to any one of the above, or the microbial agent in the production of docosahexaenoic acid and/or EPA also falls within the protection scope of the present invention.

The present invention further protects a method of producing docosahexaenoic acid and/or EPA, comprising the step of fermenting the *Schizoochytrium limacinum* HS01 CGMCC No. 13746, or the recombinant strain B according to any one of the above, to obtain docosahexaenoic acid and/or EPA.

The deposit of the referenced strain *Schizoochytrium limacinum* HS01 CGMCC No. 13746 under the Budapest Treaty was received by the China General Microbiological Culture Collection Center (CGMCC) on Mar. 10, 2017, all restrictions on the availability of the deposit have been removed. The viability of the deposit was confirmed on Mar. 17, 2017, will be maintained for the duration of the patent term.

The referenced strain *Schizochytrium limacinum* Honda et Yokochi ATCC MYA-1381 is deposited at the American Type Culture Collection (ATCC, address: American Type Culture Collection (ATCC) 10801 University Boulevard Manassas, Va. 20110 USA), and the public can obtain the strain from the American Type Culture Collection.

In the above method, the fermentation medium solutes used in the fermentation culture and the solubility thereof can be: glucose 20-120 g/L (such as 20-60 g/L, 60-120 g/L, 20 g/L, 60 g/L or 120 g/L), glutamic acid or sodium glutamate 5-15 g/L (such as 5-10 g/L, 10-15 g/L, 5 g/L, 10 g/L or 15 g/L), corn syrup dry powder 3-15 g/L (such as 3-10 g/L, 10-15 g/L, 3 g/L, 10 g/L or 15 g/L), $Na_2SO_4$ 5-24 g/L (such as 5-14 g/L, 14-24 g/L, 5 g/L, 14 g/L or 24 g/L), KCl 0.1-1.0 g/L (such as 0.1-0.5 g/L, 0.5-1.0 g/L, 0.1 g/L, 0.5 g/L or 1.0 g/L) $MgSO_4$ 1.0-3.0 g/L (such as 1.0-2.0 g/L, 2.0-3.0 g/L, 1.0 g/L, 2.0 g/L or 3.0 g/L), $K_2SO_4$ 0.3-1.5 g/L (such as 0.3-1.0 g/L, 1.0-1.5 g/L, 0.3 g/L, 1.0 g/L or 1.5 g/L), $KH_2PO_4$ 0.5-1.5 g/L (such as 0.5-1.0 g/L, 1.0-1.5 g/L, 0.5 g/L, 1.0 g/L or 1.5 g/L), $(NH_4)_2SO_4$ 0.5-1.5 g/L (such as 0.5-1.0 g/L, 1.0-1.5 g/L, 0.5 g/L, 1.0 g/L or 1.5 g/L), $CaCl_2$ 0.1-1.0 g/L (such as 0.1-0.5 g/L, 0.5-1.0 g/L, 0.1 g/L, 0.5 g/L or 1.0 g/L); solvent can be water; pH can range from 5.0-6.5 (such as 5.0, 6.0 or 6.5). The fermentation medium can specifically be: 60 g glucose, 10 g glutamic acid or sodium glutamate, 10 g corn syrup dry powder, 14 g $Na_2SO_4$, 0.5 g KCl, 2.0 g $MgSO_4$, 1.0 g $K_2SO_4$, 1.0 g $KH_2PO_4$, 1.0 g $(NH_4)_2SO_4$ and 0.5 g $CaCl_2$ are dissolved in 1 L distilled water and pH is adjusted to 6.0.

In the above method, the initial biomass in the fermentation culture can be $1.0\times10^8$-$2.5\times10^8$ cfu/mL (such as $1.0\times10^8$-$1.5\times10^8$ cfu/mL, $1.5\times10^8$-$2.5\times10^8$ cfu/mL, $1.0\times10^8$ cfu/mL, $1.5\times10^8$ cfu/mL or $2.5\times10^8$ cfu/mL).

In the above methods, the initial biomass in the fermentation culture can be $5.0\times10^8$-$3.0\times10^9$ cfu/mL (such as $5.0\times10^8$-$1.0\times10^9$ cfu/mL, $1.0\times10^9$-$3.0\times10^9$ cfu/mL, $5.0\times10^8$ cfu/mL, $1.0\times10^9$ cfu/mL or $3.0\times10^9$ cfu/mL).

In the above methods, the fermentation culture inoculum can be 3-10% (such as 3-5%, 5-10%, 3%, 5% or 10%).

In the above methods, the culture condition of the fermentation culture can be 22-28° C. (such as 22-25° C., 25-28° C., 22° C., 25° C. or 28° C.) for 72-120 h (such as 72-100 h, 100-120 h, 72 h, 100 h or 120 h), the dissolved oxygen concentration is 5-80% (such as 5-50%, 50-80%, 5%, 50% or 80%).

In the above methods, the "fermenting the *Schizoochytrium limacinum* HS01 CGMCC No. 13746, or the recombinant strain B according to any one of the above" can further comprise preparing a primary seed broth and/or preparing a secondary seed broth and/or preparing a fermented primary seed broth and/or preparing a fermented secondary seed broth;

The step of preparing the primary seed broth can be as follows: shake-flask culturing the *Schizoochytrium limacinum* HS01 CGMCC No. 13746, or the recombinant strain B according to any one of the above, to obtain the primary seed broth;

The step of preparing the secondary seed broth can be as follows: shake-flask culturing the primary seed broth, to obtain the secondary seed broth;

The step of preparing the fermented primary seed broth can be as follows: fermenting the secondary seed broth, to obtain the fermented primary seed broth;

The step of preparing the fermented secondary seed broth can be as follows: fermenting the fermented primary seed broth, to obtain the fermented secondary seed broth.

In the preparation of the primary seed broth and the preparation of the secondary seed broth, the shake-flask medium solutes used in the shake-flask culture and the solubility thereof can be: glucose 10-90 g/L (such as 10-50 g/L, 50-90 g/L, 10 g/L, 50 g/L or 90 g/L), yeast powder 5-25 g/L (such as 5-15 g/L, 15-25 g/L, 5 g/L, 15 g/L or 25 g/L); solvent can be water; the pH is natural. The culture condition of the "shake-flask culture" is culturing at 22-28° C. (such as 22-25° C., 25-28° C., 22° C., 25° C. or 28° C.), 150-250 rpm/min (such as 150-200 rpm/min, 200-250 rpm/min, 150 rpm/min, 200 rpm/min or 250 rpm/min) for 24-48 h (such as 24-36 h, 36-48 h, 24 h, 36 h or 48 h). The inoculum amount of the shake-flask culture is 3-10% (such as 3-5%, 5-10%, 3%, 5% or 10%). The shake-flask medium can specifically be: 50 g glucose and 15 g yeast powder are dissolved in 1 L distilled water, and the pH is natural.

In the preparation of the fermented primary seed broth and the preparation of the fermented secondary seed broth, the seed medium solutes used in the fermentation culture and the solubility thereof can be: glucose 20-100 g/L (such as 20-60 g/L, 60-120 g/L, 20 g/L, 60 g/L or 120 g/L), yeast powder 5-15 g/L (such as 5-10 g/L, 10-15 g/L, 5 g/L, 10 g/L or 15 g/L), $Na_2SO_4$ 5-24 g/L (such as 5-10 g/L, 10-24 g/L, 5 g/L, 10 g/L or 24 g/L), KCl 0.1-1.0 g/L (such as 0.1-0.5 g/L, 0.5-1.0 g/L, 0.1 g/L, 0.5 g/L or 1.0 g/L), $MgSO_4$ 1.0-3.0 g/L (such as 1.0-2.0 g/L, 2.0-3.0 g/L, 1.0 g/L, 2.0 g/L or 3.0 g/L), $K_2SO_4$ 0.3-1.5 g/L (such as 0.3-1.0 g/L, 1.0-1.5 g/L, 0.3 g/L, 1.0 g/L or 1.5 g/L), $KH_2PO_4$ 0.5-1.5 g/L (such as 0.5-1.0 g/L, 1.0-1.5 g/L, 0.5 g/L, 1.0 g/L or 1.5 g/L), $(NH_4)_2SO_4$ 0.5-1.5 g/L (such as 0.5-1.0 g/L, 1.0-1.5 g/L, 0.5 g/L, 1.0 g/L or 1.5 g/L), $CaCl_2$ 0.1-1.0 g/L (such as 0.1-0.5 g/L, 0.5-1.0 g/L, 0.1 g/L, 0.5 g/L or 1.0 g/L); solvent can be water; pH can be 5.0-6.5 (such as 5.0, 6.0 or 6.5). The culture condition of the "fermentation culture" is culturing at 22-28° C. (such as 22-25° C., 25-28° C., 22° C., 25° C. or 28° C.) for 24-48 h (such as 24-36 h, 36-48 h, 24 h, 36 h or 48 h), the dissolved oxygen concentration is 10-80% (such as 10-50%, 50-80%, 10%, 50% or 80%). The inoculum amount of the fermentation culture is 3-10% (such as 3-5%, 5-10%, 3%, 5% or 10%). The seed medium can specifically be: 60 g glucose, 10 g yeast powder, 10 g $Na_2SO_4$, 0.5 g KCl, 2.0 g $MgSO_4$, 1.0 g $K_2SO_4$, 1.0 g $KH_2PO_4$, 1.0 g $(NH_4)_2SO_4$ and 0.5 g $CaCl_2$ are dissolved in 1 L distilled water and the pH is adjusted to 6.0.

The fermentation broth is obtained by fermenting *Schizoochytrium limacinum* HS01 or the recombinant bacteria B according to any one of the above. The results show that DHA accounts for 45.0%-60.0% of the oil and fat in the fermentation broth, and EPA accounts for 0.2%-1.0% of the oil and fat.

Therefore, the use of the *Schizoochytrium limacinum* HS01 provided by the present invention can produce DHA and/or EPA, and has important application value. A set of gene fragments related to DHA and EPA synthesis provided by the present invention consists of gene fragment 1 to gene fragment 6, and their nucleotide sequences are sequentially as shown in SEQ ID NO: 3 to SEQ ID NO: 8 in the Sequence Listing. Experiments have shown that gene fragment 1 to gene fragment 6 are introduced into *Schizoochytrium limacinum* MYA-1381 to obtain the recombinant strain; the ability of the recombinant strain to produce DHA and EPA is greatly enhanced. Therefore, the six gene fragments provided by the present invention, the proteins encoded by these six gene fragments, and the vector, cell or organism containing these six gene fragments have important application value in the production of DHA and EPA.

DESCRIPTION OF THE DEPOSITION

Name of the strain: *Schizoochytrium limacinum*

Latin name: *Schizoochytrium limacinum*

Strain number: HS01

Figure 1:
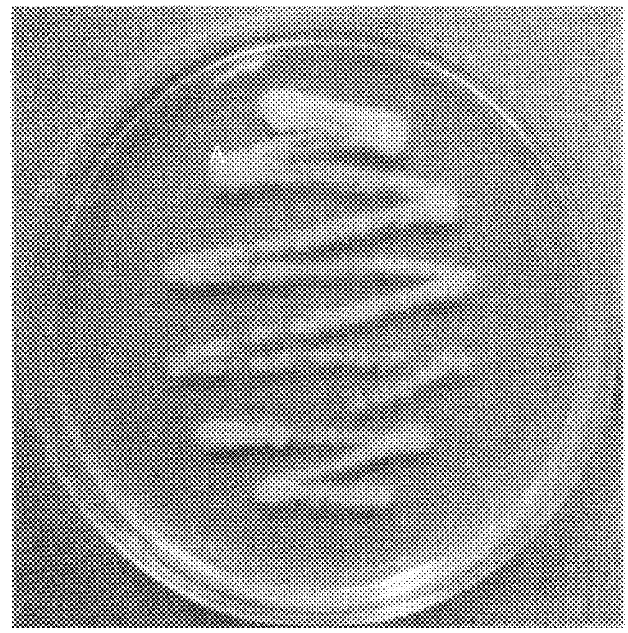
FIG. 1 shows the colony morphological characteristics of *Schizoochytrium limacinum* HS01.

Depositary institution: China General Microbiological Culture Collection Center

Abbreviation of the depositary institution: CGMCC

Address: No. 3, No. 1 Courtyard, Beichen West Road, Chaoyang District, Beijing

Date of deposit: Mar. 10, 2017

Accession number in the collection center: CGMCC No. 13746

DETAILED DESCRIPTION OF THE INVENTION

The present invention will be further described in detail below with reference to the specific embodiments. The examples are given only to illustrate the present invention and are not intended to limit the scope of the present invention.

The experimental methods in the following examples are conventional methods unless otherwise specified.

The materials, reagents and the like used in the following examples are commercially available unless otherwise specified.

For all the quantitative tests in the following examples, three replicate experiments were set, and the results were averaged.

The medium used in the following examples is as follows:

Wort agar medium: 150 g malt extract powder was dissolved in 1 L mixed solution (formed by mixing 1 part by volume of natural sea water and 1 part by volume of distilled water), and the pH is natural; then agar powder was added to a concentration of 15 g/100 mL, to obtain the medium.

Screening liquid medium: 50 g glucose and 15 g yeast powder were dissolved in 1 L mixture (formed by mixing 1 part by volume of natural sea water and 1 part by volume of distilled water), and the pH is natural.

Screening solid medium: agar powder was added to the screening liquid medium to a concentration of 15 g/100 mL, to obtain the medium.

Screening plate: a solid plate was prepared by pouring the screening solid medium of about 55° C. into a culture dish and cooling.

Shake-flask medium: 50 g glucose and 15 g yeast powder were dissolved in 1 L distilled water, and the pH was natural.

Seed medium: glucose 60 g, yeast powder 10 g, $Na_2SO_4$ 10 g, KCl 0.5 g, $MgSO_4$ 2.0 g, $K_2SO_4$ 1.0 g, $KH_2PO_4$ 1.0 g, $(NH_4)_2SO_4$ 1.0 g and $CaCl_2$ 0.5 g were dissolved in 1 L distilled water and the pH was adjusted to 6.0.

Fermentation medium: glucose 60 g, glutamic acid or sodium glutamate 10 g, corn syrup dry powder 10 g, $Na_2SO_4$ 14 g, KCl 0.5 g, $MgSO_4$ 2.0 g, $K_250_4$ 1.0 g, $KH_2PO_4$ 1.0 g, $(NH_4)_250_4$ 1.0 g and $CaCl_2$ 0.5 g were dissolved in 1 L distilled water and the pH was adjusted to 6.0.

The corn syrup dry powder is a product of Solarbio LIFE SCIENCES, and the catalog number is FA0010. The yeast powder is a product of Angel Yeast Co., Ltd., and the catalog number is LMO2. The yeast genome extraction kit is a product of TIANGEN BIOTECH CO., LTD., and the catalog number is DP307. The high-fidelity TransStart FastPfu DNA polymerase is a product of TransGen Biotech, and the catalog number is AP221. The agarose gel DNA recovery kit is a product of TIANGEN BIOTECH CO., LTD., and the catalog number is DP210. The pEASY-Blunt vector is a product of TransGen Biotech, and the catalog number is CB301-01.

The strain *Schizochytrium limacinum* Honda et Yokochi ATCC MYA-1381 is deposited at the American Type Culture Collection (ATCC, address: American Type Culture Collection (ATCC) 10801 University Boulevard Manassas, Va. 20110 USA), and the public can obtain the strain from the American Type Culture Collection. The strain *Schizochytrium limacinum* Honda et Yokochi ATCC MYA-1381 is hereinafter referred to as MYA-1381 for short.

Example 1. Isolation, Identification and Deposit of *Schizoochytrium limacinum* HS01 CGMCC No. 13746

I. Isolation of *Schizoochytrium limacinum* HS01

1. The inventors of the present application collected *Schizochytrium* from multiple places in the mangroves in Yunxiao County, Zhangzhou City, Fujian Province, and the *Schizochytrium* were mixed to obtain a mixed solution; After inoculating 0.5 mL of the mixed solution into 5 mL of screening liquid medium and then culturing at 25° C., 200 rpm/min for 2 d, a culture broth was obtained.

2. The culture broth obtained in step 1 was evenly spread on a screening plate, and stationarily cultured at 25° C. for 2 d to produce single colonies.

3. After completing step 2, single colonies were picked and inoculated into 5 mL fermentation medium, and then cultured at 25° C., 200 rpm/min for 2 d, to obtain a culture broth.

4. The culture broth obtained in step 3 was centrifuged at 4° C., 2000 rpm for 5 min, and the cells were collected.

5. 1.0-2.0 g of the cells were taken into a measuring cylinder with a plug (specification: 100 mL), 15 mL of 8.3 mol/L HCl aqueous solution was first added, the lid was covered and the measuring cylinder was placed in a 70-80° C. water bath for 50-60 min hydrolysis (during this period, shaking the measuring cylinder with a plug once every 10 minutes on the vortex mixer); after cooling to room temperature, 10 mL of 95% (v/v) ethanol aqueous solution was first added, after fully shaking evenly, 20 mL of anhydrous ether was further added to fully shake and extract for 1-2 min, and finally 20 mL of petroleum ether was added. The mixture was fully shaken and extracted for 1-2 min, and layered by standing. The upper organic phase was placed in a glass weighing dish (which has been dried and the empty weight has been weighed). The glass weighing dish was placed on a boiling water bath in a fume hood to make the organic phase fully evaporate (must fully evaporate) and the liquid phase was oil and fat.

6. The oil and fat extracted in step 5 was taken for testing the DHA content according to GB 26400-2011 national food safety standard and testing the composition and content of fatty acid according to the method of AOAC996.06.

The strain with a higher DHA content was selected and repeatedly purified 24 times. One of the screened *Schizochytrium* strain was named as *Schizoochytrium limacinum* HS01.

The *Schizoochytrium limacinum* HS01 monoclone was inoculated into the fermentation medium for 12 successive passages and the DHA content was measured according to the above step. The results showed that the stability of DHA produced by *Schizoochytrium limacinum* HS01 was good.

II. Identification of *Schizoochytrium limacinum* HS01

1. Morphological Identification

The *Schizoochytrium limacinum* HS01 was inoculated onto the wort agar medium, and cultured at 25° C. in the dark. After 5 days, the morphology of the colonies was observed and the morphological characteristics of the strain were analyzed and observed by high-resolution transmission electron microscopy.

Figure 2:
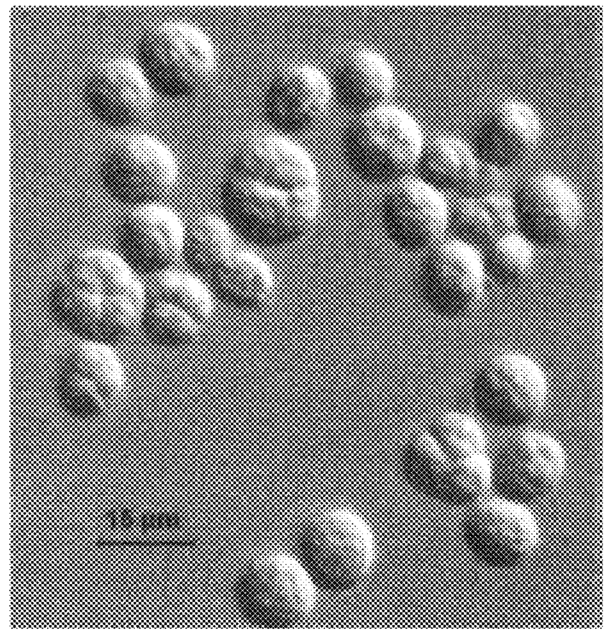
FIG. 2 shows the morphological characteristics of the strain of *Schizoochytrium limacinum* HS01.

The experimental results are shown in FIGS. 1 and 2. The results showed that the colony diameter of *Schizoochytrium limacinum* HS01 was 2-4.3 mm, white (light orange in the later stage) and the edges were not neat; the strain proliferated by fission, the cell wall was thin, spherical, colorless or light orange, transparent and the size was 4.5-15.5 μm, and no zoospores and ectoplasm nets were seen.

2. 18s rDNA sequence homology analysis

The partial sequence of the 18s rDNA of *Schizoochytrium limacinum* HS01 is as shown in SEQ ID NO: 1 in the Sequence Listing.

The partial sequence of the 18s rDNA of *Schizoochytrium limacinum* HS01 is as shown in SEQ ID NO: 2 in the Sequence Listing.

Based on the above identification results, *Schizoochytrium limacinum* HS01 is *Schizoochytrium limacinum.*

III. Deposit of *Schizoochytrium limacinum* HS01

The *Schizoochytrium limacinum* HS01 has been deposited at China General Microbiological Culture Collection Center (Abbreviation: CGMCC, Address: No. 3, No. 1 Courtyard, Beichen West Road, Chaoyang District, Beijing) on Mar. 10, 2017, the accession number is CGMCC No. 13746. The full name of the *Schizoochytrium limacinum* HS01 is *Schizoochytrium limacinum* HS01 CGMCC No. 13746, abbreviated as *Schizoochytrium limacinum* HS01.

Example 2. DHA Production by *Schizoochytrium limacinum* HS01 Fermentation

I. DHA Production by *Schizoochytrium limacinum* HS01 Fermentation

1. The *Schizoochytrium limacinum* HS01 monoclone was inoculated into a shake flask (specification: 10 mL) containing 2 mL shake-flask medium, and cultured at 22-28° C., 150-250 rpm/min for 24-48 h, to obtain a primary seed broth.

2. The primary seed broth was taken and inoculated into a shake flask (with a shake flask specification of 1 L) containing 250 mL shake-flask medium with an inoculum amount of 3-10% (v/v), and cultured at 22-28° C., 150-250 rpm/min for 24-48 h, to obtain a secondary seed broth.

3. The secondary seed broth was taken and inoculated into a fermenter (with a fermenter specification of 5 L) containing 3 L of seed medium with an inoculum amount of 3-10% (v/v), and cultured at 22-28° C. for 24-48 h (the dissolved oxygen was 10-80%), to obtain a fermented primary seed broth.

4. The fermented primary seed broth was taken and inoculated into a fermenter containing 50 L fermentation medium with an inoculum amount of 3-10% (v/v) (the fermenter specification was 100 L; the initial biomass after inoculation was $1.0\times10^8$-$2.5\times10^8$ cfu/mL), and cultured at 22-28° C. for 72-120 h (the dissolved oxygen was 5-80%), to obtain a fermentation broth. The fermentation broth contained DHA.

II. Analysis of Fatty Acid Composition in the Fermentation Broth

According to the method of step 5 of step I in Example 1, the oil and fat of the fermentation broth was extracted, and then the DHA content was detected according to the GB 26400-2011 national food safety standard, and the composition and content of the fatty acid were detected according to the method of AOAC996.06.

The experimental results are shown in Table 2. The results showed that DHA accounted for 45.0%-60.0% of oil and fat.

TABLE 2

| Name | Composition (%) |
|---|---|
| Lauric acid | 0-1.0 |
| Myristic acid | 0.5-1.0 |
| Palmitic acid | 22-32 |
| Stearic acid | 1.0-2.5 |
| Dohomo-γ-linolenic acid | 0.1-0.3 |
| Arachidonic acid | 0-0.8 |
| EPA | 0.2-1.0 |
| DPA | 9.0-17.0 |
| DHA | 45.0-60.0 |

III. Separation and Quality Identification of DHA in the Fermentation Broth

1. The fermentation broth obtained in step I was taken, and sequentially subjected to the cell wall breaking of the *Schizochytrium* and the extraction of the crude oil of the DHA algae oil (the methods of cell wall breaking of the *Schizochytrium* and the extraction of the crude oil of the DHA algae oil are recorded in Chinese patent for invention literature CN 101817738 B).

2. The crude oil of the DHA algal oil extracted in step 1 was refined (the method of refining is recorded in the Chinese patent for invention literature CN 103865642 B).

The quality indicators of the crude oil of the DHA algal oil after refining are shown in Table 3.

TABLE 3

| Indicator | Product DHA algal oil Standard |
|---|---|
| DHA % ≥ | 45.0-66.0 |
| Moisture % ≤ | 0.05 |
| Acid value (KOH), mg/kg ≤ | 0.3 |
| Peroxide value, meq/kg ≤ | 3.0 |
| Trans-fatty acid % ≤ | 1.0 |
| Unsaponifiable matter % ≤ | 2.0 |
| Anisidine value ≤ | 15 |

Example 3: Large-Scale Fermentation of DHA by *Schizoochytrium limacinum* HS01

1. The *Schizoochytrium limacinum* HS01 single colony was inoculated into a shake flask (with a shake flask specification of 250 mL) containing 20 mL shake-flask medium, and cultured at 22-28° C., 150-250 rpm/min for 24-48 h, to obtain a primary seed broth.

2. The primary seed broth was taken and inoculated into a shake flask (with a shake flask specification of 2 L) containing 250 mL shake-flask medium with an inoculum amount of 3-10% (v/v), and cultured at 22-28° C., 150-250 rpm/min for 24-48 h, to obtain a secondary seed broth.

3. The secondary seed broth was taken and inoculated into a fermenter (with a fermenter specification of 1000 L) containing 500 L seed medium with an inoculum amount of 3-10% (v/v), and cultured at 22-28° C. for 24-48 h (the dissolved oxygen was 10-80%), to obtain a fermented primary seed broth with biomass of 15-30 g/L.

4. The fermented primary seed broth was taken and inoculated into a fermenter (with a fermenter specification of 8000-10000 L) containing 5000 L seed medium with an inoculum amount of 5-15% (v/v), and cultured at 22-28° C. for 24-48 h (the dissolved oxygen was 10-80%), to obtain a fermented secondary seed broth with biomass of 15-30 g/L.

5. The fermented secondary seed broth was taken and inoculated into a fermenter containing 3000 L fermentation medium with an inoculum amount of 5-15% (v/v) (the fermenter specification was 75000 L; the initial biomass after inoculation was $5.0\times10^8$-$3.0\times10^9$ cfu/mL), and cultured at 22-28° C. for 72-120 h (the dissolved oxygen was 5-80%), to obtain a fermentation broth. The fermentation broth contained DHA.

The fatty acid composition in the fermentation broth was analyzed according to the method of step II in Example 2. The results showed that in the fermentation broth DHA accounted for 35.0-60.0% of oil and fat.

Example 4. Discovery of Gene Fragments Related to DHA and EPA Synthesis

I. Fermentation of Polyunsaturated Fatty Acids by *Schizoochytrium limacinum* HS01

1. The *Schizoochytrium limacinum* HS01 monoclone was inoculated into a shake flask (specification: 10 mL) containing 2 mL shake-flask medium, and cultured at 22-28° C., 150-250 rpm/min for 24-48 h, to obtain a primary seed broth.

2. The primary seed broth was taken and inoculated into a shake flask (with a shake flask specification of 1 L) containing 250 mL shake-flask medium with an inoculum amount of 3-10% (v/v), and cultured at 22-28° C., 150-250 rpm/min for 24-48 h, to obtain a secondary seed broth.

3. The secondary seed broth was taken and inoculated into a fermenter (with a fermenter specification of 5 L) containing 3 L seed medium with an inoculum amount of 3-10% (v/v) and cultured at 22-28° C. for 24-48 h (the dissolved oxygen was 10-80%), to obtain a fermented primary seed broth.

4. The fermented primary seed broth was taken and inoculated into a fermenter containing 50 L fermentation medium with an inoculum amount of 3-10% (v/v) (the fermenter specification was 100 L; the initial biomass after inoculation was $1.0\times10^8$-$2.5\times10^8$ cfu/mL), and cultured at 22-28° C. for 72-120 h (the dissolved oxygen was 5-80%), to obtain a fermentation broth.

5. According to the method of step 5 of step I in Example 1, the oil and fat of the fermentation broth was extracted, and then the DHA content was detected according to the GB 26400-2011 national food safety standard, and the DPA content was detected according to the GB28404-2012 national food safety standard, the EPA content was detected according to GB5009.168-2016 national food safety standard and the composition and content of fatty acids was detected according to the method of AOAC996.06.

The experimental results are shown in Table 4. The results showed that DHA accounted for 45.0%-60.0% of oil and fat, DPA accounted for 9.0%-17.0% of oil and fat, and EPA accounted for 0.2%-1.0% of oil and fat.

TABLE 4

| Name | Composition (%) |
|---|---|
| Lauric acid | 0-1.0 |
| Myristic acid | 0.5-1.0 |
| Palmitic acid | 22-32 |
| Stearic acid | 1.0-2.5 |
| Dohomo-γ-linolenic acid | 0.1-0.3 |
| Arachidonic acid | 0-0.8 |
| EPA | 0.2-1.0 |
| DPA | 9.0-17.0 |
| DHA | 45.0-60.0 |

II. Fermentation of Polyunsaturated Fatty Acids by MYA-1381

According to the method of step I, the "*Schizoochytrium limacinum* HS01" was replaced with "MYA-1381", and the other steps were unchanged. The results showed that DHA accounted for 12%-23% of oil and fat, DPA accounted for 20%-39% of oil and fat, and EPA accounted for 0.5%-3% of oil and fat.

Based on the above results, *Schizoochytrium limacinum* HS01 is a high-yield strain for the synthesis of DHA and EPA, and MYA-1381 is a low-yield strain for the synthesis of DHA and EPA.

III. Discovery of Gene Fragments Related to DHA and EPA Synthesis

The genomic DNA of *Schizoochytrium limacinum* HS01 and MYA-1381 was respectively extracted using yeast genome extraction kit, and then whole genome sequencing was performed by Novogene using PacBio RS II and Illumina HiSeq 4000.

The results showed that compared with MYA-1381, *Schizoochytrium limacinum* HS01 contained six unique gene fragments, which were named gene fragment 1, gene fragment 2, gene fragment 3, gene fragment 4, gene fragment 5 and gene fragment 6, respectively. Their nucleotide sequences were sequentially as shown in SEQ ID NO: 3-SEQ ID NO: 8 in the Sequence Listing.

The nucleotide sequence of positions 1044-3050 from the 5' end of SEQ ID NO: 3 in the Sequence Listing encodes protein 1, and the amino acid sequence of the protein 1 is as shown in SEQ ID NO: 9 in the Sequence Listing. The nucleotide sequences of positions 1068-2737 and positions 3254-5162 from the 5' end of SEQ ID NO: 4 in the Sequence Listing encode protein 2, and the amino acid sequence of the protein 2 is as shown in SEQ ID NO: 10 in the Sequence Listing. The nucleotide sequence of positions 1094-3415 from the 5' end of SEQ ID NO: 5 in the Sequence Listing encodes protein 3, and the amino acid sequence of the protein 3 is as shown in SEQ ID NO: 11 in the Sequence Listing. The nucleotide sequences of positions 1049-5044, positions 7004-7234 and positions 7700-10399 from the 5' end of SEQ ID NO: 6 in the Sequence Listing encode protein 4, and the amino acid sequence of the protein 4 is as shown in SEQ ID NO: 12 in the Sequence Listing. The nucleotide sequence of positions 1473-6488 from the 5' end of SEQ ID NO: 7 in the Sequence Listing encodes protein 5, and the amino acid sequence of the protein 5 is as shown in SEQ ID NO: 13 in the Sequence Listing. The nucleotide sequences of positions 953-991 and positions 1063-1090 from the 5' end of SEQ ID NO: 8 in the Sequence Listing encode protein 6, and the amino acid sequence of the protein 6 is as shown in SEQ ID NO: 14 in the Sequence Listing.

Example 5. Amplification of the Six Gene Fragments and Synthesis of their Corresponding Primers 1. The genomic DNA of *Schizoochytrium limacinum* HS01 was extracted using the yeast genome extraction kit. Using the genomic DNA as a template, high-fidelity TransStart FastPfu DNA polymerase and primer pairs (primer pair HS01-1, primer pair HS01-2, primer pair HS01-3, primer pair HS01-4, primer pair HS01-5, primer pair HS01-6) were used to carry out PCR amplification, to obtain PCR amplification products.

The nucleotide sequences of the upstream primer and the downstream primer constituting each primer pair are shown in Table 5.

Reaction procedure: 98° C. 2 min; 98° C. 30 s, 56° C. 30 s, 72° C. 3 min, 30 cycles; 72° C. 5 min.

TABLE 5

| Name of primer pair | Name of primer | Nucleotide sequence (5'-3') |
|---|---|---|
| Primer pair HS01-1 | HS01-1-F | CACATTCGCTACAAAACGCCGCAGTTTCTA (SEQ ID NO: 16) |
| | HS01-1-R | CGCAAACTATTTGCTAACCTATTTATCGTA (SEQ ID NO: 17) |
| Primer pair HS01-2 | HS01-2-F | CTGCTGCTACTTCAACATCACTTTGCTCGT (SEQ ID NO: 18) |
| | HS01-2-R | ACTGTAAGTTTATTAAATTGGTCGAGGATG (SEQ ID NO: 19) |
| Primer pair HS01-3 | HS01-3-F | ACCGTGGGCCAAGCTGGCCGCCCCAAGACG (SEQ ID NO: 20) |
| | HS01-3-R | CTTATCTTTGAGGGTAAGAAGGTCTGGTAT (SEQ ID NO: 21) |
| Primer pair HS01-4 | HS01-4-F | CATTGATTGATTGCAGATGATCTTGGGCAA (SEQ ID NO: 22) |
| | HS01-4-R | CTTTCGCCGTTAGAGAAAAAACCCAAACGA (SEQ ID NO: 23) |
| Primer pair HS01-5 | HS01-5-F | TATTGCTATTACTTGAATTTGAATTTGAAT (SEQ ID NO: 24) |
| | HS01-5-R | CAGCAACTTTCACTCGCCCATTCAATCAAT (SEQ ID NO: 25) |
| Primer pair HS01-6 | HS01-6-F | CCACATAATTTGAAAGAAACATTGACCACG (SEQ ID NO: 26) |
| | HS01-6-R | GTGCACCGTTCTTATGCATATTTTAAAATC (SEQ ID NO: 27) |

2. After completing step 1, the PCR amplification products were recovered using an agarose gel DNA recovery kit.

3. After completing step 2, the recovered PCR amplification products were ligated to the pEASY-Blunt vectors to obtain recombinant plasmids.

4. After completing step 3, the recombinant plasmids were sequenced.

The sequencing results showed that the nucleotide sequence of the PCR amplification product amplified by primer pair HS01-1 was as shown in SEQ ID NO: 3 in the Sequence Listing (i.e., the gene fragment 1), the nucleotide sequence of the PCR amplification product amplified by primer pair HS01-2 was as shown in SEQ ID NO: 4 in the Sequence Listing (i.e., the gene fragment 2), the nucleotide sequence of the PCR amplification product amplified by primer pair HS01-3 was as shown in SEQ ID NO: 5 in the Sequence Listing (i.e., the gene fragment 3), the nucleotide sequence of the PCR amplification product amplified by primer pair HS01-4 was as shown in SEQ ID NO: 6 in the Sequence Listing (i.e., the gene fragment 4), the nucleotide sequence of the PCR amplification product amplified by primer pair HS01-5 was as shown in SEQ ID NO: 7 in the Sequence Listing (i.e., the gene fragment 5), the nucleotide sequence of the PCR amplification product amplified by primer pair HS01-6 was as shown in SEQ ID NO: 8 in the Sequence Listing (i.e., the gene fragment 6). Therefore, the six gene fragments can be amplified using the primers in Table 2.

Example 6. Application of the Six Gene Fragments in the Production of DHA and EPA In this example, the nucleotide sequences of the primers involved are shown in Table 6.

TABLE 6

| Name of primer | Nucleotide sequence (5′-3′) |
|---|---|
| HS01-1-UF | CACATTCGCTACAAAACGCCGCAGTTTCTA (SEQ ID NO: 28) |
| H501-1-UR | ACGGTAGAGCGCTTTTGAAGCTGGGGTGGG GTGCGAGGAAGTTGCGTATCCCAGGCTCTC (SEQ ID NO: 29) |
| H501-1-DF | GGTAAGGAGGATATTCTCGAGACTAGTCTG ACGCTCCCATCAATCTTTGGACACTACGAC (SEQ ID NO: 30) |
| HS01-1-DR | CGCAAACTATTTGCTAACCTATTTATCGTA (SEQ ID NO: 31) |
| H501-2-UF | CTGCTGCTACTTCAACATCACTTTGCTCGT (SEQ ID NO: 32) |
| HS01-2-UR | ACGGTAGAGCGCTTTTGAAGCTGGGGTGGG TTGCGATGAATAGCAAACCCCAGAAGTGTG ( SEQ ID NO: 33) |
| HS01-2-DF | GGTAAGGAGGATATTCTCGAGACTAGTCTG GCGAATCCGAGACTCCTTTAAATAGCCAAG (SEQ ID NO: 34) |
| HS01-2-DR | ACTGTAAGTTTATTAAATTGGTCGAGGATG (SEQ ID NO: 35) |
| HS01-3-UF | ACCGTGGGCCAAGCTGGCCGCCCCAAGACG (SEQ ID NO: 36) |
| HS01-3-UR | ACGGTAGAGCGCTTTTGAAGCTGGGGTGGG GTGTGAGGCCACTTGTATCAACAGAGGTAA (SEQ ID NO: 37) |
| HS01-3-DF | GGTAAGGAGGATATTCTCGAGACTAGTCTG TACAATTGAAGAGCCATTGGATAAGTTCGA (SEQ ID NO: 38) |
| HS01-3-DR | CTTATCTTTGAGGGTAAGAAGGTCTGGTAT (SEQ ID NO: 39) |
| HS01-4-UF | CATTGATTGATTGCAGATGATCTTGGGCAA (SEQ ID NO: 40) |
| HS01-4-UR | ACGGTAGAGCGCTTTTGAAGCTGGGGTGGG CCTACAAGGTGTGTTGGTTCGGAAGTTGGT (SEQ ID NO: 41) |
| HS01-4-DF | GGTAAGGAGGATATTCTCGAGACTAGTCTG ATTACAACCACAACTTTCTATAAATAGTGC (SEQ ID NO: 42) |

TABLE 6-continued

| Name of primer | Nucleotide sequence (5′-3′) |
|---|---|
| HS01-4-DR | CTTTCGCCGTTAGAGAAAAAACCCAAACGA (SEQ ID NO: 43) |
| HS01-5-UF | TATTGCTATTACTTGAATTTGAATTTGAAT (SEQ ID NO: 44) |
| HS01-5-UR | ACGGTAGAGCGCTTTTGAAGCTGGGGTGGG GTATGATATGTTATGTACTCGAGGAATGTA (SEQ ID NO: 45) |
| HS01-5-DF | GGTAAGGAGGATATTCTCGAGACTAGTCTG ATCAAAGAAATTAAAAAGAAAACAAACATT (SEQ ID NO: 46) |
| HS01-5-DR | CAGCAACTTTCACTCGCCCATTCAATCAAT (SEQ ID NO: 47) |
| HS01-6-UF | CCACATAATTTGAAAGAAACATTGACCACG (SEQ ID NO: 48) |
| HS01-6-UR | ACGGTAGAGCGCTTTTGAAGCTGGGGTGGG AAATATTCAATCGAAATAAATGCACTGTTT (SEQ ID NO: 49) |
| HS01-6-DF | GGTAAGGAGGATATTCTCGAGACTAGTCTG CCTGATCATCCTTTCGTTACTTCTCAACTC (SEQ ID NO: 50) |
| HS01-6-DR | GTGCACCGTTCTTATGCATATTTTAAAATC (SEQ ID NO: Si) |
| Zeo-F | CCCACCCCAGCTTCAAAAGCGCTCTACCGT (SEQ ID NO: 52) |
| Zeo-R | CAGACTAGTCTCGAGAATATCCTCCTTACC (SEQ ID NO: 53) |

A. The Acquisition of GS-C06 Strain

I. Preparation of Target Fragment HS01-1-Zeo

1. The recombinant plasmid pUC57-LZ was synthesized by GenScript. The recombinant plasmid pUC57-LZ was obtained by ligating the nucleotide sequence as shown in SEQ ID NO: 15 in the Sequence Listing with the pUC57 vector. In SEQ ID NO: 15 in the Sequence Listing, positions 25-58 from the 5' end is Lox66 sequence, positions 626-997 is zeocin resistance gene, and positions 2293-2326 is Lox71 sequence.

2. The genomic DNA of *Schizoochytrium limacinum* HS01 was extracted using the yeast genome extraction kit.

3. Using the genomic DNA of *Schizoochytrium limacinum* HS01 as a template, HS01-1-UF and HS01-1-UR were used as primers to carry out PCR amplification. PCR amplification product of about 3100 bp was obtained, and the PCR amplification product was upstream homologous fragment AU of HS01-1.

4. Using the genomic DNA of *Schizoochytrium limacinum* HS01 as a template, HS01-1-DF and HS01-1-DR were used as primers to carry out PCR amplification. A PCR amplification product of about 1000 bp was obtained, and the PCR amplification product was downstream homologous fragment AD of HS01-1.

5. Using the recombinant plasmid pUC57-LZ synthesized in step 1 as a template, Zeo-F and Zeo-R were used as primers to carry out PCR amplification. A PCR amplification product of about 2350 bp was obtained (nucleotide sequence is as shown in SEQ ID NO: 15 in the Sequence Listing), and the PCR amplification product was a Zeo fragment.

6. Using the upstream homologous fragment AU of HS01-1, the downstream homologous fragment AD of HS01-1 and the Zeo fragment as templates, HS01-1-UF and HS01-1-DR were used as primers to conduct overlap amplification. A PCR amplification product of about 6450 bp was obtained. The PCR amplification product was recovered using the agarose gel DNA recovery kit to obtain a target fragment HS01-1-Zeo.

II. The Acquisition of the Pre-Treated MYA-1381

1. A sterile pre-cooled polypropylene tube (specification: 50 mL) was taken, and 10 mL of MYA-1381 solution (concentration: $1\times10^8$ cfu/mL) was added and centrifuged at 4° C., 5000 r/min for 10 min, the supernatant was discarded and the cells were collected.

2. After completing step 1, the following steps were repeated twice: the polypropylene tube was taken, 10 mL pre-cooled sterile water was added to clean the cells, the resulting mixture was centrifuged at 4° C., 4472 g for 10 min, and the cells were collected.

3. After completing step 2, the polypropylene tube was taken, resuspended by adding 10 mL pre-cooled 1 mol/L sorbitol aqueous solution and centrifuged at 4° C., 5000 r/min for 10 min, and the cells were collected.

4. After completing step 3, the polypropylene tube was taken, resuspended by adding 10 mL pre-cooled 1 mol/L sorbitol aqueous solution to obtain pretreated MYA-1381.

III. Electrotransformation 1. 30 μl, pretreated MYA-1381 was taken and 1 μg target fragment HS01-1-Zeo was added to it. The resulting mixture was mixed gently, allowed to stand for 5 min in an ice bath, and then transferred to an ice-cold gene pulser cuvette for electric shock (electric shock parameters: 0.75 KV, 50 μF).

2. After completing step 1, the gene pulser cuvette was taken and 1 mL seed medium was added to it. The resulting mixture was cultured at 30° C., 200 r/min for 1 h, then centrifuged at 10° C., 5000 r/min for 10 min. The cells and a small amount of supernatant were mixed and spread evenly on the resistant plate, cultured upside down at 30° C. for 48 h to obtain quasi-transformant.

Resistant plate: Zeocin was added to the screening solid medium of about 55'C to a concentration of 200 μg/mL, and then poured into a petri dish, and the solid plate was obtained after cooling.

IV. The Acquisition and Identification of Positive Transformants

The genomic DNA of the quasi-transformant was extracted by the yeast genome extraction kit. Using the genomic DNA as a template, HS01-1-F and HS01-1-R were used as primers to conduct the PCR amplification to obtain PCR amplification product.

If the size of the PCR amplification product of a quasi-transformant was 4100 bp (or its nucleotide sequence was as shown in SEQ ID NO: 3 in the Sequence Listing), the quasi-transformant was a positive transformant.

V. The Acquisition of GS-C01.

The plasmid pSH65 (product of Biovector Inc.; this plasmid contains Cre enzyme) was introduced into the positive transformant, and then the Zeo gene was eliminated according to the procedure of the instructions of plasmid pSH65 to obtain transformant GS-C01.

According to above steps I to V, “HS01-1-UF” was replaced with “HS01-2-UF”, “HS01-1-UR” was replaced with “HS01-2-UR”, “HS01-1-DF” was replaced with “HS01-2-DF”, “HS01-1-DR” was replaced with “HS01-2-DR”, “HS01-1-F” was replaced with “HS01-2-F”, “HS01-1-R” was replaced with “HS01-2-R”, “MYA-1381” was replaced with “transformant GS-C01”, and the other steps were unchanged, to obtain transformant GS-C02.

According to above steps I to V, “HS01-1-UF” was replaced with “HS01-3-UF”, “HS01-1-UR” was replaced with “HS01-3-UR”, “HS01-1-DF” was replaced with “HS01-3-DF”, “HS01-1-DR” was replaced with “HS01-3-DR”, “HS01-1-F” was replaced with “HS01-3-F”, “HS01-1-R” was replaced with “HS01-3-R”, “MYA-1381” was replaced with “transformant GS-C02”, and the other steps were unchanged, to obtain transformant GS-C03.

According to above steps I to V, “HS01-1-UF” was replaced with “HS01-4-UF”, “HS01-1-UR” was replaced with “HS01-4-UR”, “HS01-1-DF” was replaced with “HS01-4-DF”, “HS01-1-DR” was replaced with “HS01-4-DR”, “HS01-1-F” was replaced with “HS01-4-F”, “HS01-1-R” was replaced with “HS01-4-R”, “MYA-1381” was replaced with “transformant GS-C03”, and the other steps were unchanged, to obtain transformant GS-C04.

According to above steps I to V, “HS01-1-UF” was replaced with “HS01-5-UF”, “HS01-1-UR” was replaced with “HS01-5-UR”, “HS01-1-DF” was replaced with “HS01-5-DF”, “HS01-1-DR” was replaced with “HS01-5-DR”, “HS01-1-F” was replaced with “HS01-5-F”, “HS01-1-R” was replaced with “HS01-5-R”, “MYA-1381” was replaced with “transformant GS-C04”, and the other steps were unchanged, to obtain transformant GS-C05.

According to above steps I to V, “HS01-1-UF” was replaced with “HS01-6-UF”, “HS01-1-UR” was replaced with “HS01-6-UR”, “HS01-1-DF” was replaced with “HS01-6-DF”, “HS01-1-DR” was replaced with “HS01-6-DR”, “HS01-1-F” was replaced with “HS01-6-F”, “HS01-1-R” was replaced with “HS01-6-R”, “MYA-1381” was replaced with “transformant GS-C05”, and the other steps were unchanged, to obtain transformant GS-C06.

The transformant GS-C06 was the GS-C06 strain.

B. Application of the Six Gene Fragments in the Production of DHA and EPA

The strain to be tested was *Schizoochytrium limacinum* HS01, MYA-1381 or GS-C06 strain.

1. The monoclone of the strain to be tested was inoculated into a shake flask (specification: 10 mL) containing 2 mL shake-flask medium, and cultured at 22-28° C., 150-250 rpm/min for 24-48 h, to obtain a primary seed broth.

2. The primary seed broth was taken and inoculated into a shake flask (with a shake flask specification of 500 mL) containing 50 mL shake-flask medium with an inoculum amount of 3-10% (v/v), and cultured at 22-28° C., 150-250 rpm/min for 24-48 h, to obtain a secondary seed broth.

3. The secondary seed broth was taken and inoculated into a fermenter (fermenter specification: 1 L) containing 500 mL seed medium with an inoculum amount of 3-10% (v/v), and cultured at 22-28° C. for 24-48 h (the dissolved oxygen was 10-80%), to obtain a tertiary seed broth.

4. The tertiary seed broth was taken and inoculated into a fermenter containing 5 L fermentation medium with an inoculum amount of 3-10% (v/v) (the fermenter specification was 100 L; the initial biomass after inoculation was $3.0\times10^8$-$0.5\times10^8$ cfu/mL), and cultured at 22-28° C. for 72-120 h (the dissolved oxygen was 5-80%), to obtain a fermentation broth. The fermentation broth contained DHA, DPA and EPA.

5. According to the method of step 5 of step I in Example 1, the oil and fat of the fermentation broth was extracted, and then the DHA content was detected according to the GB 5009. 168-2016 national food safety standard, and the DPA content was detected according to the GB28404-2012 national food safety standard, the EPA content was detected according to GB5009.168-2016 national food safety standard.

The experimental results are shown in Table 7. The results showed that transforming the six gene fragments obtained by the present invention into MYA-1381 can obtain a high-yield strain for the synthesis of DHA and EPA (i.e., GS-C06 strain). Therefore, the six gene fragments provided by the present invention, the proteins encoded by the six gene fragments, and the vector, cell or organism containing these six gene fragments have important application value in the production of DHA and EPA. By engineering the proteins encoded by these six gene segments in the starting strain, high-yield engineering strain of DHA and EPA can be constructed.

TABLE 7

| | MYA-1381 | *Schizoochytrium limacinum* HS01 | GS-C06 strain |
|---|---|---|---|
| DHA content in oil and fat (%) | 12.38 | 45.02 | 30.50 |
| DPA content in oil and fat (%) | 25.26 | 12.74 | 17.50 |
| EPA content in oil and fat (%) | 0.50 | 1.30 | 0.71 |

INDUSTRIAL APPLICATION

The *Schizoochytrium limacinum* HS01 provided by the present invention has high production value for producing DHA and/or EPA. A high-yield strain for the synthesis of DHA and/or EPA can be obtained by transforming the six gene fragments obtained by the present invention into a low-yield strain for the synthesis of DHA and/or EPA. Therefore, the six gene fragments provided by the present invention, the proteins encoded by these six gene fragments, and the vector, cell or organism containing these six gene fragments have important application value in the production of DHA and/or EPA. By engineering the proteins encoded by these six gene fragments in a starting strain, a high-yield engineering strain of DHA and/or EPA can be constructed.

The invention claimed is:

1. A recombinant microorganism containing a nucleic acid construct comprising the nucleic acid molecules comprising:

A2), a DNA molecule whose nucleotide sequence is as shown in SEQ ID NO: 3 in the Sequence Listing;

B2), a DNA molecule whose nucleotide sequence is as shown in SEQ ID NO: 4 in the Sequence Listing;

C2), a DNA molecule whose nucleotide sequence is as shown in SEQ ID NO: 5 in the Sequence Listing;

D2), a DNA molecule whose nucleotide sequence is as shown in SEQ ID NO: 6 in the Sequence Listing;

E2), a DNA molecule whose nucleotide sequence is as shown in SEQ ID NO: 7 in the Sequence Listing; and F2), a DNA molecule whose nucleotide sequence is as shown in SEQ ID NO: 8 in the Sequence Listing.

2. The recombinant microorganism according to claim 1, wherein the recombinant microorganism is a recombinant strain B prepared by introducing the nucleic acid molecules consisting of DNA molecules A2), B2), C2), D2), E2), and F2) into a starting strain.

3. The recombinant microorganism according to claim 2, wherein the starting strain is selected from the genus *Schizochytrium.*

4. The recombinant microorganism according to claim 3, wherein the starting strain is *Schizochytrium limacinum* Honda et Yokochi ATCC MYA-1381.

5. A nucleic acid construct composition consisting of:

a nucleic acid construct A comprising a DNA molecule whose nucleotide sequence is as shown in SEQ ID NO: 3 in the Sequence Listing and an inserted heterogeneous resistance selection gene;

a nucleic acid construct B comprising a DNA molecule whose nucleotide sequence is as shown in SEQ ID NO: 4 in the Sequence Listing and an inserted heterogeneous resistance selection gene;

a nucleic acid construct C comprising a DNA molecule whose nucleotide sequence is as shown in SEQ ID NO: 5 in the Sequence Listing and an inserted heterogeneous resistance selection gene;

a nucleic acid construct D comprising a DNA molecule whose nucleotide sequence is as shown in SEQ ID NO: 6 in the Sequence Listing and an inserted heterogeneous resistance selection gene;

a nucleic acid construct E comprising a DNA molecule whose nucleotide sequence is as shown in SEQ ID NO: 7 in the Sequence Listing and an inserted heterogeneous resistance selection gene; and a nucleic acid construct F comprising a DNA molecule whose nucleotide sequence is as shown in SEQ ID NO: 8 in the Sequence Listing and an inserted heterogeneous resistance selection gene.

6. The nucleic acid construct composition according to claim 5, wherein:

the heterogeneous resistance selection gene is a Zeo fragment and wherein the nucleotide sequence of the Zeo fragment is as shown in SEQ ID NO: 15 in the Sequence Listing.

7. The nucleic acid construct composition according to claim 6, wherein:

the nucleic acid construct A is prepared by:

using the genomic DNA of *Schizoochytrium limacinum* HS01 as a template, HS01-1-UF (SEQ ID NO: 28) and HS01-1-UR (SEQ ID NO: 29) were used as primers to carry out PCR amplification, the PCR amplification product was an upstream homologous fragment AU of HS01-1, using the genomic DNA of *Schizoochytrium limacinum* HS01 as a template, HS01-1-DF (SEQ ID NO: 30) and HS01-1-DR (SEQ ID NO: 31) were used as primers to carry out PCR amplification, the PCR amplification product was a downstream homologous fragment AD of HS01-1, using the upstream homologous fragment AU of HS01-1, the downstream homologous fragment AD of HS01-1 and the Zeo fragment as templates, HS01-1-UF (SEQ ID NO: 28) and HS01-1-DR (SEQ ID NO: 31) were used as primers to conduct overlap amplification, the PCR amplification product was target fragment HS01-1-Zeo, the nucleic acid construct A;

the nucleic acid construct B is prepared by:

using the genomic DNA of *Schizoochytrium limacinum* HS01 as a template, HS01-2-UF (SEQ ID NO: 32) and HS01-2-UR (SEQ ID NO: 33) were used as primers to carry out PCR amplification, and the PCR amplification product was an upstream homologous fragment AU of HS01-2, using the genomic DNA of *Schizoochytrium limacinum* HS01 as a template, HS01-2-DF (SEQ ID NO: 34) and HS01-2-DR (SEQ ID NO: 35) were used as primers to carry out PCR amplification, the PCR amplification product was a downstream homologous fragment AD of HS01-2, using the upstream homologous fragment AU of HS01-2, the downstream homologous fragment AD of HS01-2 and the Zeo fragment as templates, HS01-2-UF (SEQ ID NO: 32) and HS01-2-DR (SEQ ID NO: 35) were used as primers to conduct overlap amplification, the PCR amplification product was target fragment HS01-2-Zeo, the nucleic acid construct B;

the nucleic acid construct C is prepared by:

using the genomic DNA of *Schizoochytrium limacinum* HS01 as a template, HS01-3-UF (SEQ ID NO: 36) and HS01-3-UR (SEQ ID NO: 37) were used as primers to carry out PCR amplification, and the PCR amplification product was an upstream homologous fragment AU of HS01-3, using the genomic DNA of *Schizoochytrium limacinum* HS01 as a template, HS01-3-DF (SEQ ID NO: 38) and HS01-3-DR (SEQ ID NO:39) were used as primers to carry out PCR amplification, the PCR amplification product was a downstream homologous fragment AD of HS01-3, using the upstream homologous fragment AU of HS01-3, the downstream homologous fragment AD of HS01-3 and the Zeo fragment as templates, HS01-3-UF (SEQ ID NO: 36) and HS01-3-DR (SEQ ID NO:39) were used as primers to conduct overlap amplification, the PCR amplification product was target fragment HS01-3-Zeo, the nucleic acid construct C;

the nucleic acid construct D is prepared by:

using the genomic DNA of *Schizoochytrium limacinum* HS01 as a template, HS01-4-UF (SEQ ID NO: 40) and HS01-4-UR (SEQ ID NO: 41) were used as primers to carry out PCR amplification, and the PCR amplification product was an upstream homologous fragment AU of HS01-4, using the genomic DNA of *Schizoochytrium limacinum* HS01 as a template, HS01-4-DF (SEQ ID NO: 42) and (SEQ ID NO: 43) were used as primers to carry out PCR amplification, the PCR amplification product was a downstream homologous fragment AD of HS01-4, using the upstream homologous fragment AU of HS01-4, the downstream homologous fragment AD of HS01-4 and the Zeo fragment as templates, HS01-4-UF (SEQ ID NO: 40) and HS01-4-DR (SEQ ID NO: 43) were used as primers to conduct overlap amplification, the PCR amplification product was target fragment HS01-4-Zeo, the nucleic acid construct D;

the nucleic acid construct E is prepared by:

using the genomic DNA of *Schizoochytrium limacinum* HS01 as a template, HS01-5-UF (SEQ ID NO:44) and HS01-5-UR (SEQ ID NO: 45) were used as primers to carry out PCR amplification, and the PCR amplification product was an upstream homologous fragment AU of HS01-5, using the genomic DNA of *Schizoochytrium limacinum* HS01 as a template, HS01-5-DF (SEQ ID NO: 46) and HS01-5-DR (SEQ ID NO: 47) were used as primers to carry out PCR amplification, the PCR amplification product was a downstream homologous fragment AD of HS01-5, using the upstream homologous fragment AU of HS01-5, the downstream homologous fragment AD of HS01-5 and the Zeo fragment as templates, HS01-5-UF (SEQ ID NO:44) and HS01-5-DR (SEQ ID NO: 47) were used as primers to conduct overlap amplification, the PCR amplification product was target fragment HS01-5-Zeo, the nucleic acid construct E; and the nucleic acid construct F is prepared by:

using the genomic DNA of *Schizoochytrium limacinum* HS01 as a template, HS01-6-UF (SEQ ID NO: 48) and HS01-6-UR (SEQ ID NO: 49) were used as primers to carry out PCR amplification, and the PCR amplification product was an upstream homologous fragment AU of HS01-6, using the genomic DNA of *Schizoochytrium limacinum* HS01 as a template, HS01-6-DF (SEQ ID NO: 50) and HS01-6-DR (SEQ ID NO: 51) were used as primers to carry out PCR amplification, the PCR amplification product was a downstream homologous fragment AD of HS01-6, using the upstream homologous fragment AU of HS01-6, the downstream homologous fragment AD of HS01-6 and the Zeo fragment as templates, HS01-6-UF (SEQ ID NO: 48) and HS01-6-DR (SEQ ID NO: 51) were used as primers to conduct overlap amplification, the PCR amplification product was target fragment HS01-6-Zeo, the nucleic acid construct F.

8. A recombinant vector comprising the DNA molecules:

A2), a DNA molecule whose nucleotide sequence is as shown in SEQ ID NO: 3 in the Sequence Listing;

B2), a DNA molecule whose nucleotide sequence is as shown in SEQ ID NO: 4 in the Sequence Listing;

C2), a DNA molecule whose nucleotide sequence is as shown in SEQ ID NO: 5 in the Sequence Listing;

D2), a DNA molecule whose nucleotide sequence is as shown in SEQ ID NO: 6 in the Sequence Listing;

E2), a DNA molecule whose nucleotide sequence is as shown in SEQ ID NO: 7 in the Sequence Listing; and F2), a DNA molecule whose nucleotide sequence is as shown in SEQ ID NO: 8 in the Sequence Listing.

9. A method of producing docosahexaenoic acid and/or EPA, comprising the step of fermenting the recombinant microorganism according to claim 1, to obtain docosahexaenoic acid and/or EPA.

10. The method according to claim 9, wherein the step of fermenting occurs in an aqueous fermentation medium comprising a plurality of solutes, and wherein the solutes comprise glucose 20-120 g/L,
glutamic acid or sodium glutamate 5-15 g/L,
corn syrup dry powder 3-15 g/L,
Na2SO4 5-24 g/L,
KCl 0.1-1.0 g/L,
MgSO4 1.0-3.0 g/L,
K2SO4 0.3-1.5 g/L,
KH2PO4 0.5-1.5 g/L,
(NH4)2SO4 0.5-1.5 g/L,
CaCl2 0.1-1.0 g/L; and wherein the fermentation medium has a pH of 5.0 to 6.5.

* * * * *